US012721514B2

(12) United States Patent
Obara et al.

(10) Patent No.: US 12,721,514 B2
(45) Date of Patent: Sep. 1, 2026

(54) OPHTHALMIC INSTRUMENT, MANAGEMENT METHOD, AND MANAGEMENT DEVICE

(71) Applicant: NIKON CORPORATION, Tokyo (JP)

(72) Inventors: Hideki Obara, Kawasaki (JP); Ken Tomioka, Yokohama (JP); Shota Miyazaki, Fujisawa (JP)

(73) Assignee: NIKON CORPORATION, Tokyo (JP)

(*) Notice: Subject to any disclaimer, the term of this patent is extended or adjusted under 35 U.S.C. 154(b) by 0 days.

(21) Appl. No.: 18/428,731

(22) Filed: Jan. 31, 2024

(65) Prior Publication Data

US 2024/0164635 A1 May 23, 2024

Related U.S. Application Data

(63) Continuation of application No. 16/645,328, filed as application No. PCT/JP2018/033719 on Sep. 11, 2018, now Pat. No. 11,918,286.

(30) Foreign Application Priority Data

Sep. 11, 2017 (JP) ................................ 2017-173945

(51) Int. Cl.
*A61B 3/00* (2006.01)
*A61B 3/024* (2006.01)
(Continued)

(52) U.S. Cl.
CPC .......... *A61B 3/0008* (2013.01); *A61B 3/0016* (2013.01); *A61B 3/024* (2013.01);
(Continued)

(58) Field of Classification Search
CPC ..... A61B 3/0008; A61B 3/0016; A61B 3/024; A61B 3/102; A61B 3/1025; A61B 3/12; A61B 3/18
See application file for complete search history.

(56) References Cited

U.S. PATENT DOCUMENTS

2009/0141240 A1 6/2009 Weitz et al.
2011/0116040 A1 5/2011 Biernat et al.
(Continued)

FOREIGN PATENT DOCUMENTS

JP 2001-290101 A 10/2001
JP 2014-100254 A 6/2014
(Continued)

OTHER PUBLICATIONS

Murai et al., "Development of the fitting method of HMD (eyesight aid) to support visibility of low vision," 1 Lecture proceedings of the 14th Forum on Information Technology, Aug. 24, 2015, vol. 3, (pp. 545-546).

(Continued)

*Primary Examiner* — Jack Dinh
(74) *Attorney, Agent, or Firm* — Foley & Lardner LLP

(57) ABSTRACT

An ophthalmic instrument including a light emitter, an optical system, and a control section. The light emitter includes a light source including at least one out of a first light source unit or a second light source unit that emits light for examining a subject eye. The light emitter is configured to emit light from the light source. The optical system guides light emitted from the light emitter onto a right-eye retina and/or onto a left-eye retina. The control section is configured to control the light emitter and the optical system such that the light is shone onto the right-eye retina and/or onto the left-eye retina.

5 Claims, 30 Drawing Sheets

(51) Int. Cl.
*A61B 3/10* (2006.01)
*A61B 3/12* (2006.01)
*A61B 3/18* (2006.01)

(52) U.S. Cl.
CPC ................ *A61B 3/102* (2013.01); *A61B 3/12* (2013.01); *A61B 3/18* (2013.01)

(56) References Cited

U.S. PATENT DOCUMENTS

| | | | |
|---|---|---|---|
| 2013/0044290 | A1 | 2/2013 | Kawamura |
| 2016/0174835 | A1 | 6/2016 | Hogan |
| 2017/0209044 | A1 | 7/2017 | Ito et al. |
| 2018/0020910 | A1 | 1/2018 | Maeda et al. |
| 2019/0274544 | A1 | 9/2019 | Sugawara et al. |

FOREIGN PATENT DOCUMENTS

| | | | |
|---|---|---|---|
| JP | 2016-140646 | A | 8/2016 |
| JP | 2016-536075 | A | 11/2016 |
| JP | 2017-029483 | A | 2/2017 |

OTHER PUBLICATIONS

Oguchi et al., "Ophthalmic examination method handbook," vol. 4, Igaku-Shoin Ltd, 2005, ISBN 4-260-13780-8, (pp. 156-157).

Shimizu, "Retinal Scanning/Projection Display," The journal of the Institute of Image Information and Television Engineers, 2011, vol. 65, No. 6, (pp. 758-763).

Written Opinion issued in corresponding application No. PCT/JP2018/033719 dated Dec. 4, 2018 with English translation.

Written Opinion of the ISA issued in corresponding International Application No. PCT/JP2018/033719 dated Dec. 4, 2018.

US Non-Final Office Action on U.S. Appl. No. 16/645,328 dated Apr. 13, 2023 (8 pages).

US Notice of Allowance on U.S. Appl. No. 16/645,328 dated Nov. 1, 2023 (7 pages).

JP Office Action Issued in Corresponding Japanese Patent Application No. 2023-153952 Dated Oct. 1, 2024 (5 pages).

JP Office Action issued in corresponding Japanese Application No. 2023-153952 Dated Apr. 8, 2025 (5 pages).

JP Office Action issued in corresponding Japanese Application No. 2025-155348 Dated Feb. 3, 2026 (7 pages).

OPHTHALMIC SYSTEM
10
12
RIGHT
LEFT
16
18
19
20
22
23
24
24R
24L
24R1
24L1
25
27
30
32
34
36
38
40
42
42R
42L
48R
48L
140
14
15
17

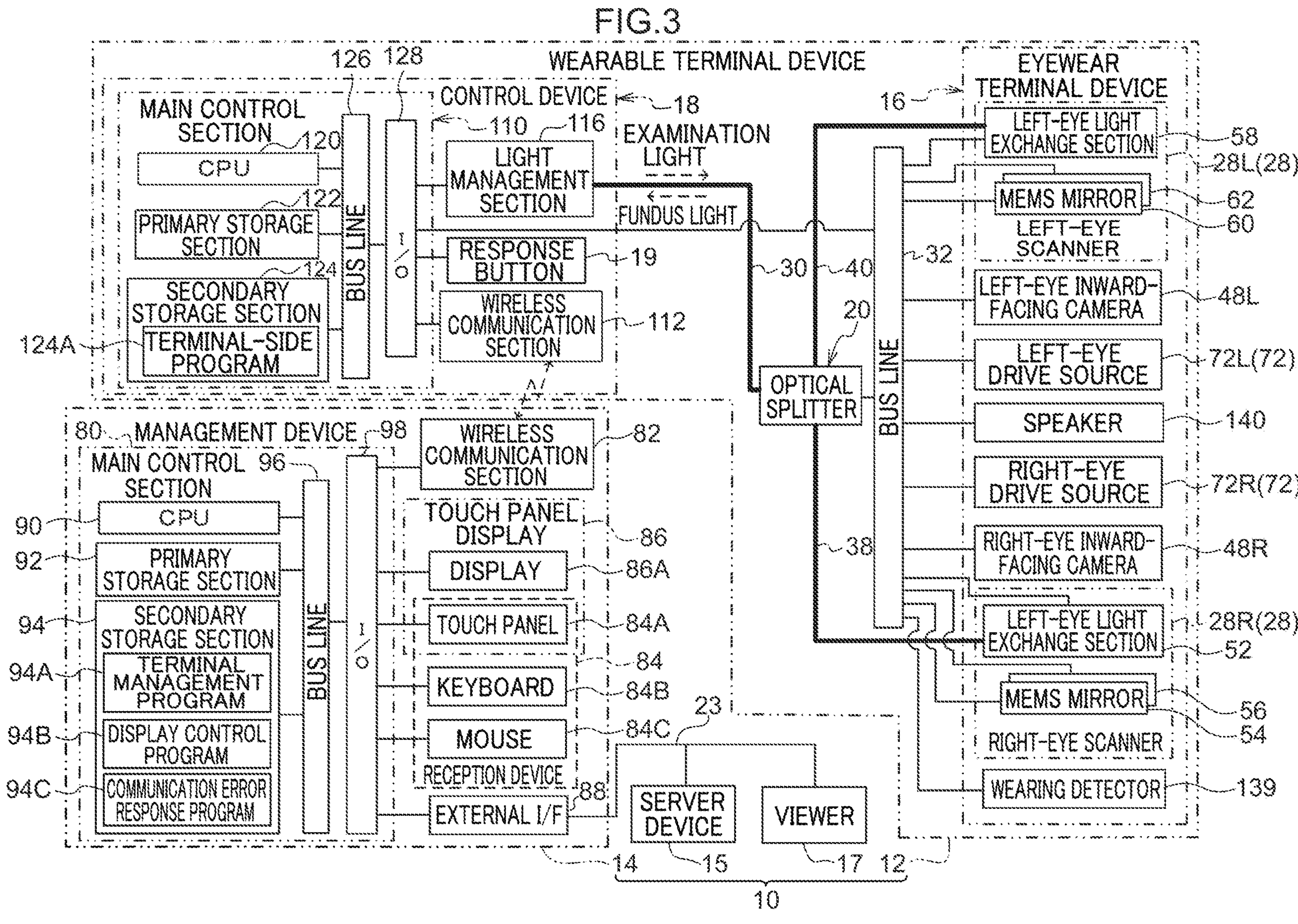
FIG.3
WEARABLE TERMINAL DEVICE
CONTROL DEVICE
MAIN CONTROL SECTION
CPU
PRIMARY STORAGE SECTION
SECONDARY STORAGE SECTION
TERMINAL-SIDE PROGRAM
BUS LINE
I/O
LIGHT MANAGEMENT SECTION
RESPONSE BUTTON
WIRELESS COMMUNICATION SECTION
EXAMINATION LIGHT
FUNDUS LIGHT
OPTICAL SPLITTER
BUS LINE
EYEWEAR TERMINAL DEVICE
LEFT-EYE LIGHT EXCHANGE SECTION
MEMS MIRROR
LEFT-EYE SCANNER
LEFT-EYE INWARD-FACING CAMERA
LEFT-EYE DRIVE SOURCE
SPEAKER
RIGHT-EYE DRIVE SOURCE
RIGHT-EYE INWARD-FACING CAMERA
LEFT-EYE LIGHT EXCHANGE SECTION
MEMS MIRROR
RIGHT-EYE SCANNER
WEARING DETECTOR
MANAGEMENT DEVICE
MAIN CONTROL SECTION
CPU
PRIMARY STORAGE SECTION
SECONDARY STORAGE SECTION
TERMINAL MANAGEMENT PROGRAM
DISPLAY CONTROL PROGRAM
COMMUNICATION ERROR RESPONSE PROGRAM
BUS LINE
I/O
WIRELESS COMMUNICATION SECTION
TOUCH PANEL DISPLAY
DISPLAY
TOUCH PANEL
KEYBOARD
MOUSE
RECEPTION DEVICE
EXTERNAL I/F
SERVER DEVICE
VIEWER
126
128
18
110
116
120
122
124
124A
19
112
30
40
32
20
38
16
58
28L(28)
62
60
48L
72L(72)
140
72R(72)
48R
28R(28)
52
56
54
139
80
98
96
82
90
92
94
94A
94B
94C
86
86A
84A
84
84B
84C
88
23
14
15
17
12
10

FIG.4

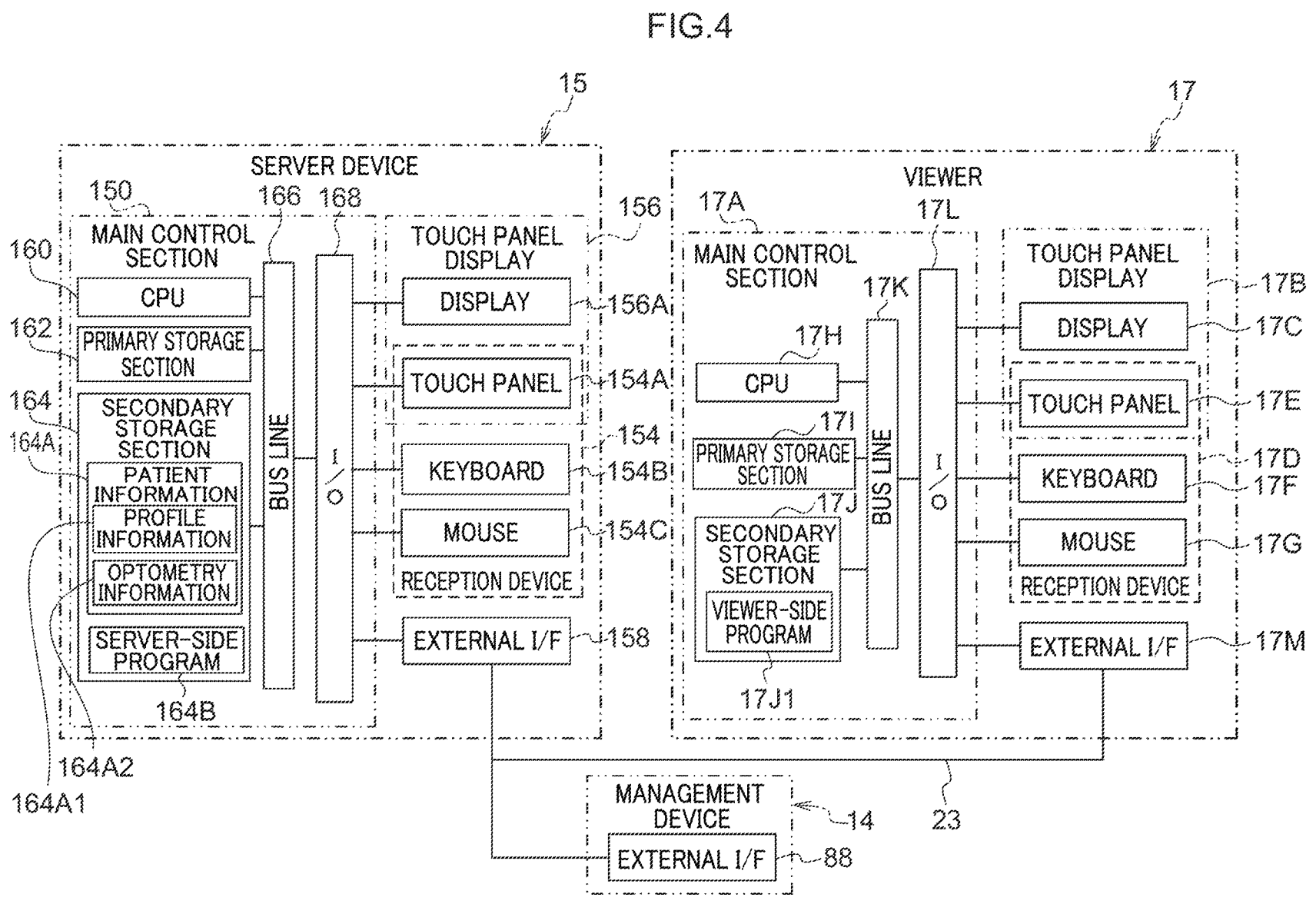

15
SERVER DEVICE
150
MAIN CONTROL SECTION
160
CPU
162
PRIMARY STORAGE SECTION
164
SECONDARY STORAGE SECTION
164A
PATIENT INFORMATION
164A1
PROFILE INFORMATION
164A2
OPTOMETRY INFORMATION
164B
SERVER-SIDE PROGRAM
166
BUS LINE
168
I/O
156
TOUCH PANEL DISPLAY
156A
DISPLAY
154A
TOUCH PANEL
154
154B
KEYBOARD
154C
MOUSE
RECEPTION DEVICE
158
EXTERNAL I/F

17
VIEWER
17A
MAIN CONTROL SECTION
17H
CPU
17I
PRIMARY STORAGE SECTION
17J
SECONDARY STORAGE SECTION
VIEWER-SIDE PROGRAM
17J1
17K
BUS LINE
17L
I/O
17B
TOUCH PANEL DISPLAY
17C
DISPLAY
17E
TOUCH PANEL
17D
17F
KEYBOARD
17G
MOUSE
RECEPTION DEVICE
17M
EXTERNAL I/F

23

14
MANAGEMENT DEVICE
88
EXTERNAL I/F

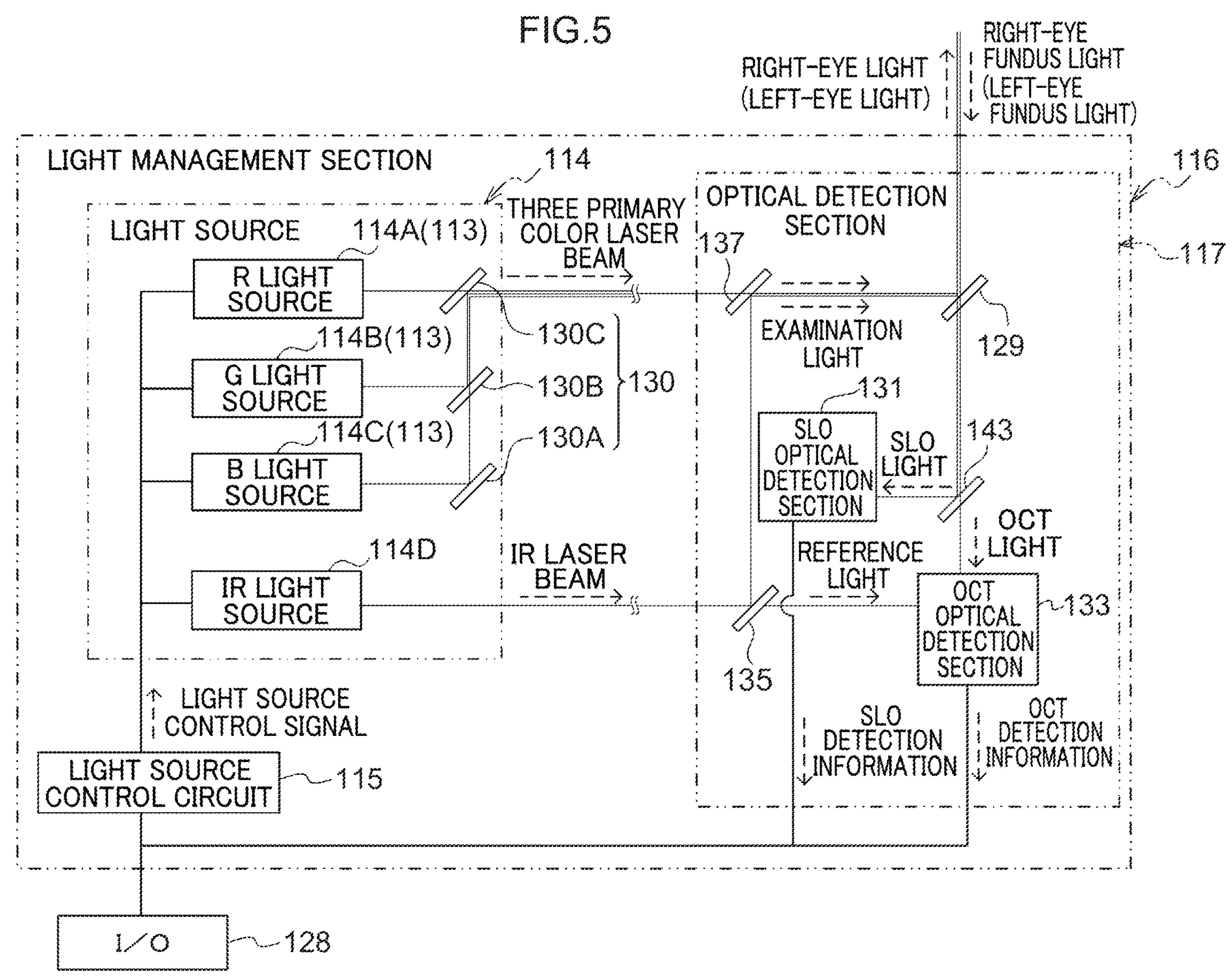
FIG.5
RIGHT-EYE LIGHT (LEFT-EYE LIGHT)
RIGHT-EYE FUNDUS LIGHT (LEFT-EYE FUNDUS LIGHT)
LIGHT MANAGEMENT SECTION
114
116
117
LIGHT SOURCE
114A(113)
R LIGHT SOURCE
114B(113)
G LIGHT SOURCE
114C(113)
B LIGHT SOURCE
114D
IR LIGHT SOURCE
THREE PRIMARY COLOR LASER BEAM
130C
130B
130A
130
IR LASER BEAM
OPTICAL DETECTION SECTION
137
EXAMINATION LIGHT
129
131
SLO OPTICAL DETECTION SECTION
SLO LIGHT
143
OCT LIGHT
REFERENCE LIGHT
OCT OPTICAL DETECTION SECTION
133
135
SLO DETECTION INFORMATION
OCT DETECTION INFORMATION
LIGHT SOURCE CONTROL SIGNAL
LIGHT SOURCE CONTROL CIRCUIT
115
I/O
128

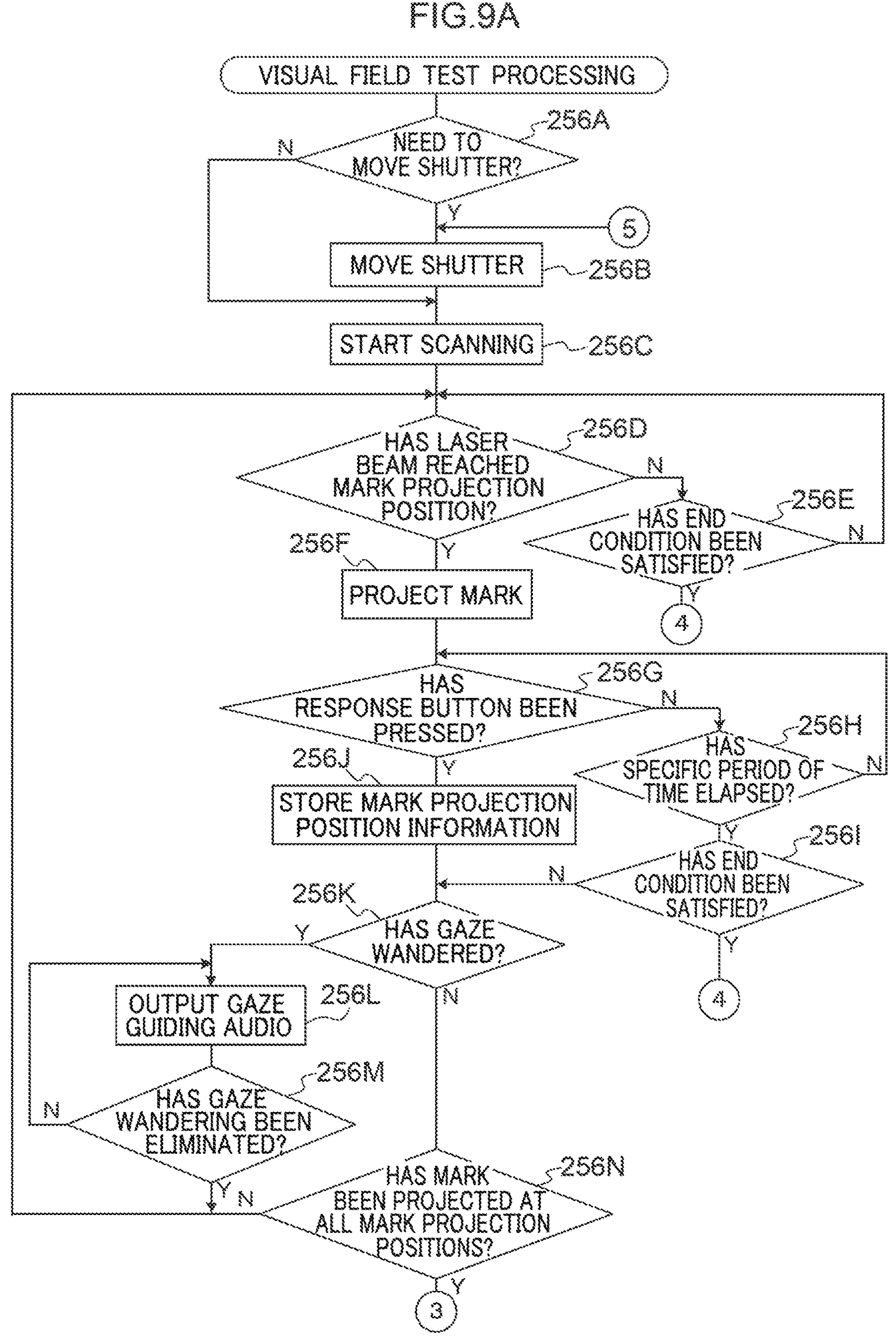
FIG.9A
VISUAL FIELD TEST PROCESSING
NEED TO MOVE SHUTTER?
256A
N
Y
5
MOVE SHUTTER
256B
START SCANNING
256C
HAS LASER BEAM REACHED MARK PROJECTION POSITION?
256D
N
HAS END CONDITION BEEN SATISFIED?
256E
N
Y
4
256F
Y
PROJECT MARK
HAS RESPONSE BUTTON BEEN PRESSED?
256G
N
HAS SPECIFIC PERIOD OF TIME ELAPSED?
256H
N
Y
256J
Y
STORE MARK PROJECTION POSITION INFORMATION
HAS END CONDITION BEEN SATISFIED?
256I
N
Y
4
256K
HAS GAZE WANDERED?
Y
N
OUTPUT GAZE GUIDING AUDIO
256L
HAS GAZE WANDERING BEEN ELIMINATED?
256M
N
Y
N
HAS MARK BEEN PROJECTED AT ALL MARK PROJECTION POSITIONS?
256N
Y
3

3
IS THERE AN EXAMINATION SUBJECT EYE NOT YET SUBJECTED TO VISUAL FIELD TEST?
256R
N
Y
OUTPUT CHANGE NOTIFICATION AUDIO
256S
END SCANNING
256T
5
END SCANNING
256U
(256U1)
GENERATE FIELD-OF-VIEW DEFECT MAP INFORMATION
256V
END

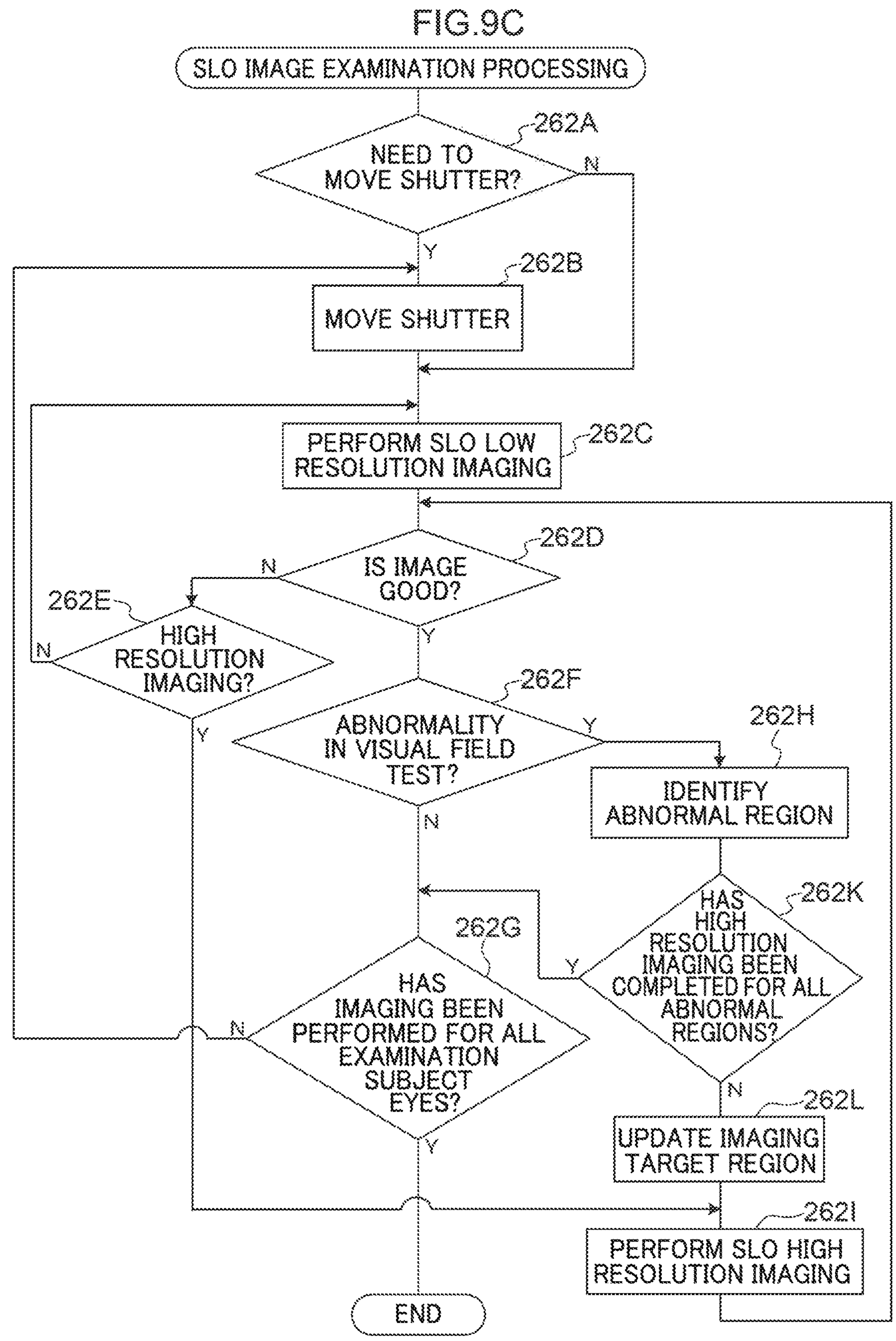
FIG.9C
SLO IMAGE EXAMINATION PROCESSING
NEED TO MOVE SHUTTER?
262A
N
Y
MOVE SHUTTER
262B
PERFORM SLO LOW RESOLUTION IMAGING
262C
IS IMAGE GOOD?
262D
N
Y
HIGH RESOLUTION IMAGING?
262E
N
Y
ABNORMALITY IN VISUAL FIELD TEST?
262F
Y
N
IDENTIFY ABNORMAL REGION
262H
HAS HIGH RESOLUTION IMAGING BEEN COMPLETED FOR ALL ABNORMAL REGIONS?
262K
Y
N
HAS IMAGING BEEN PERFORMED FOR ALL EXAMINATION SUBJECT EYES?
262G
N
Y
UPDATE IMAGING TARGET REGION
262L
PERFORM SLO HIGH RESOLUTION IMAGING
262I
END

FIG.9D

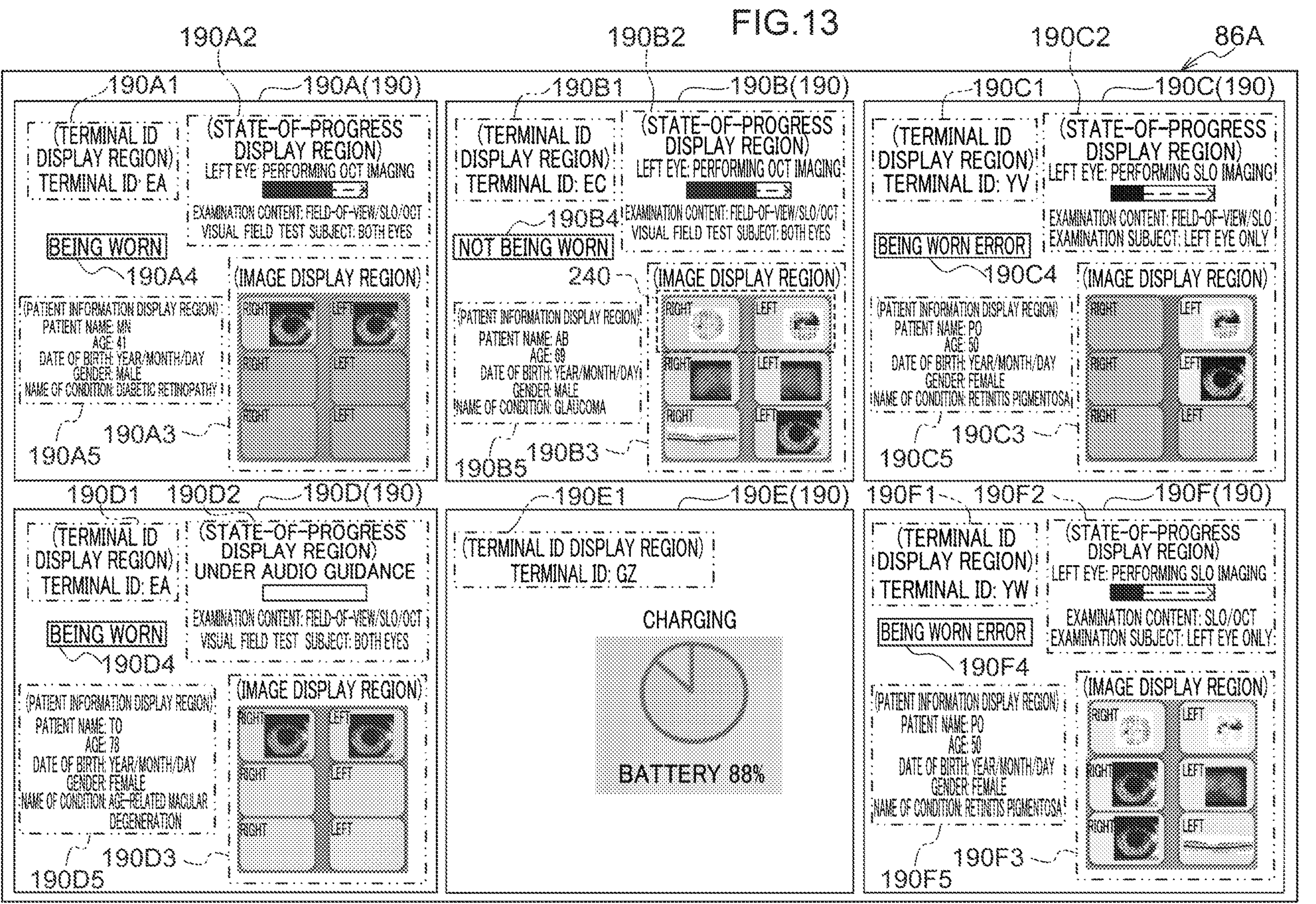
FIG.13
190A2
190B2
190C2
86A
190A1
190A(190)
(TERMINAL ID DISPLAY REGION)
TERMINAL ID: EA
(STATE-OF-PROGRESS DISPLAY REGION)
LEFT EYE: PERFORMING OCT IMAGING
EXAMINATION CONTENT: FIELD-OF-VIEW/SLO/OCT
VISUAL FIELD TEST SUBJECT: BOTH EYES
BEING WORN
190A4
(IMAGE DISPLAY REGION)
RIGHT
LEFT
(PATIENT INFORMATION DISPLAY REGION)
PATIENT NAME: MN
AGE: 41
DATE OF BIRTH: YEAR/MONTH/DAY
GENDER: MALE
NAME OF CONDITION: DIABETIC RETINOPATHY
190A3
190A5
190B1
190B(190)
(TERMINAL ID DISPLAY REGION)
TERMINAL ID: EC
(STATE-OF-PROGRESS DISPLAY REGION)
LEFT EYE: PERFORMING OCT IMAGING
EXAMINATION CONTENT: FIELD-OF-VIEW/SLO/OCT
VISUAL FIELD TEST SUBJECT: BOTH EYES
190B4
NOT BEING WORN
240
(IMAGE DISPLAY REGION)
(PATIENT INFORMATION DISPLAY REGION)
PATIENT NAME: AB
AGE: 69
DATE OF BIRTH: YEAR/MONTH/DAY
GENDER: MALE
NAME OF CONDITION: GLAUCOMA
190B3
190B5
190C1
190C(190)
(TERMINAL ID DISPLAY REGION)
TERMINAL ID: YV
(STATE-OF-PROGRESS DISPLAY REGION)
LEFT EYE: PERFORMING SLO IMAGING
EXAMINATION CONTENT: FIELD-OF-VIEW/SLO
EXAMINATION SUBJECT: LEFT EYE ONLY
BEING WORN ERROR
190C4
(IMAGE DISPLAY REGION)
(PATIENT INFORMATION DISPLAY REGION)
PATIENT NAME: PO
AGE: 50
DATE OF BIRTH: YEAR/MONTH/DAY
GENDER: FEMALE
NAME OF CONDITION: RETINITIS PIGMENTOSA
190C3
190C5
190D1
190D2
190D(190)
(TERMINAL ID DISPLAY REGION)
TERMINAL ID: EA
(STATE-OF-PROGRESS DISPLAY REGION)
UNDER AUDIO GUIDANCE
EXAMINATION CONTENT: FIELD-OF-VIEW/SLO/OCT
VISUAL FIELD TEST SUBJECT: BOTH EYES
BEING WORN
190D4
(IMAGE DISPLAY REGION)
(PATIENT INFORMATION DISPLAY REGION)
PATIENT NAME: TO
AGE: 78
DATE OF BIRTH: YEAR/MONTH/DAY
GENDER: FEMALE
NAME OF CONDITION: AGE-RELATED MACULAR DEGENERATION
190D3
190D5
190E1
190E(190)
(TERMINAL ID DISPLAY REGION)
TERMINAL ID: GZ
CHARGING
BATTERY 88%
190F1
190F2
190F(190)
(TERMINAL ID DISPLAY REGION)
TERMINAL ID: YW
(STATE-OF-PROGRESS DISPLAY REGION)
LEFT EYE: PERFORMING SLO IMAGING
EXAMINATION CONTENT: SLO/OCT
EXAMINATION SUBJECT: LEFT EYE ONLY
BEING WORN ERROR
190F4
(IMAGE DISPLAY REGION)
(PATIENT INFORMATION DISPLAY REGION)
PATIENT NAME: PO
AGE: 50
DATE OF BIRTH: YEAR/MONTH/DAY
GENDER: FEMALE
NAME OF CONDITION: RETINITIS PIGMENTOSA
190F3
190F5

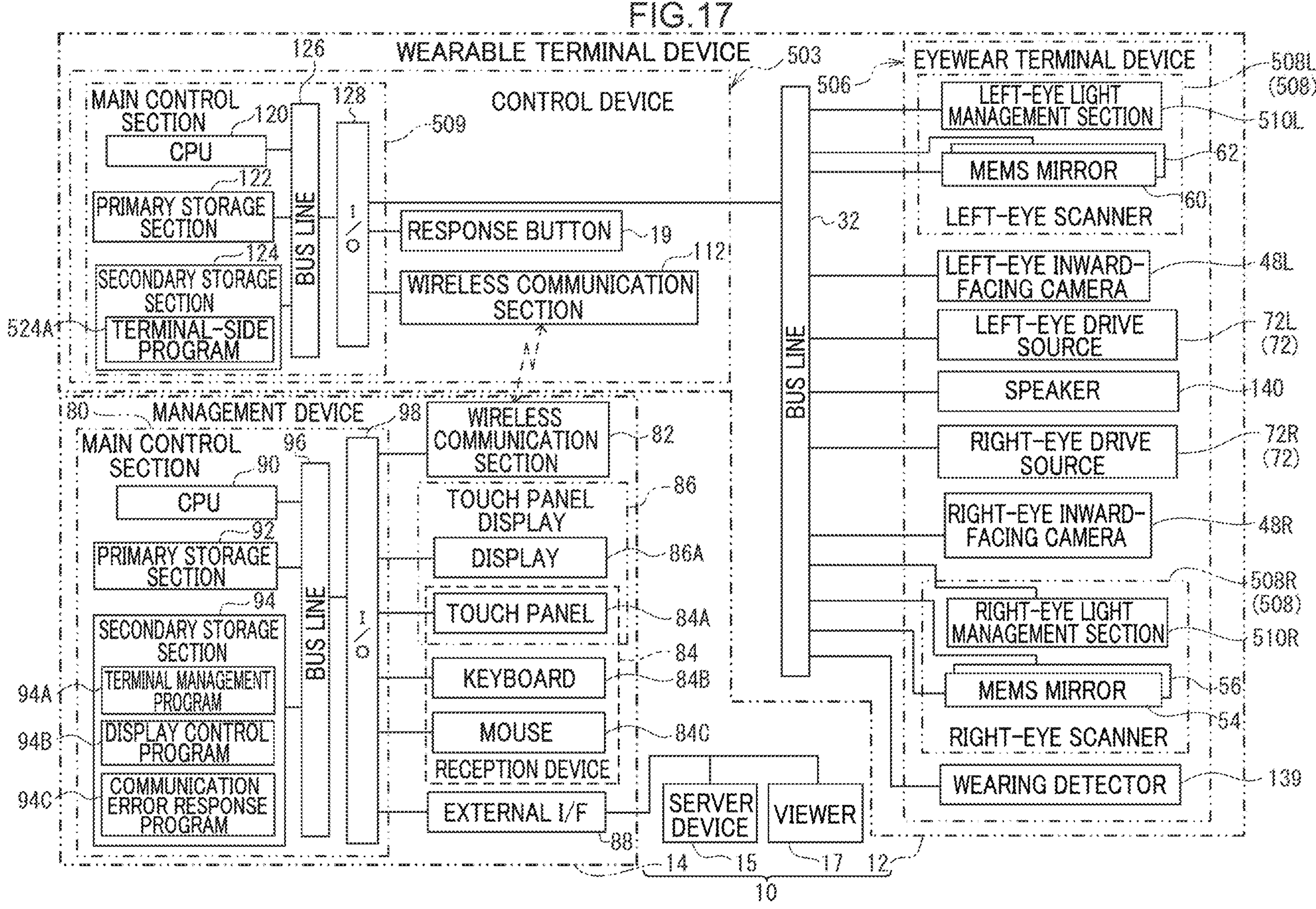
FIG.17
WEARABLE TERMINAL DEVICE
CONTROL DEVICE
MAIN CONTROL SECTION
CPU
PRIMARY STORAGE SECTION
SECONDARY STORAGE SECTION
TERMINAL-SIDE PROGRAM
BUS LINE
I/O
RESPONSE BUTTON
WIRELESS COMMUNICATION SECTION
MANAGEMENT DEVICE
MAIN CONTROL SECTION
CPU
PRIMARY STORAGE SECTION
SECONDARY STORAGE SECTION
TERMINAL MANAGEMENT PROGRAM
DISPLAY CONTROL PROGRAM
COMMUNICATION ERROR RESPONSE PROGRAM
BUS LINE
I/O
WIRELESS COMMUNICATION SECTION
TOUCH PANEL DISPLAY
DISPLAY
TOUCH PANEL
KEYBOARD
MOUSE
RECEPTION DEVICE
EXTERNAL I/F
SERVER DEVICE
VIEWER
BUS LINE
EYEWEAR TERMINAL DEVICE
LEFT-EYE LIGHT MANAGEMENT SECTION
MEMS MIRROR
LEFT-EYE SCANNER
LEFT-EYE INWARD-FACING CAMERA
LEFT-EYE DRIVE SOURCE
SPEAKER
RIGHT-EYE DRIVE SOURCE
RIGHT-EYE INWARD-FACING CAMERA
RIGHT-EYE LIGHT MANAGEMENT SECTION
MEMS MIRROR
RIGHT-EYE SCANNER
WEARING DETECTOR
126
128
120
509
122
124
524A
19
112
80
98
96
90
92
94
94A
94B
94C
82
86
86A
84A
84
84B
84C
88
14
15
17
12
10
503
506
32
508L (508)
510L
62
60
48L
72L (72)
140
72R (72)
48R
508R (508)
510R
56
54
139

FIG.19A

800
OPHTHALMIC SYSTEM
812
17
15
14
140
24L1
24R1
24
24R 24L
LEFT
RIGHT
48R
48L
42
42R 42L
16
22
27
36A
30B
32
α
34A
30A
25A
916
819
818

FIG.24

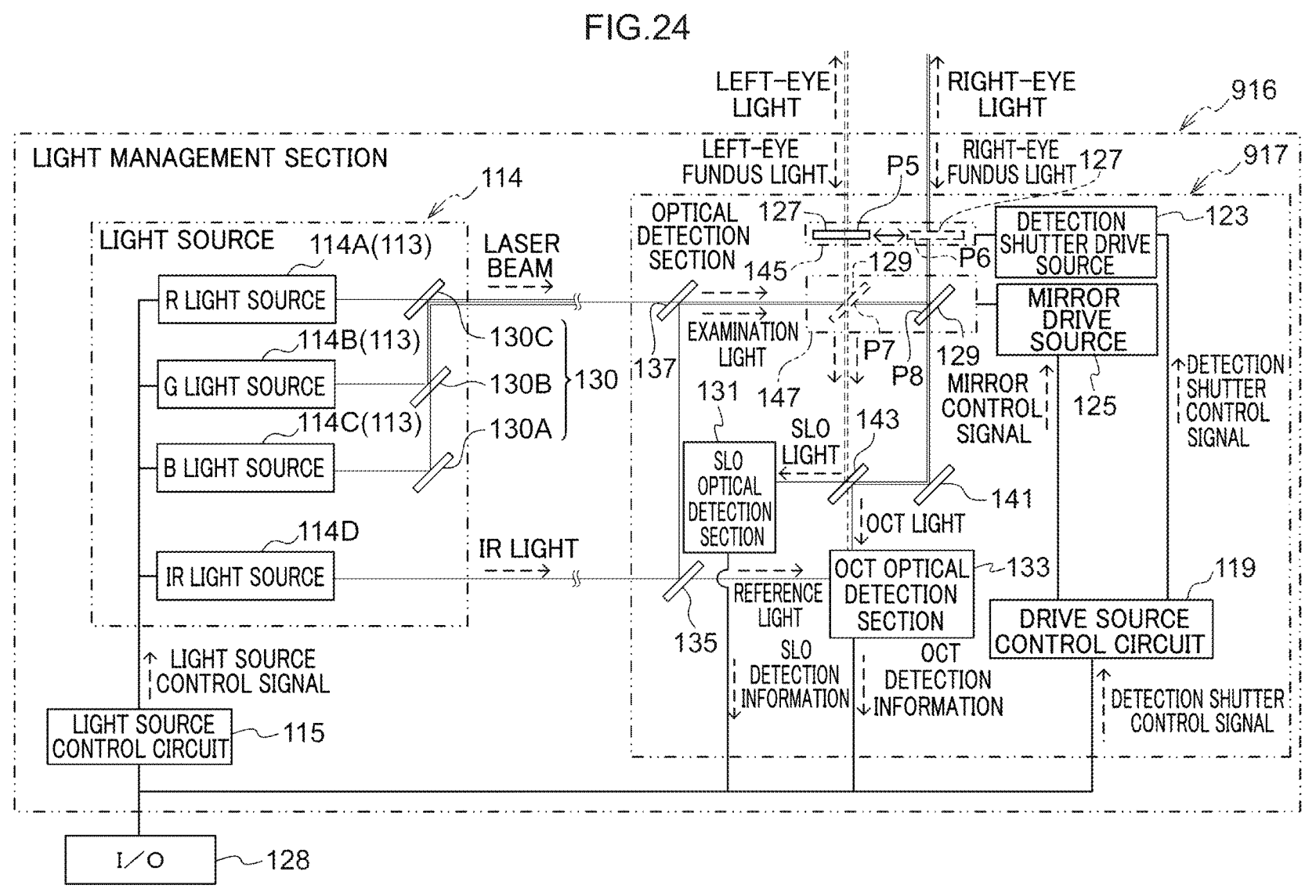

LIGHT MANAGEMENT SECTION
916
917
114
LIGHT SOURCE
R LIGHT SOURCE
114A(113)
G LIGHT SOURCE
114B(113)
B LIGHT SOURCE
114C(113)
IR LIGHT SOURCE
114D
130C
130B
130A
130
LASER BEAM
IR LIGHT
LIGHT SOURCE CONTROL SIGNAL
LIGHT SOURCE CONTROL CIRCUIT
115
I/O
128
LEFT-EYE LIGHT
LEFT-EYE FUNDUS LIGHT
RIGHT-EYE LIGHT
RIGHT-EYE FUNDUS LIGHT
OPTICAL DETECTION SECTION
127
127
145
147
137
EXAMINATION LIGHT
131
SLO OPTICAL DETECTION SECTION
135
SLO LIGHT
REFERENCE LIGHT
SLO DETECTION INFORMATION
143
OCT LIGHT
141
OCT OPTICAL DETECTION SECTION
133
OCT DETECTION INFORMATION
P5
P6
P7
P8
129
129
129
DETECTION SHUTTER DRIVE SOURCE
123
MIRROR DRIVE SOURCE
125
MIRROR CONTROL SIGNAL
DETECTION SHUTTER CONTROL SIGNAL
DRIVE SOURCE CONTROL CIRCUIT
119
DETECTION SHUTTER CONTROL SIGNAL

OPHTHALMIC INSTRUMENT, MANAGEMENT METHOD, AND MANAGEMENT DEVICE

CROSS-REFERENCE TO RELATED APPLICATIONS

This application is a continuation of U.S. application Ser. No. 16/645,328, filed on Mar. 6, 2020, which is a 371 U.S. National Application of International Application No. PCT/JP2018/033719. filed on Sep. 11, 2018, which claims the benefit of and priority to Japanese Application No. 2017-173945, filed on Sep. 11, 2017, each of the foregoing are incorporated by reference herein in their entireties.

TECHNICAL FIELD

The technology disclosed herein relates to an ophthalmic instrument, a management method, and a management device.

BACKGROUND ART

In the present specification ophthalmology indicates the field of medicine that handles eyes. In the present specification SLO is employed as an abbreviation to indicate a scanning laser ophthalmoscope. In the present specification OCT is employed as an abbreviation to indicate optical coherence tomography.

Japanese Patent Application Laid-Open (JP-A) No. 2016-22150 discloses a visual function examination device including an illumination optical system, a biometric information detection section, an evaluation information generation section, and a control section.

The illumination light optical system in the visual function examination device described in JP-A No. 2016-22150 includes an optical scanner disposed on the optical path of a laser beam output from a laser light source, and the laser beam that has passed through the optical scanner is shone onto the retina of a subject eye. Moreover, the biometric information detection section repetitively detects biometric information expressing the reaction of a subject to illumination by the laser beam. Moreover, the control section controls the illumination optical system such that an illumination intensity of the laser beam onto a single stimulation point on the retina is changed monotonously while repetitively detecting the biometric information.

The evaluation information generation section in the visual function examination device described in JP-A No. 2016-22150 generates evaluation information related to the visual function of the subject eye based on the biometric information as detected. More specifically, the evaluation information generation section generates information regarding the sensitivity at a single stimulation point based on changes in the time series of the biometric information in response to the monotonous changes in the illumination intensity of the laser beam. Moreover, the evaluation information generation section generates as evaluation information a distribution of sensitivity information for plural stimulation points on the retina based on the sensitivity information generated for each of the plural stimulation points.

SUMMARY OF INVENTION

An ophthalmic instrument according to a first aspect of technology disclosed herein includes: an light emitter configured to emit light from a light source, the light source including a first light source unit and a second light source unit that emit light for examining a subject eye; an optical system including a right-eye optical system configured to guide light emitted from the light emitter onto a right-eye retina, and a left-eye optical system configured to guide light emitted from the light emitter onto a left-eye retina; and a control section configured to control the light emitter and the optical system such that the light is shone onto the right-eye retina and/or onto the left-eye retina.

An ophthalmic instrument according to a second aspect of technology disclosed herein includes: a light management section that includes a light source including a first light source unit and a second light source unit that emit light for examining a subject eye; an eyewear terminal that includes an optical system including a right-eye optical system configured to guide the light onto a right-eye retina and a left-eye optical system configured to guide the light onto a left-eye retina; an optical splitter to guide the light from the light management section into the right-eye optical system and/or the left-eye optical system; and a control section configured to control the light management section, the optical system, and the optical splitter.

An ophthalmic instrument according to a third aspect of technology disclosed herein includes: a right-eye light emitter configured to emit right-eye examination light; a left-eye light emitter configured to emit left-eye examination light; an optical system including a right-eye optical system configured to guide the right-eye examination light onto a right-eye retina and a left-eye optical system configured to guide the left-eye examination light onto a left-eye retina; and a control section configured to control the right-eye light emitter, the left-eye light emitter, and the optical system such that the right-eye examination light is shone onto the right-eye retina and the left-eye examination light is shone onto the left-eye retina.

A management method according to a fourth aspect of technology disclosed herein is a management method to manage an ophthalmic instrument including an light emitter configured to emit light from a light source, the light source including a first light source unit and a second light source unit that emit light for examining a subject eye, an optical system including a right-eye optical system configured to guide light emitted from the light emitter onto a right-eye retina, and a left-eye optical system configured to guide light emitted from the light emitter onto a left-eye retina, and a control section configured to control the light emitter and the optical system such that the light is shone onto the right-eye retina and/or onto the left-eye retina. The management method includes: transmitting to the ophthalmic instrument ophthalmic examination information including instruction information to instruct an examination subject eye and examination type identification information to identify a type of an ophthalmic examination; and acquiring from the ophthalmic instrument examination result information representing a result of the examination by the ophthalmic instrument.

A management device according to a fifth aspect of technology disclosed herein is a management device equipped with a communication section to perform data exchange with the ophthalmic instrument of the first aspect of technology disclosed herein, and a control section. The control section transmits to the ophthalmic instrument ophthalmic examination information including instruction information to instruct an examination subject eye and examination type identification information to identify a type of an ophthalmic examination; and acquires from the ophthalmic instrument examination result information representing a result of the examination by the ophthalmic instrument.

BRIEF DESCRIPTION OF DRAWINGS

FIG. 3 is a block diagram illustrating an example of a hardware configuration of an electrical system of a wearable terminal device and a management device included in an ophthalmic system according to the first exemplary embodiment.

FIG. 4 is a block diagram illustrating an example of a hardware configuration of an electrical system of a server device and a viewer included in an ophthalmic system according to the first exemplary embodiment and a second exemplary embodiment.

FIG. 5 is a schematic configuration diagram illustrating an example of a configuration of a light management section included in a wearable terminal device of an ophthalmic system according to the first exemplary embodiment.

FIG. 9A is a flowchart illustrating an example of flow in visual field test processing included in terminal-side processing according to the first exemplary embodiment.

FIG. 9C is a flowchart illustrating an example of flow in SLO image detection processing included in terminal-side processing according to the first exemplary embodiment.

FIG. 9D is a flowchart illustrating an example of a flow in OCT image detection processing included in terminal-side processing according to the first exemplary embodiment.

FIG. 13 is a schematic screen layout illustrating an example of a situation in which a state-of-progress screen is displayed on a display by execution of display control processing according to the first to third exemplary embodiments.

FIG. 17 is a block diagram illustrating an example of a hardware configuration of an electrical system of a wearable terminal device and a management device included in an ophthalmic system according to the second exemplary embodiment.

FIG. 19A is a flowchart illustrating an example of a flow of visual field test processing included in terminal-side processing according to the second exemplary embodiment.

FIG. 24 is a schematic diagram illustrating an example of a configuration of a light management section included in a wearable terminal device of an ophthalmic system according to the third exemplary embodiment

DESCRIPTION OF EMBODIMENTS

Explanation follows regarding examples of exemplary embodiments according to technology disclosed herein, with reference to the drawings.

First, explanation will be given regarding the meaning of the terms employed in the following description. In the following description MEMS is employed as an abbreviation to indicate micro electro mechanical systems. In the following description OF is employed as an abbreviation to indicate an interface. In the following description I/O is employed as an abbreviation to indicate an input/output interface. In the following description USB is employed as an abbreviation to indicate a universal serial bus. In the following description ID is employed as an abbreviation to indicate identification.

In the following description CPU is employed as an abbreviation to indicate central processing unit. In the following description RAM is employed as an abbreviation to indicate random access memory. In the following description HDD is employed as an abbreviation to indicate a hard disk drive. In the following description EEPROM is employed as an abbreviation to indicate electrically erasable programmable read only memory. In the following description SSD is employed as an abbreviation to indicate a solid state drive. In the following description DVD-ROM is employed as an abbreviation to indicate digital versatile disk read only memory.

In the following description ASIC is employed as an abbreviation to indicate an application specific integrated circuit. In the following description FPGA is employed as an abbreviation to indicate a field programmable gate array. In the following description PLD is employed as an abbreviation to indicate a programmable logic device. In the following description LAN is employed as an abbreviation to indicate a local area network.

Moreover, in the present exemplary embodiments, the left and right directions indicate, for example, directions of a straight line passing through the center of the pupil of the right eye of a patient and through the center of the pupil of the left eye of the patient. Note that in the following, for ease of explanation, the "left and right directions" are referred to as the "X direction", a direction from the center of the pupil of a subject eye toward the rear pole of the subject eye is referred to as the "Z direction", and a direction perpendicular to both the X direction and the Z direction is referred to as the "Y direction".

First Exemplary Embodiment

Figure 1:
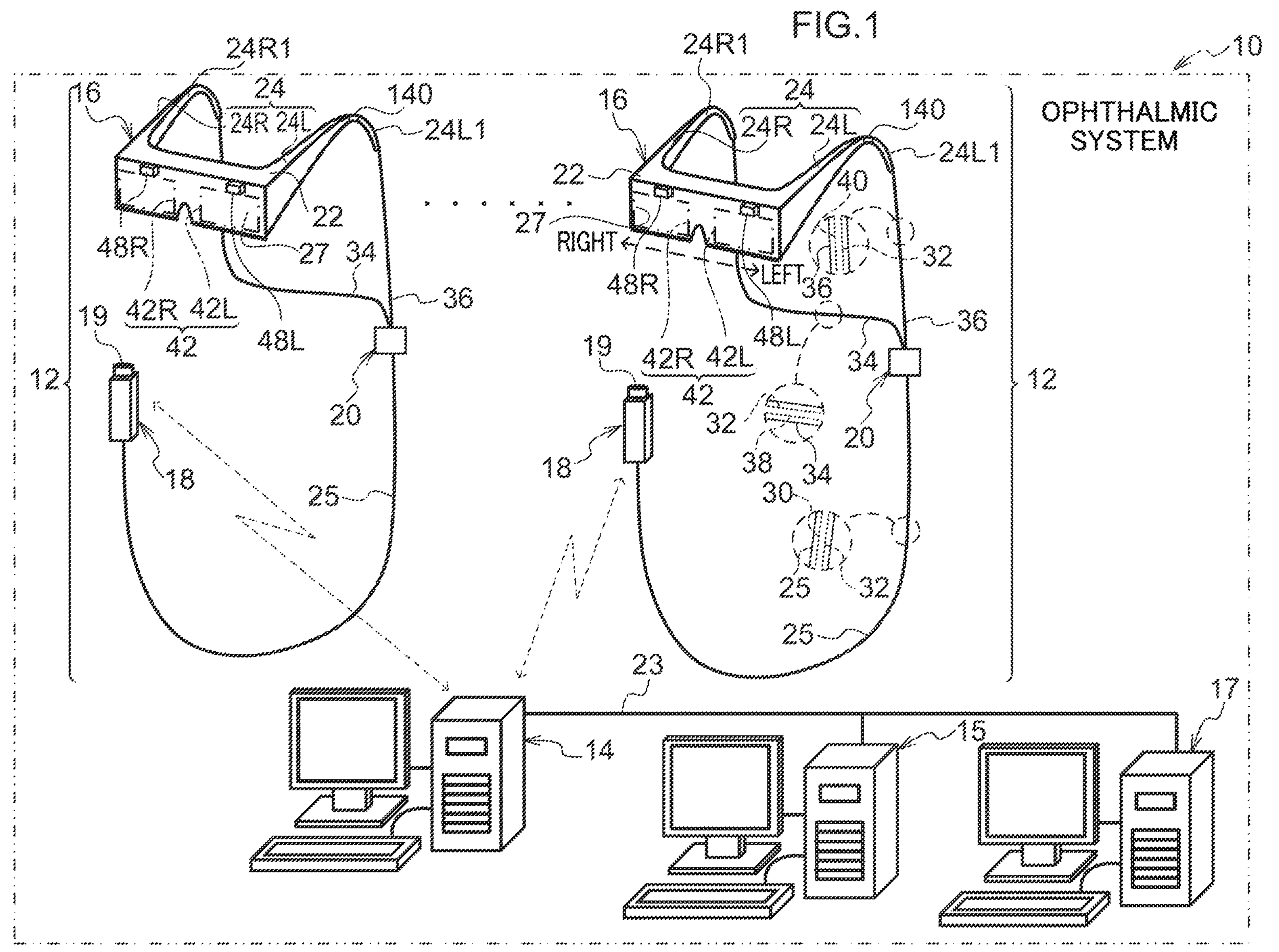
FIG. 1 is a schematic diagram illustrating an example of an overall configuration of an ophthalmic system according to a first exemplary embodiment.

As illustrated for example in FIG. 1, an ophthalmic system 10 is a system to examine the ophthalmic system of a patient, namely, an examination of a subject eye 44 (see FIG. 2) (hereafter referred simply referred to as performing an "ophthalmic examination"). The ophthalmic examinations of the present exemplary embodiment include visual field tests and image examinations. A visual field test indicates an examination of the field of view of a patient (subject). An image examination indicates an examination using a fundus image obtained by imaging the fundus of a patient (subject). The image examinations include both SLO image examinations using an SLO image obtained by plan view imaging of a retina 46 (see FIG. 2) of a subject eye 44 (see FIG. 2) using SLO, and OCT image examinations using an OCT image obtained by tomographic imaging of the retina 46 using OCT.

Plan view imaging indicates imaging to obtain a plan view image of the retina 46 by scanning a three primary color laser beam composed of laser beams of three primary colors of R (red), G (green), and B (blue) onto the retina 46 in a two-dimensional pattern. In the present exemplary embodiment an example is explained in which a three primary color laser beam is employed, however, the technology disclosed herein is not limited thereto, and, for example, a configuration may be adopted that employs a laser beam of a single color or a laser beam of two colors selected from out of R, G, or B. Tomographic imaging indicates imaging to obtain a tomographic image of the retina 46 by scanning a laser beam of near infrared light (hereafter referred to as an IR laser beam) onto the retina. Note that in the present specification "IR" means "near-infrared".

Note that the three primary color laser beam is an example of "light for examining a subject eye" and of "light from an SLO light source" according to technology disclosed herein. Moreover, the IR laser beam is an example of "light for examining a subject eye" and of "light from an OCT light source" according to technology disclosed herein. When there is no need to discriminate in the description below between the "three primary color laser beam" and the "IR laser beam", for ease of explanation they will be referred to as "examination light". Although for ease of explanation the IR laser beam is employed for OCT image examination below, the technology disclosed herein is not limited thereto, and the IR laser beam may also be employed for SLO image examination.

The ophthalmic system 10 includes plural wearable terminal devices 12, a management device 14, a server device 15, and a viewer 17. Note that the wearable terminal device 12 is an example of an ophthalmic instrument according to technology disclosed herein.

Each of the wearable terminal devices 12 includes an eyewear terminal device 16 as an example of an eyewear terminal device according to technology disclosed herein, a control device 18, and an optical splitter 20.

The eyewear terminal device 16 is one sort of glasses-type terminal device worn by a patient. Reference here to "patient" indicates a patient having a condition of the fundus. Note that a patient is an example of a subject according to technology disclosed herein.

Similarly to ordinary glasses, the eyewear terminal device 16 includes a rim piece 22 and a temple piece 24. The eyewear terminal device 16 also includes an optical system 27.

The rim piece 22 holds the optical system 27. The temple piece 24 is broadly divided into a left temple piece 24L and a right temple piece 24R. One end portion of the left temple piece 24L is attached to a left end portion of the rim piece 22, and the right temple piece 24R is attached to the right end portion of the rim piece 22.

The left temple piece 24L includes an ear hook 24L1. The right temple piece 24R includes an ear hook 24R1. The ear hook 24L1 hooks onto the left ear of the patient, and the ear hook 24R1 hooks onto the right ear of the patient.

A speaker 140 is provided on the ear hook 24L1. The speaker 140 outputs audio under control from the control device 18. The speaker 140 may be a speaker that directly imparts a sound wave to the eardrum of the patient, or may be a bone conduction speaker that indirectly transmits vibrations to the ear of the patient. The speaker 140 is an example of a notification section to notify information to the patient by activating the hearing of the patient.

The control device 18 is, for example, employed by being grasped by the patient, or by being worn by the patient on their clothes or on their person. The control device 18 is equipped with a response button 19. The response button 19 is an example of a reception section (response section) according to technology disclosed herein. The response button 19 referred to here is merely an example thereof, and the technology disclosed herein is not limited thereto. For example, a touch panel may be employed instead of the response button 19, or a microphone may be employed to pick up speech of a patient in response to the patient sensing the laser beam and a speech recognition device may be employed to recognize the audio picked up by the microphone. In such cases the touch panel and the speech recognition device output response information, described later, in response to activation by the patient.

The response button 19 is operated by the patient and outputs information according to operation by the patient. The response button 19 receives an operation as to whether or not the patient has sensed the three primary color laser beam when the three primary color laser beam was shone onto a retina 46 (see FIG. 2) of a subject eye 44 (see FIG. 2). In other words, the response button 19 receives operation by the patient in cases in which the patient responds to having sensed the laser beam. Namely, processing is performed to associate the response information of the response button with mark projection position information.

The response button 19 is also sometimes pressed by the patient when the patient responds to a question from a medical service professional. Note that reference here to a "medical service professional" indicates, for example, a medical technician in ophthalmology with the qualifications of an orthoptist who performs vision examinations under instruction from an ophthalmologist. The response button 19 and the control device 18 are connected together so as to enable either wired and/or wireless communication therebetween, and response information arising from operation of the response button 19 is transmitted to the control device 18. One response button 19 is associated with the control device 18 by a number, such as a machine number. Examples of wireless communication include communication by Wi-Fi (registered trademark), Bluetooth (registered trademark), or the like. Examples of wired communication include communication using a cable.

The control device 18 is connected to the management device 14 in a state capable of wireless communication therewith, and the control device 18 exchanges various kinds of information with the management device 14. The control device 18 is connected to the optical splitter 20 by a cable 25 and controls the optical splitter 20. The control device 18 may also be connected to the management device 14 in a state capable of wireless communication therewith.

The cable 25 includes an optical fiber 30 and a bus line 32. The control device 18 supplies examination light to the optical splitter 20 through the optical fiber 30 and controls the optical splitter 20 through the bus line 32.

The optical system 27 is equipped with the optical splitter 20. The optical splitter 20 is connected to the eyewear terminal device 16 by cables 34, 36. The cable 34 is connected to the right temple piece 24R, and the cable 36 is connected to the left temple piece 24L. The cables 34, 36 both include the bus line 32. Thus the control device 18 exchanges various kinds of electrical signal with the eyewear terminal device 16 through the bus line 32.

The cable 34 includes an optical fiber 38, and the cable 36 includes an optical fiber 40. The optical splitter 20 splits the examination light supplied from the control device 18 through the optical fiber 30 so that examination light passes into the optical fiber 38 and/or into the optical fiber 40. One moiety of examination light obtained by splitting with the optical splitter 20 is supplied into the eyewear terminal device 16 through the optical fiber 38. Another moiety of examination light obtained by splitting with the optical splitter 20 is supplied into the eyewear terminal device 16 through the optical fiber 40.

The optical system 27 is equipped with a reflection minor 42. The reflection mirror 42 is an example of a reflection member according to technology disclosed herein. The reflection mirror 42 guides examination light onto the retinas 46 of the subject eyes 44 of the patient by reflecting the examination light supplied from the optical splitter 20 through the cables 34, 36, as illustrated for example in FIG. 2. Note that the subject eyes 44 are broadly composed of a right eye 44R and a left eye 44L, as illustrated for example in FIG. 2. The retinas 46 are broadly composed of a retina 46R that is an example of a right retina according to technology disclosed herein, and a retina 46L that is an example of a left retina according to technology disclosed herein.

The reflection mirrors 42 are broadly composed of a right-eye reflection mirror 42R and a left-eye reflection minor 42L. The right-eye reflection mirror 42R is held by the rim piece 22 so as to be positioned in front of the right eye 44R of the patient when the eyewear terminal device 16 is in a correctly worn state. The left-eye reflection mirror 42L is held by the rim piece 22 so as to be positioned in front of the left eye 44L of the patient when the eyewear terminal device 16 is in a correctly worn state.

Figure 2:
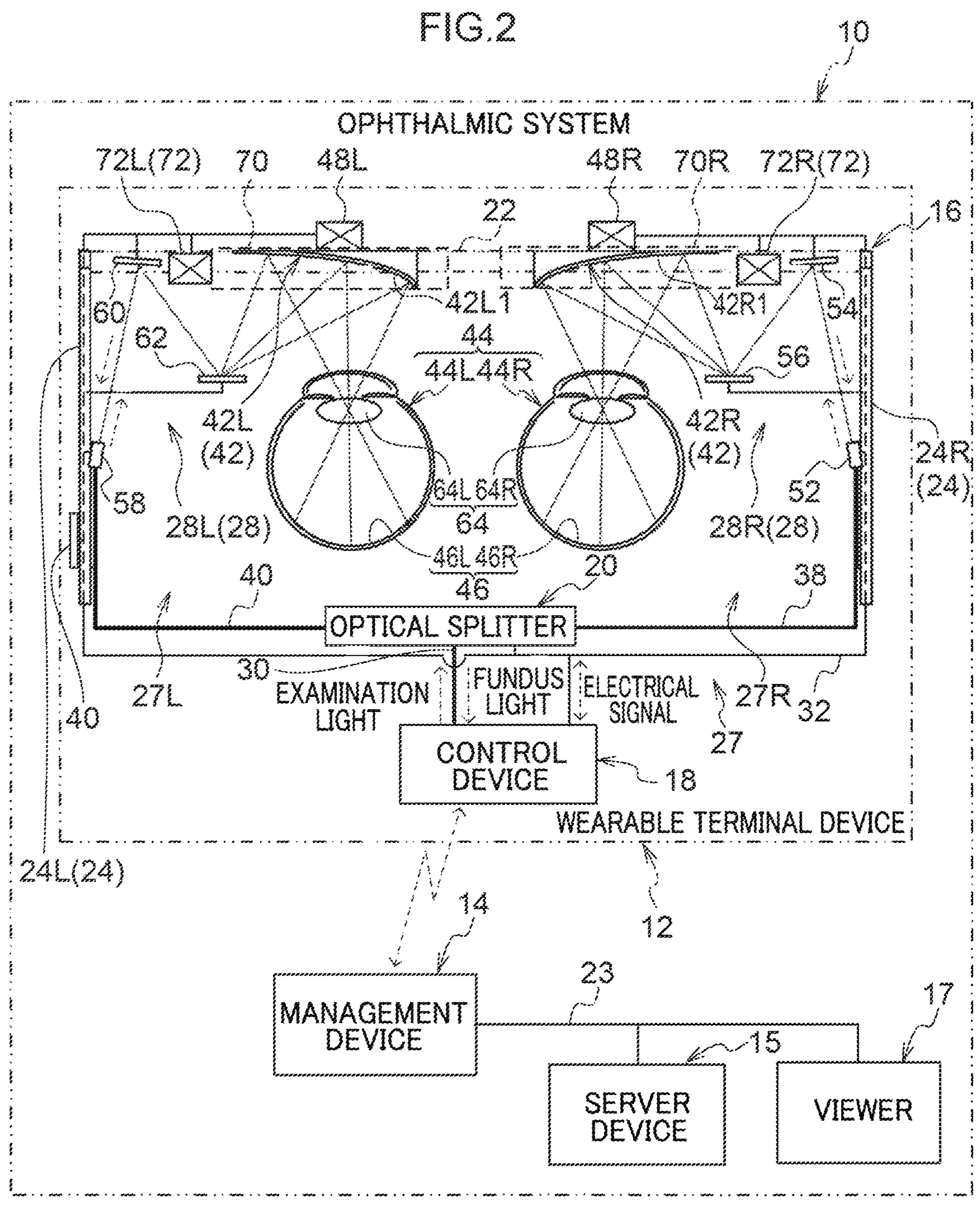
FIG. 2 is a schematic plan view configuration diagram illustrating an example of a configuration of a wearable terminal device included in an ophthalmic system according to the first exemplary embodiment.

The right-eye reflection mirror 42R guides examination light onto the retina 46R of the right eye 44R of the patient by reflecting the examination light supplied from the optical splitter 20 through the optical fiber 38, as illustrated for example in FIG. 2. The left-eye reflection mirror 42L guides examination light onto the retina 46L of the left eye 44L of the patient by reflecting the examination light supplied from the optical splitter 20 through the optical fiber 40, as illustrated for example in FIG. 2.

The eyewear terminal device 16 is equipped with a right-eye inward-facing camera 48R and a left-eye inward-facing camera 48L. The right-eye inward-facing camera 48R and the left-eye inward-facing camera 48L image an imaging subject under control from the control device 18.

The right-eye inward-facing camera 48R and the left-eye inward-facing camera 48L are attached to an upper edge of the rim piece 22. The right-eye inward-facing camera 48R is provided at a position shifted away from the right-eye reflection mirror 42R in the Y direction, and images the anterior segment of the right eye 44R as an imaging subject from diagonally above a region in front of the right eye 44R. The left-eye inward-facing camera 48L is provided at a position shifted away from the left-eye reflection mirror 42L in the Y direction, and images the anterior segment of the left eye 44L as an imaging subject from diagonally above a region in front of the left eye 44L. The right-eye inward-facing camera 48R and the left-eye inward-facing camera 48L are examples of anterior segment cameras according to technology disclosed herein. Moreover, although the right-eye inward-facing camera 48R and the left-eye inward-facing camera 48L are given as examples here, the technology disclosed herein is not limited thereto. For example, instead employing the right-eye inward-facing camera 48R and the left-eye inward-facing camera 48L, a single camera may be employed to image both the anterior segment of the right eye 44R and the anterior segment of the left eye 44L.

The management device 14 performs unified management of ophthalmic examinations performed by each of the plural wearable terminal devices 12. The ophthalmic examinations by the wearable terminal devices 12 referred to here are, in other words, ophthalmic examinations being performed using the wearable terminal devices 12. Management of the ophthalmic examinations referred to here indicates, for example, management such as management of the examination light employed in ophthalmic examination, management of sensing information expressing visual sensing by the patients of the illuminated three primary color laser beam achieved by shining the three primary color laser beam onto the retinas 46, management of communication with the wearable terminal devices 12, and management of ascertaining for each of the wearable terminal devices 12 a state-of-progress of ophthalmic examination with each of the wearable terminal devices 12 and displaying a state-of-progress screen 190 thereof, described later.

The control device 18 supplies examination light into the eyewear terminal device 16 through the optical fibers 30, 38, 40 under instruction from the management device 14.

Note that although explanation has been given in the present exemplary embodiment of an example in which wireless communication is performed between the wearable terminal devices 12 and the management device 14, technology disclosed herein is not limited thereto. For example, wired communication may be performed between the wearable terminal devices 12 and the management device 14.

The server device 15 provides information and/or performs information processing in response to requests from external devices such as from the management device 14 and/or the viewer 17 etc., and performs unified management of personal information of plural patients. The server device 15 is connected to the management device 14 and the viewer 17 through a cable 23 and exchanges various kinds of information with the management device 14 and the viewer 17. An example of the cable 23 is a LAN cable. Note that although wired communication is performed between the server device 15 and the management device 14 in the present exemplary embodiment, technology disclosed herein is not limited thereto, and wireless communication may be performed between the server device 15 and the management device 14.

The optical system 27 guides the examination light onto the retina 46R and/or the retina 46L, as illustrated for example in FIG. 2. The optical system 27 includes a scanner 28 and the reflection mirror 42. The scanner 28 scans examination light supplied from the control device 18 through the optical splitter 20. The reflection mirror 42 reflects the examination light being scanned by the scanner 28 onto the retinas 46.

The optical system 27 includes a right-eye optical system 27R and a left-eye optical system 27L. The optical splitter 20 splits the examination light supplied from the control device 18 through the optical fiber 30 so as to pass into the right-eye optical system 27R and the left-eye optical system 27L.

The right-eye optical system 27R guides the examination light being supplied from the optical splitter 20 through the optical fiber 38 onto the retina 46R. The left-eye optical system 27L guides the examination light being supplied from the optical splitter 20 through the optical fiber 40 onto the retina 46L.

The scanner 28 includes a right-eye scanner 28R and a left-eye scanner 28L. The right-eye optical system 27R includes the right-eye scanner 28R and the right-eye reflection mirror 42R. The left-eye optical system 27L includes the left-eye scanner 28L and the left-eye reflection mirror 42L.

The right-eye scanner 28R includes MEMS mirrors 54, 56, and scans the laser beam supplied through a right-eye light exchange section 52. The right-eye light exchange section 52 shines a laser beam supplied from the laser optical splitter 20 through the optical fiber 38. The MEMS mirror 54 is disposed on the direction the laser beam is shone in by the right-eye light exchange section 52, and the MEMS mirror 54 reflects the laser beam being shone from the right-eye light exchange section 52 so as to be guided onto the MEMS minor 56. The MEMS minor 56 reflects the laser beam guided by the MEMS mirror 54 so as to be guided onto the right-eye reflection mirror 42R.

For example, the MEMS minor 54 scans the laser beam in the Y direction, and the MEMS minor 56 scans the laser beam in the X direction. Two-dimensional scanning on the retina is enabled by the MEMS minors 54, 56, enabling a picture to be two-dimensionally scanned and projected onto the retina.

Obviously a configuration may be adopted in which the MEMS mirror 54 scans in the X direction and the MEMS mirror 56 scans in the Y direction.

Furthermore, the right-eye scanner 28R may be configured by employing the reflection mirror 42R and a MEMS mirror 56 capable of scanning in the XY directions.

The right-eye reflection mirror 42R reflects the examination light scanned by the right-eye scanner 28R onto the retina 46R.

The right-eye light exchange section 52 takes in right-eye fundus light, described later, and supplies the taken-in right-eye fundus light to a light management section 116 through the optical fiber 38, the optical splitter 20, and the optical fiber 30.

The right-eye reflection mirror 42R includes a curved surface 42R1. The curved surface 42R1 is a surface formed so as to be concave as viewed from the right eye 44R of the patient in a state in which the eyewear terminal device 16 is being worn. Due to the examination light guided by the MEMS minor 56 being reflected at the curved surface 42R1, the examination light is guided through a lens 64R behind the pupil of the right eye 44R and onto the retina 46R of the right eye 44R.

The left-eye scanner 28L includes MEMS mirrors 60, 62, and scans the laser beam supplied from through a left-eye light exchange section 58. The left-eye light exchange section 58 shines the laser beam supplied from the laser optical splitter 20 through the optical fiber 40. The MEMS mirror 60 is disposed on the direction of illumination of the laser beam by the left-eye light exchange section 58, and the MEMS mirror 60 reflects the laser beam shone from the left-eye light exchange section 58 so as to be guided onto the MEMS minor 62. The MEMS minor 62 reflects the laser beam guided by the MEMS mirror 60 so as to be guided onto the left-eye reflection minor 42L.

For example, the MEMS minor 60 scans the laser beam in the Y direction, and the MEMS minor 62 scans the laser beam in the X direction. Two-dimensional scanning on the retina is enabled by the MEMS minors 60, 62, enabling a picture to be two-dimensionally scanned and projected onto the retina.

Obviously a configuration may be adopted in which the MEMS mirror 60 scans in the X direction and the MEMS mirror 62 scans in the Y direction.

Furthermore, the left-eye scanner 28L may be configured by employing the reflection mirror 42L and a MEMS minor 56 capable of scanning in the XY directions.

Although the MEMS mirrors 54, 56, 60, 62 are given as examples in the example illustrated in FIG. 2, the technology disclosed herein is not limited thereto. For example, instead of the MEMS minors 54, 56, 60, 62, or together with one or more of the MEMS mirrors 54, 56, 60, 62, a minor such as a galvanometer minor and/or a polygon mirror or the like that enables electrical control of the position on the reflection face may be employed.

The left-eye reflection mirror 42L reflects the examination light scanned by the left-eye scanner 28L onto the retina 46L.

The left-eye light exchange section 58 takes in left-eye fundus light, described later, and supplies the taken-in left-eye fundus light to the light management section 116 through the optical fiber 40, the optical splitter 20, and the optical fiber 30.

The left-eye reflection mirror 42L includes a curved surface 42L1. The curved surface 42L1 is a surface formed so as to be concave as viewed from the left eye 44L of the patient in a state in which the eyewear terminal device 16 is being worn. Due to the examination light guided by the MEMS minor 62 being reflected at the curved surface 42L1, the examination light is guided through a lens 64L behind the pupil of the left eye 46R and onto the retina 46L of the left eye 44L.

Note that when there is no need to discriminate between the lenses 64R, 64L in the description below, for ease of explanation they will be referred to as "lenses 64".

The optical system 27 is equipped with a right-eye sliding mechanism 70R, a left-eye sliding mechanism 70L, a right-eye drive source 72R, and a left-eye drive source 72L. Examples of the right-eye drive source 72R and the left-eye drive source 72L include a stepping motor, a solenoid, and a piezoelectric element or the like. Note that when there is no need to discriminate between the right-eye drive source 72R and the left-eye drive source 72L in the description below, for ease of explanation they will be referred to as "minor drive sources 72".

The right-eye sliding mechanism 70R is attached to the rim piece 22, and is held thereby so as to enable the right-eye reflection mirror 42R to slide in the left-right direction. The right-eye sliding mechanism 70R is connected to the right-eye drive source 72R, and slides the right-eye reflection mirror 42R in the left-right direction on receipt of motive force generated by the right-eye drive source 72R.

The left-eye sliding mechanism 70L is attached to the rim piece 22, and is held thereby so as to enable the left-eye reflection mirror 42L to slide in the left-right direction. The left-eye sliding mechanism 70L is connected to the left-eye drive source 72L, and slides the left-eye reflection minor 42L in the left-right direction on receipt of motive force generated by the left-eye drive source 72L.

In the ophthalmic system 10 according to the present exemplary embodiment, a picture arising from the laser beam is projected onto the retina 46 of the subject eye 44 by a Maxwellian view optical system. Reference here to "Maxwellian view optical system" indicates an optical system in which laser beams are converged by the lenses 64 behind the pupils of the subject eyes 44, and pictures arising from the laser beams are projected onto the retinas 46 of the subject eyes 44 by the laser beams converged by the lenses 64 being shone onto the retinas 46 of the subject eyes 44. In the ophthalmic system 10 according to the present exemplary embodiment, the Maxwellian view optical system is implemented by the scanner 28 and the mirror drive sources 72 being controlled by the control device 18.

As illustrated for example in FIG. 3, the management device 14 includes a main control section 80, a wireless communication section 82, a reception device 84, a touch panel display 86, and an external OF 88. Note that the main control section 80 is an example of a management device-side control section according to technology disclosed herein.

The main control section 80 includes a CPU 90, a primary storage section 92, a secondary storage section 94, a bus line 96, and an I/O 98. The CPU 90, the primary storage section 92, and the secondary storage section 94 are connected together through the bus line 96. The I/O 98 is connected to the bus line 96. Note that although a single CPU is employed for the CPU 90 in the present exemplary embodiment, plural CPUs may be employed instead of the CPU 90.

The CPU 90 controls the management device 14 overall. The primary storage section 92 is volatile memory employed as a work area or the like when various programs are being executed. An example of the primary storage section 92 is RAM. The secondary storage section 94 is non-volatile memory to store a program and various parameters and the like employed to control the basic operation of the management device 14. Example of the secondary storage section 94 include a HDD, EEPROM, and flash memory or the like.

The wireless communication section 82 is connected to the I/O 98. The CPU 90 outputs to the wireless communication section 82 an electrical signal for transmission to the control device 18. The wireless communication section 82 transmits the electrical signal input from the CPU 90 to the control device 18 using radio waves. The wireless communication section 82 also receives radio waves from the control device 18, and outputs to the CPU 90 an electrical signal according to the received radio waves. Note that the wireless communication section 82 is an example of a communication section according to technology disclosed herein. Namely, the wireless communication section 82 transmits to the wearable terminal device 12 control information that is control information for the wearable terminal device 12 to control a control section 170, described later, (see FIG. 14) and that includes instruction information to instruct an examination subject eye for ophthalmic examination from out of the two eyes of the patient.

The reception device 84 includes a touch panel 84A, a keyboard 84B, and a mouse 84C, with the touch panel 84A, the keyboard 84B, and the mouse 84C being connected to the I/O 98. This accordingly enables the CPU 90 to ascertain various instructions received by each of the touch panel 84A, the keyboard 84B, and the mouse 84C.

The external OF 88 is connected to external devices, such as the server device 15, a personal computer, and/or a USB memory or the like, and is employed to exchange various information between the external devices and the CPU 90. In the example illustrated in FIG. 3, the external OF 88 is connected to the server device 15 by the cable 23.

The touch panel display 86 includes a display 86A and a touch panel 84A. The display 86A is an example of a display section according to technology disclosed herein. The display 86A is connected to the I/O 98 and displays various information including pictures under control from the CPU 90. The touch panel 84A is a transparent touch panel superimposed on the display 86A.

The secondary storage section 94 stores a terminal management program 94A, a display control program 94B, and a communication error response program 94C.

When there is no need to discriminate in the description between the terminal management program 94A, the display control program 94B, and the communication error response program 94C below, for ease of explanation they will be referred to as "management device-side programs".

The CPU 90 reads the management device-side programs from the secondary storage section 94, and expands the read management device-side programs into the primary storage section 92. The CPU 90 executes the management device-side programs that have been expanded into the primary storage section 92.

The control device 18 is equipped with, as well as the response button 19 mentioned above, a main control section 110, the wireless communication section 112, and the light management section 116. The main control section 110, the wireless communication section 112, and the light management section 116 are housed in the same casing. Note that the main control section 110 is an example of a control section according to technology disclosed herein.

The main control section 110 includes a CPU 120, a primary storage section 122, a secondary storage section 124, a bus line 126, and an I/O 128. The CPU 120, the primary storage section 122, and the secondary storage section 124 are connected together through the bus line 126. The I/O 128 is connected to the bus line 126. Note that although a single CPU is employed for the CPU 120 in the present exemplary embodiment, plural CPUs may be employed instead of the CPU 120.

The CPU 120 controls the wearable terminal device 12 overall. The primary storage section 122 is volatile memory employed as a work area or the like when various programs are being executed. An example of the primary storage section 122 is RAM. The secondary storage section 124 is non-volatile memory to store a program and various parameters and the like employed to control the basic operation of the wearable terminal device 12. Examples of the secondary storage section 124 include a HDD, EEPROM, and flash memory or the like.

The response button 19 is connected to the I/O 128, and a response signal is output from the response button 19 to the CPU 120 when the response button 19 is pressed.

The wireless communication section 112 performs wireless communication with the management device 14 to allow the management device 14 to manage the ophthalmic examination performed by the wearable terminal device 12. The wireless communication section 112 is connected to the I/O 128. The CPU 120 outputs to the wireless communication section 112 an electrical signal for transmission to the management device 14. The wireless communication section 112 transmits the electrical signal input from the CPU 120 to the management device 14 using radio waves. The wireless communication section 112 also receives radio waves from the management device 14, and outputs to the CPU 120 an electrical signal according to the received radio waves.

The light management section 116 is an example of an light emitter according to technology disclosed herein, and is connected to the optical splitter 20 through the optical fiber 30. The light management section 116 generates examination light, and emits the generated examination light to the optical splitter 20 through the optical fiber 30.

As illustrated in the example in FIG. 5, the light management section 116 is equipped with a light source 114, a light source control circuit 115, and an optical detection section 117. The light source control circuit 115 is connected to the I/O 128. The light source control circuit 115 is also connected to the light source 114. The light source control circuit 115 controls the light source 114 by supplying a light source control signal to the light source 114 under instruction from the CPU 120.

The light source 114 includes laser light source units 113, an IR laser light source 114D, and a mirror unit 130. The laser light source units 113 are examples of a first light source unit and of an SLO light source according to technology disclosed herein, and the IR laser light source 114D is an example of a second light source unit and an OCT light source according to technology disclosed herein. The laser light source unit 113 is equipped with an R light source 114A, a G light source 114B, and a B light source 114C, and emits visible light.

The R light source 114A emits an R laser beam that is an R laser beam from out of R, G, and B. The G light source 114B emits a G laser beam that is a G laser beam from out of R, G, and B. The B light source 114C emits a B laser beam that is a B laser beam from out R, G, and B. The IR laser light source 114D emits an IR laser beam.

The mirror unit 130 is equipped with a first minor 130A, a second mirror 130B, and a third mirror 130C. From out of the first minor 130A, the second minor 130B, and the third minor 130C, the second mirror 130B is a dichroic mirror that transmits the B laser beam while reflecting the G laser beam. The third mirror 130C is also a dichroic mirror, and transmits the R laser beam while reflecting the G laser beam and the B laser beam.

The first minor 130A is disposed in the direction in which the B laser beam is emitted by the B light source 114C, and guides the B laser beam to the second mirror 130B by reflecting the B laser beam emitted from the B light source 114C.

The second mirror 130B is disposed in the direction in which the G laser beam is emitted by the G light source 114B and is also on the direction of progression of the B laser beam reflected by the first mirror 130A. The second mirror 130B guides the G laser beam to the first mirror 130A by reflecting the G laser beam emitted from the G light source 114B, and also guides the B laser beam to the first minor 130A by transmitting the B laser beam reflected by the first mirror 130A.

The third minor 130C is disposed on the direction in which the R laser beam is emitted by the R light source 114A and also on the direction of progression of the G laser beam reflected by the second mirror 130B as well as on the direction of progression of the G laser beam transmitted through the second mirror 130B. The third mirror 130C transmits the R laser beam emitted from the R light source 114A. The third minor 130C externally emits the R laser beam, the G laser beam, and the B laser beam by reflecting the G laser beam and the B laser beam so as to travel in the same direction as the R laser beam. The three primary color laser beam is thereby emitted externally from the light source 114.

The optical detection section 117 is equipped with the beam splitters 129, 135 and the mirrors 137, 143. The optical detection section 117 is equipped with an SLO optical detection section 131 and an OCT optical detection section 133.

A beam splitter 135 is disposed in the direction of emission of the IR laser beam emitted from the light source 114. A minor 137 is disposed in the direction of emission of the three primary color laser beam emitted from the light source 114. The beam splitter 135 reflects part of the IR laser beam from the light source 114 so as to be guided to the mirror 137, and also transmits part of the IR laser beam so as to be supplied as reference light into the OCT optical detection section 133.

The mirror 137 is a dichroic mirror that transmits the laser beam from the light source 114 and also reflects the IR laser beam guided by the beam splitter 135.

A beam splitter 129 is a dichroic minor and is disposed on the direction of progression of the examination light guided by the minor 137, namely, disposed on the direction of progression of the laser beam transmitted by the mirror 137 and the IR laser beam reflected by the minor 137.

The beam splitter 129 guides the examination light into the optical fiber 30 by reflecting the examination light guided by the mirror 137. The beam splitter 129 transmits fundus light. The fundus light indicates light reflected by the fundus of the subject eye 44. The fundus light is guided from the optical fiber 30 to the beam splitter 129. The examination light is broadly divided into left-eye light and right-eye light. The left-eye light indicates examination light employed in the left-eye optical system 27L, and the right-eye light indicates examination light employed in the right-eye optical system 27R.

The fundus light is broadly divided into left-eye fundus light and right-eye fundus light. The left-eye fundus light indicates reflected light from the fundus of the left eye 44L, namely, light obtained when the left-eye light is reflected at the fundus of the left eye 44L (for example, the retina 46L (see FIG. 2)). The right-eye fundus light indicates reflected light from the fundus of the right eye 44R, namely, light obtained when the right-eye light is reflected at the fundus of the right eye 44R (for example, the retina 46R (see FIG. 2)).

The left-eye fundus light is broadly divided into left-eye SLO light when the left eye 44L is being SLO imaged and left-eye OCT light (signal light) when the left eye 44L is being OCT imaged. SLO imaging indicates imaging the retina 46 as the imaging subject using an SLO. OCT imaging indicates imaging the retina 46 as the imaging subject using OCT. The left-eye SLO light indicates light obtained when a laser beam is reflected at the retina 46L. The left-eye OCT light indicates light obtained when an IR laser beam is reflected at the retina 46L.

The right-eye fundus light is broadly divided into right-eye SLO light when the right eye 44R is being SLO imaged and right-eye OCT light (signal light) when the right eye 44R is being OCT imaged. The right-eye SLO light indicates light obtained when a laser beam is reflected at the retina 46R. The right-eye OCT light indicates light obtained when an IR laser beam is reflected at the retina 46R.

Note that when there is no need to discriminate between the left-eye SLO light and the right-eye SLO light in the description below, for ease of explanation they will be referred to as "SLO light". Moreover, when there is no need to discriminate between the left-eye OCT light and the right-eye OCT light in the description below, for ease of explanation they will be referred to as "OCT light".

A mirror 143 is a dichroic minor and guides SLO light (signal light) to an SLO optical detection section 131 when performing SLO imaging, guides OCT light (signal light) to the OCT optical detection section 133 when performing COT imaging, splits the fundus light into SLO light and OCT light when performing SLO imaging and OCT imaging on the same eye at the same time, and guides the SLO light to the optical detection section 131 and guides the OCT light to the OCT optical detection section 133. Namely, the mirror 143 reflects the right-eye SLO light from out of the right-eye fundus light transmitted through the beam splitter 129 so as to be guided to the SLO optical detection section 131, and transmits the right-eye OCT light therefrom so as to be guided to the OCT optical detection section 133. The mirror 143 reflects the left-eye SLO light from out of the left-eye fundus light transmitted through the beam splitter 129 so as to be guided to the SLO optical detection section 131 and transmits the left-eye OCT light therefrom so as to be guided to the OCT optical detection section 133.

The SLO optical detection section 131 detects the SLO light. The SLO optical detection section 131 is connected to the I/O 128 and outputs SLO detection information representing the results of SLO light detection to the CPU 120. The SLO detection information is broadly divided into left-eye SLO detection information representing the results of left-eye SLO light detection and right-eye SLO detection information representing the results of right-eye SLO light detection. In the present exemplary embodiment a planar two-dimensional fundus image is generated based on the SLO detection information.

The OCT optical detection section 133 detects interference light from the interference of the reference light and the OCT light (signal light). The OCT optical detection section 133 is connected to the I/O 128 and outputs OCT detection information representing the results of interference light detection to the CPU 120. Note that the OCT detection information is broadly divided into left-eye OCT detection information representing detection results based on left-eye OCT light, and right-eye OCT detection information representing detection results based on right-eye OCT light, and includes OCT data to draw a tomographic image of the retina 46 and/or a three-dimensional image representing a three-dimensional shape of the retina 46.

As illustrated for example in FIG. 3, the bus line 32 is connected to the I/O 128, and the optical splitter 20 is connected to the bus line 32. Thus the optical splitter 20 acts under the control of the CPU 120.

Figure 6:
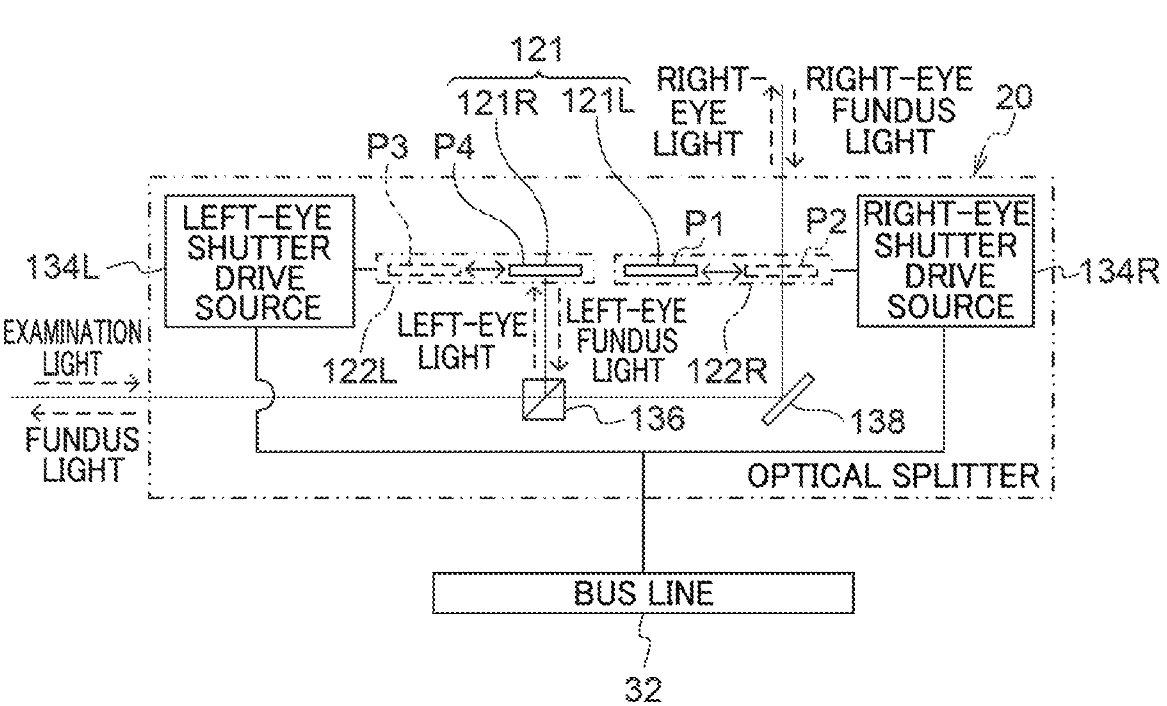
FIG. 6 is a schematic configuration diagram illustrating an example of a configuration of an optical splitter included in a wearable terminal device of an ophthalmic system according to the first exemplary embodiment.

In the example illustrated in FIG. 6, the optical splitter 20 includes a right-eye shutter 121R, a left-eye shutter 121L, a third sliding mechanism 122R, a fourth sliding mechanism 122L, a right-eye shutter drive source 134R, a left-eye shutter drive source 134L, a beam splitter 136, and a reflection mirror 138.

When there is no need to discriminate between the right-eye shutter 121R and the left-eye shutter 121L in the description below, for ease of explanation they will be referred to as "shutters 121".

The beam splitter 136 both reflects and transmits left-eye light that is the examination light supplied from the light management section 116 through the optical fiber 30. The left-eye light reflected at the beam splitter 136 proceeds toward the optical fiber 40 (see FIG. 1 and FIG. 2). Moreover, left-eye fundus light is supplied through the optical fiber 40 to the beam splitter 136, and the beam splitter 136 reflects the left-eye fundus light so as to be guided into the optical fiber 30.

The reflection mirror 138 reflects right-eye light that is the examination light transmitted through the beam splitter 136. The right-eye light reflected by the reflection mirror 138 proceeds toward the optical fiber 38 (see FIG. 1 and FIG. 2). Moreover, right-eye fundus light is supplied through the optical fiber 38 to the beam splitter 136, and the beam splitter 136 reflects the right-eye fundus light so as to be guided into the optical fiber 30.

The third sliding mechanism 122R holds the right-eye shutter 121R so as to be capable of sliding between a first position P1 and a second position P2. The first position P1 indicates a position where the right-eye light is transmitted and guided to the optical fiber 38 and right-eye fundus light is transmitted and guided to the reflection mirror 138, and the second position P2 indicates a position where both the right-eye light and the right-eye fundus light are blocked.

The fourth sliding mechanism 122L holds the left-eye shutter 121L so as to be capable of sliding between a third position P3 and a fourth position P4. The third position P3 indicates a position where the left-eye light is transmitted and guided to the optical fiber 40 and the left-eye fundus light is transmitted and guided to the beam splitter, and the fourth position P4 indicates a position where both the left-eye light and the left-eye fundus light are blocked.

Examples of the right-eye shutter drive source 134R and the left-eye shutter drive source 134L include a stepping motor, a solenoid, and a piezoelectric element or the like. The right-eye shutter drive source 134R and the left-eye shutter drive source 134L are connected to the bus line 32, and the right-eye shutter drive source 134R and the left-eye shutter drive source 134L are operated under the control of the CPU 120.

The third sliding mechanism 122R is connected to the right-eye shutter drive source 134R, and slides the right-eye shutter 121R between the first position P1 and the second position P2 on receipt of motive force generated by the right-eye shutter drive source 134R.

The fourth sliding mechanism 122L is connected to the left-eye shutter drive source 134L and slides the left-eye shutter 121L between the third position P3 and the fourth position P4 on receipt of motive force generated by the left-eye shutter drive source 134L.

In the example illustrated in FIG. 6, the right-eye light is supplied into the optical fiber 38 and the right-eye fundus light is guided to the reflection mirror 138 by the right-eye shutter 121R being disposed at the first position P1. Moreover, in the example illustrated in FIG. 6, both the left-eye light and the left-eye fundus light are blocked by the left-eye shutter 121L due to the left-eye shutter 121L being disposed at the fourth position P4.

For example, as illustrated in FIG. 3, the speaker 140 is connected to the bus line 32 and outputs audio under the control of the CPU 120.

The right-eye drive source 72R and the left-eye drive source 72L are connected to the bus line 32, and the CPU 120 controls the right-eye drive source 72R and the left-eye drive source 72L.

The right-eye inward-facing camera 48R and the left-eye inward-facing camera 48L are connected to the bus line 32, and the CPU 120 exchanges various kinds of information with the left-eye inward-facing camera 48L and the right-eye inward-facing camera 48R.

The right-eye light exchange section 52, the left-eye light exchange section 58, and the MEMS minors 54, 56, 60, 62 are also connected to the bus line 32, and the CPU 120 controls the right-eye light exchange section 52, the left-eye light exchange section 58, and the MEMS minors 54, 56, 60, 62.

A wearing detector 139 is connected to the bus line 32. The wearing detector 139 is, for example, a pressure sensor. The wearing detector 139 is provided on the frame of the eyewear terminal device 16 and detects whether the eyewear terminal device 16 is being worn correctly. The CPU 120 acquires a detection result from the wearing detector 139. The frame of the eyewear terminal device 350 indicates, for example, the rim piece 22 and the temple piece 24.

The secondary storage section 124 stores a terminal-side program 124A. The CPU 120 reads the terminal-side program 124A from the secondary storage section 124, and expands the read terminal-side program 124A into the primary storage section 122. The CPU 120 executes the terminal-side program 124A that has been expanded into the primary storage section 122.

As illustrated in the example of FIG. 4, the server device 15 is equipped with a main control section 150, a reception device 154, a touch panel display 156, and an external OF 158.

The main control section 150 includes a CPU 160, a primary storage section 162, a secondary storage section 164, a bus line 166, and an I/O 168. The CPU 160, the primary storage section 162, and the secondary storage section 164 are connected together through the bus line 166. The I/O 168 is connected to the bus line 166. Note that although a single CPU is employed for the CPU 160 in the present exemplary embodiment, plural CPUs may be employed instead of the CPU 160.

The CPU 160 controls the server device 15 overall. The primary storage section 162 is volatile memory employed as a work area or the like when various programs are being executed. An example of the primary storage section 162 is RAM. The secondary storage section 164 is non-volatile memory to store a program and various parameters and the like employed to control the basic operation of the server device 164. Examples of the secondary storage section 164 include a HDD, EEPROM, and flash memory or the like.

The reception device 154 includes a touch panel 154A, a keyboard 154B, and a mouse 154C, with the touch panel 154A, the keyboard 154B, and the mouse 154C being connected to the I/O 168. This accordingly enables the CPU 160 to ascertain various instructions received by each of the touch panel 154A, the keyboard 154B, and the mouse 154C.

The external I/F 158 is connected to external devices, such as the management device 14, a personal computer, and/or a USB memory or the like, and is employed to exchange various information between the external devices and the CPU 160. In the example illustrated in FIG. 4, the external OF 158 is connected to the external OF 88 of the management device 14 by the cable 23.

The touch panel display 156 includes a display 156A and a touch panel 154A. The display 86A is connected to the I/O 168 and displays various information including pictures under control from the CPU 160. The touch panel 154A is a transparent touch panel superimposed on the display 156A.

The secondary storage section 164 stores patient information 164A and a server-side program 164B.

The patient information 164A is information related to the patient. In the present exemplary embodiment, the patient information 164A includes patient profile information 164A1 (for example, an ID to identify the patient, patient name, patient gender, patient age, physical information, past treatment history, current patient information such as hospitalization status, risk of disease, and physical state and the like) and optometry information 164A2 of optometry performed on the patient. The optometry information 164A2 includes other information related to the left eye/right eye of the patient (for example, corneal refractive power, corneal wavefront aberration, visual acuity, myopia/hyperopia/astigmatism, field of view, eye axial length, fundus photograph or the like that is information obtained with a different ophthalmic instrument). Examples of the different ophthalmic instrument include a refractive power measurement instrument, eye axial length measurement instrument, a visual acuity tester, an anterior segment measurement instrument, a posterior segment measurement instrument, and the like.

As illustrated for example in FIG. 4, the viewer 17 is equipped with a main control section 17A, a touch panel display 17B, a reception device 17D, and an external I/F 17M.

The main control section 17A includes a CPU 17H, a primary storage section 171, a secondary storage section 17J, a bus line 17K, and an I/O 17L. The CPU 17H is connected to the primary storage section 171, and the secondary storage section 17J through the bus line 17K. The I/O 17L is connected to bus line 17K. Note that although a single CPU is employed for the CPU 17H in the present exemplary embodiment, plural CPUs may be employed instead of the CPU 17H.

The CPU 17H controls the viewer 17 overall. The primary storage section 171 is volatile memory employed as a work area or the like when various programs are being executed. An example of the primary storage section 171 is RAM. The secondary storage section 17J is non-volatile memory employed to store a program and various parameters and the like employed to control the basic operation of the viewer 17. Examples of the secondary storage section 17J include a HDD, EEPROM, and flash memory or the like. The secondary storage section 164 stores a viewer-side program 17J1.

The reception device 17D includes a touch panel 17E, a keyboard 17F, and a mouse 17G, and the touch panel 17E, the keyboard 17F, and the mouse 17G are connected to the I/O 17L. This accordingly enables the CPU 17H to ascertain various instructions received through the touch panel 17E, the keyboard 17F, or the mouse 17G.

The external OF 17M is connected to external devices, such as the management device 14, the server device 15, a personal computer, and/or USB memory or the like, and is employed to exchange of various information between the external devices and the CPU 17H. Note that in the example illustrated in FIG. 4, the external OF 17M is connected to the external I/F 88 of the management device 14 and the external OF 158 of the server device 15 by the cable 23.

The touch panel display 17B includes a display 17C and a touch panel 17E. The display 17C is connected to the I/O 17L and displays various information including pictures under the control of the CPU 17H. The touch panel 17E is a transparent touch panel superimposed on the display 17C.

The CPU 160 reads the server-side program 164B from the secondary storage section 164 and expands the read server-side program 164B into the primary storage section 162. The CPU 160 executes the server-side program 164B that has been expanded into the primary storage section 162.

Figure 14:
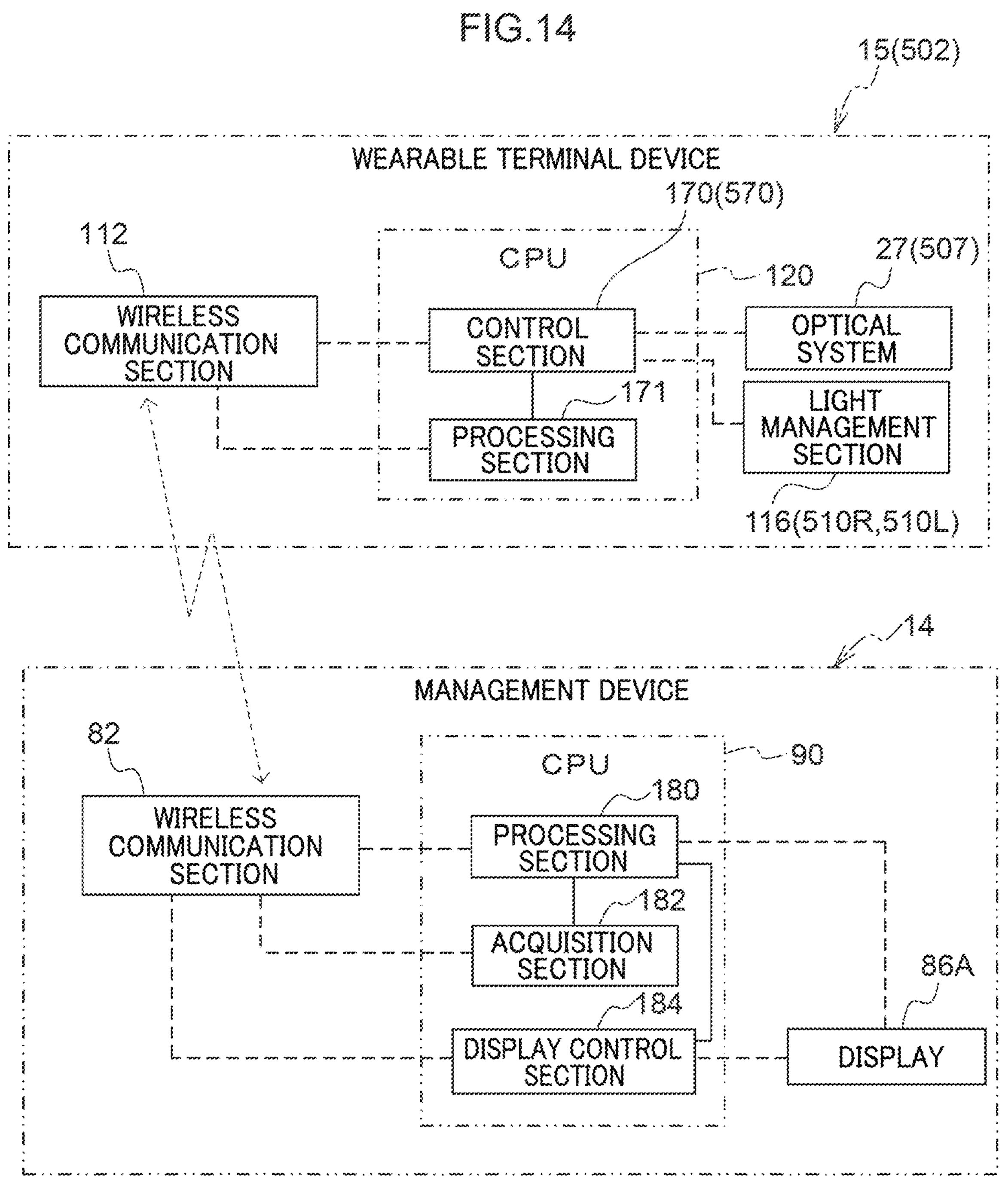
FIG. 14 is a block diagram illustrating an example of relevant functions of an ophthalmic system according to the first to third exemplary embodiments.

By executing the terminal-side program 124A, the CPU 120 of the main control section 110 included in the wearable terminal device 12 operates as a control section 170 and a processing section 171, as illustrated in the example of FIG. 14.

The processing section 171 performs processing required to cause the CPU 120 to operate as the control section 170. The control section 170 controls the light management section 116 and the optical system 27 so as to shine examination light on the retina 46R and/or the retina 46L.

By executing the terminal management program 94A, the CPU 90 of the main control section 80 included in the management device 14 operates as a processing section 180 and an acquisition section 182, as illustrated in the example in FIG. 14. By executing the display control program 94B, the CPU 90 operates as a processing section 180 and display control section 184, as illustrated in the example in FIG. 15.

The processing section 180 performs processing required to cause the CPU 90 to operate as the acquisition section 182 and the display control section 184. The acquisition section 182 performs communication with the wearable terminal device 12 and the management device 14 through the wireless communication sections 82, 112 so as to acquire sensing information and/or fundus image information from the wearable terminal device 12. The fundus image information referred to here indicates, for example, field-of-view defect map information, described later, SLO images, and OCT images.

The display control section 184 generates a state-of-progress screen 190 (see FIG. 13) that is a screen representing the state of progress of ophthalmic examination, and outputs an image signal representing an image including the generated state-of-progress screen 190. The display 86A displays the state-of-progress screen 190 based on the image signal input from the display control section 184. Namely, the display control section 184 controls the display 86A so as to cause the display 86A to display the state-of-progress screen 190. The display control section 184 acquires from the wearable terminal device 12 state-of-progress information indicating the state of progress of ophthalmic examination by the wearable terminal device 12 and the management device 14 communicating through the wireless communication sections 82, 112. The display control section 184 generates the state-of-progress screen 190 based on the state-of-progress information, and controls the display 86A so that the generated state-of-progress screen 190 is displayed on the display 86A.

Note that, as illustrated in the example of FIG. 13, in the present exemplary embodiment the state-of-progress screen 190 is broadly composed of a first state-of-progress screen 190A, a second state-of-progress screen 190B, a third state-of-progress screen 190C, a fourth state-of-progress screen 190D, a fifth state-of-progress screen 190E, and a sixth state-of-progress screen 190F. Namely, the first state-of-progress screen 190A, the second state-of-progress screen 190B, the third state-of-progress screen 190C, the fourth state-of-progress screen 190D, the fifth state-of-progress screen 190E, and the sixth state-of-progress screen 190F are displayed on the display 86A.

Explanation next follows regarding operation of the sections of the ophthalmic system 10 according to technology disclosed herein.

First explanation will be given regarding terminal management processing implemented by the CPU 90 executing the terminal management program 94A when an instruction to start executing of terminal management processing is received by the reception device 84, with reference to FIG. 7A and FIG. 7B.

For ease of explanation, the following description assumes that at least one patient is appropriately wearing one of the wearable terminal devices 12.

Moreover, for ease of explanation, the following description assumes that a fixation target is being presented in a visible state to the patient.

Figure 7A:
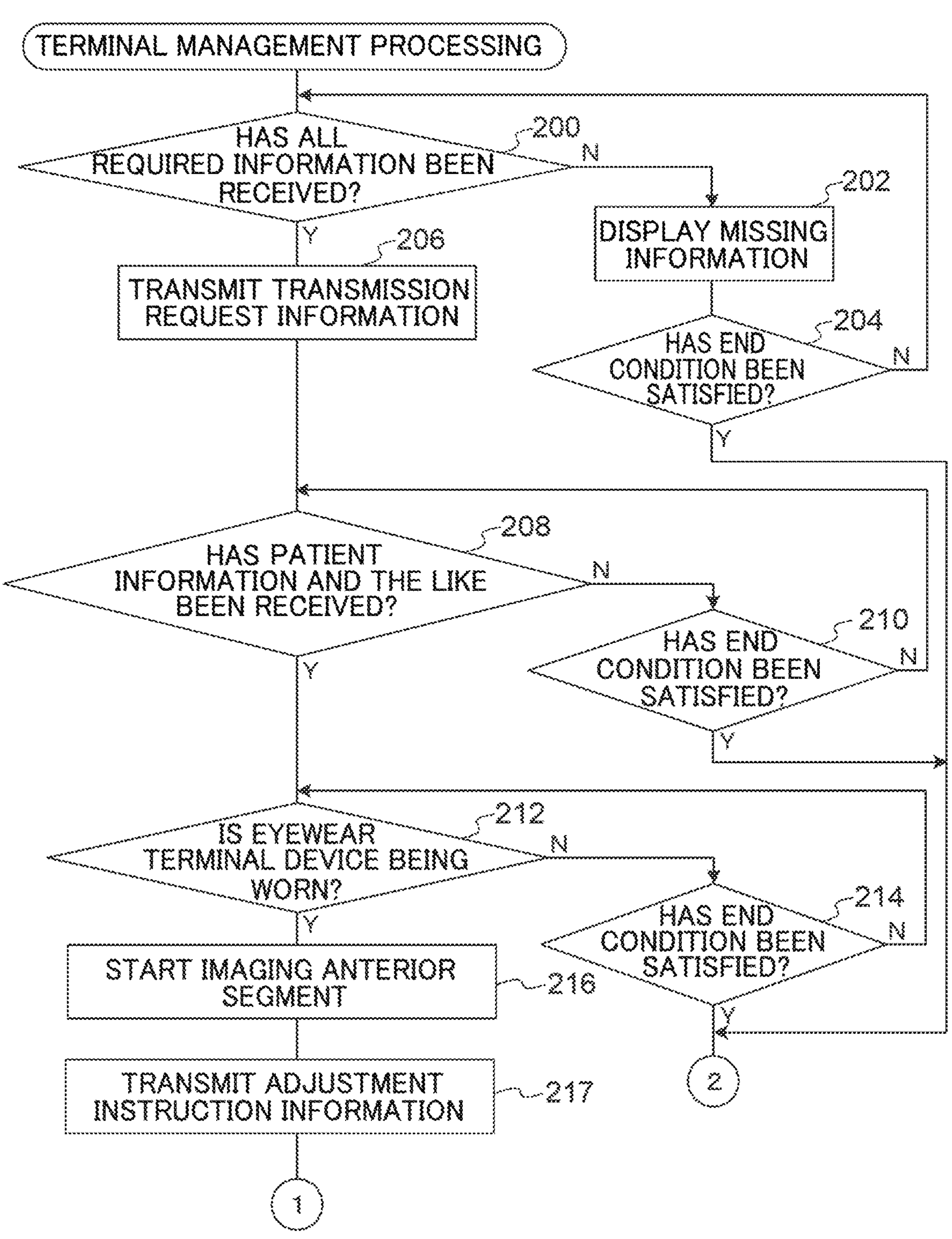
FIG. 7A is a flowchart illustrating an example of a flow of terminal management processing according to first to third exemplary embodiments.

In the terminal management processing illustrated in FIG. 7A first, at step 200, determination is made as to whether or not the processing section 180 has received all of the required information required by the reception device 84 and/or the server device 15. The "required information" indicates information required for an ophthalmic examination, such as examination subject eye instruction information, patient ID, eyewear ID, and the like. The examination subject eye instruction information refers to information instructing which the subject eye 44 subjected to examination is from out of the right eye 44R and the left eye 44L. The patient ID indicates information enabling the patient to be uniquely identified. The eyewear ID indicates information enabling the wearable terminal device 12 being worn by the patient to be uniquely identified.

Processing transitions to step 202 when negative determination is made at step 200, i.e. when not all of the required information has been received by the reception device 84.

Processing transitions to step 206 when affirmative determination is made at step 200, i.e. when all of the required information has been received by the reception device 84.

At step 202 the processing section 180 displays missing information on the display 86A, and then processing transitions to step 204. The missing information indicates, for example, a message showing which information is missing from out of the information required for ophthalmic examination.

At step 204, the processing section 180 determines whether or not the processing section 180 has satisfied an end condition relating to terminal management processing.

The end condition relating to terminal management processing indicates a condition to end the terminal management processing. Examples of the end condition relating to terminal management processing include a condition that a specific period of time has elapsed, a condition that an end instruction has been received by the reception device 84, and/or a condition that a situation requiring the terminal management processing to be forcibly ended has been detected by the CPU 90.

Processing transitions to step 200 when negative determination is made at step 204, i.e. when the end condition relating to terminal management processing has not been satisfied. The terminal management processing is ended when affirmative determination is made at step 204, i.e. when the end condition relating to terminal management processing has been satisfied.

At step 206, the processing section 180 transmits to the server device 15 transmission request information requesting the patient information 164A to be transmitted, and then processing transitions to step 208.

By executing the processing of the present step 206, the patient information and the like is transmitted from the server device 15 by the processing of step 256 included in the server-side processing, described later.

The patient information and the like indicates information including at least the patient information 164A and examination sequence information. The examination sequence information includes information indicating whether or not to perform a visual field test, information indicating whether or not to perform an SLO image examination, and information indicating whether or not to perform an OCT image examination. Sequence pattern information is also included in the examination sequence information. The sequence pattern information indicates information indicating a sequence pattern in which to perform plural examinations from out of visual field tests, SLO image examinations, and OCT image examinations (hereafter referred to as "sequence pattern").

The sequence pattern includes, for example, a pattern for the right eye 44R and the left eye 44L arrived at by combining at least two examinations from out of the visual field test, the SLO image examination, and the OCT image examination. Note that for ease of explanation, a description follows regarding examples of a case in which the visual field test is performed alone, a case in which the SLO image examination is performed alone, a case in which the OCT image examination is performed alone, and a case in which examinations are performed in the sequence of the visual field test, then the SLO image examination, and then the OCT image examination.

Figure 10:
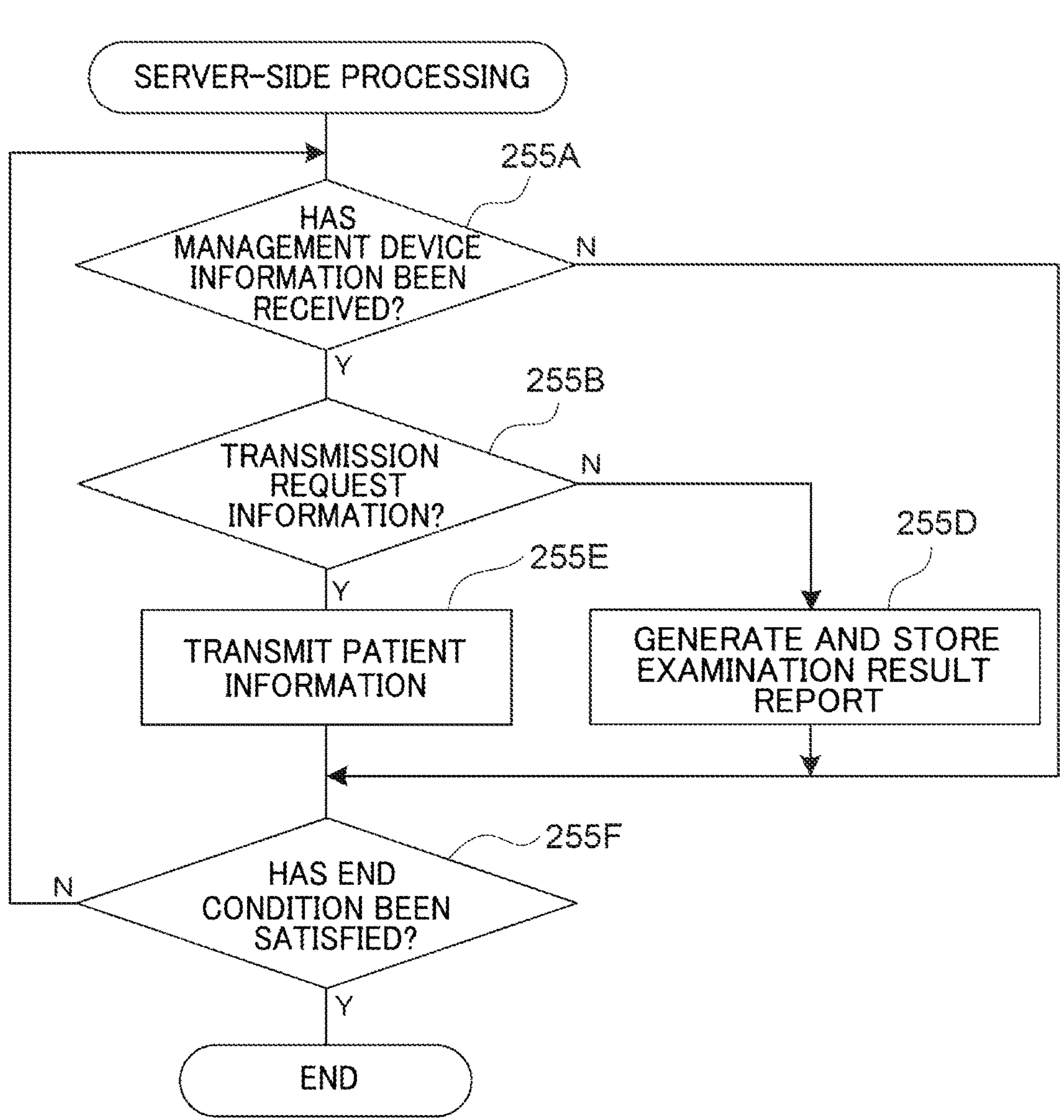
FIG. 10 is a flowchart illustrating an example of a flow of server-side processing according to the first to third exemplary embodiments.

At step 208, the processing section 180 determines whether or not the patient information and the like, that was transmitted by execution of the processing of step 255A included in the server-side processing illustrated in FIG. 10, has been received by the wireless communication section 82. Processing transitions to step 210 when negative determination is made at step 208, i.e. when the patient information and the like has not been received. Processing transitions to step 212 when affirmative determination is made at step 206, i.e. when the patient information and the like has been received.

At step 210 the processing section 180 determines whether or not the end condition relating to terminal management processing has been satisfied. Processing transitions to step 208 when negative determination is made at step 210, i.e. when the end condition relating to terminal management processing has not been satisfied. The terminal management processing is ended when affirmative determination is made at step 210, i.e. when the end condition relating to terminal management processing has been satisfied.

At step 212, the processing section 180 determines whether or not the eyewear terminal device 16 is being worn correctly by the patient by communicating with the control device 18 through the wireless communication sections 82, 112. Processing transitions to step 214 when negative determination is made at step 212, i.e. when the eyewear terminal device 16 is not being worn correctly by the patient. Processing transitions to step 216 when affirmative determination is made at step 212, i.e. when the eyewear terminal device 16 is being worn correctly by the patient. Note that whether or not the eyewear terminal device 16 is being worn correctly by the patient is determined based on detection results by the wearing detector 139.

At step 214 the processing section 180 determines whether or not the end condition relating to terminal management processing has been satisfied. Processing transitions to step 212 when negative determination is made at step 214, i.e. when the end condition relating to terminal management processing has not been satisfied. The terminal management processing is ended when affirmative determination is made at step 214, i.e. when the end condition relating to terminal management processing has been satisfied.

Figure 7B:
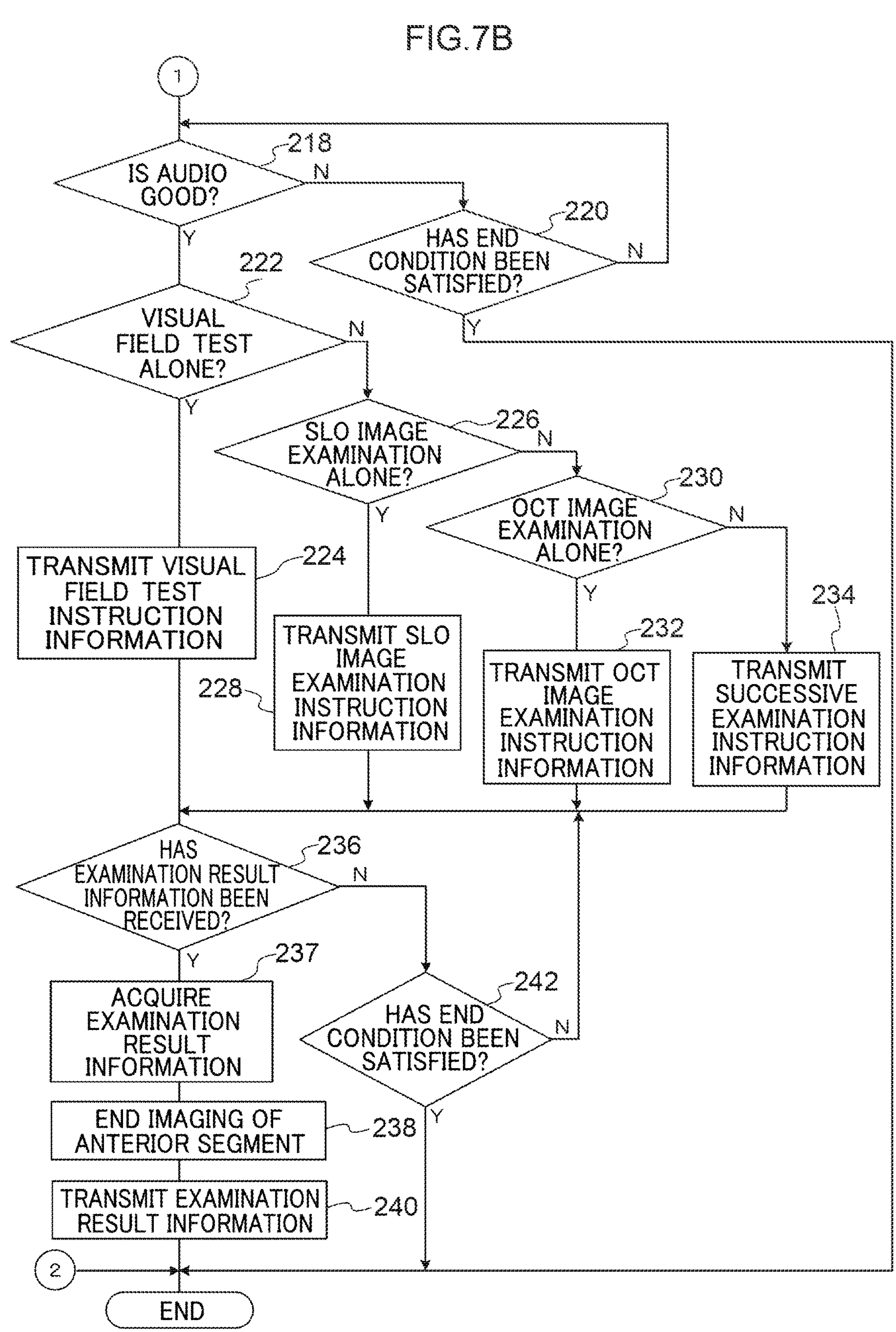
FIG. 7B is a continuation flowchart of the flowchart illustrated in FIG. 7A.

At step 216, the processing section 180 causes the right-eye inward-facing camera 48R and the left-eye inward-facing camera 48L to start imaging the anterior segment of the subject eye 44 by performing wireless communication with the control device 18, and then processing transitions to step 217 illustrated in FIG. 7B.

In the following, for ease of explanation, an image obtained by imaging the anterior segment of the right eye 44R with the right-eye inward-facing camera 48R is referred to as a right-eye anterior segment image, and an image obtained by imaging the anterior segment of the left eye 44L with the left-eye inward-facing camera 48L is referred to as a left-eye anterior segment image. When there is no need to discriminate between the right-eye anterior segment image and the left-eye anterior segment image in the description below, for ease of explanation they will be referred to simply as "anterior segment images".

Note that in the present exemplary embodiment the anterior segment of the left eye 44L is imaged by the left-eye inward-facing camera 48L, and the anterior segment of the right eye 44R is imaged by the right-eye inward-facing camera 48R at the frame rate of 60 fps (frames/second). Namely a video image is acquired with the anterior segment of the subject eye 44 as the imaging subject by the processing section 180 causing the left-eye inward-facing camera 48L and the right-eye inward-facing camera 48R to operate.

At step 217, the processing section 217 transmits adjustment instruction information to the wearable terminal device 12, and then processing transitions to step 218. Adjustment instruction information indicates here information to instruct the wearable terminal device 12 to adjust the position of the reflection mirror 42, to correct the laser beam optical axis, and to perform home positioning.

At step 218 (see FIG. 7B), the processing section 180 causes test audio to be output by the speaker 140 by performing wireless communication with the control device 18, and determines whether or not the audio of the speaker 140 is good. The test audio indicates, for example, audio of "PLEASE PRESS THE RESPONSE BUTTON WHEN YOU HEAR A SOUND" or the like. Thus, for example, whether or not the audio of the speaker 140 is good is determined by whether or not the response button 19 is pressed by the patient while the test audio is being output from the speaker 140.

Processing transitions to step 220 when negative determination is made at step 218, i.e. when the audio of the speaker 140 is not good. Processing transitions to step 222 when affirmative determination is made at step 218, i.e. when the audio of the speaker 140 is good.

At step 220, the processing section 180 determines whether or not the end condition relating to terminal management processing has been satisfied. Processing transitions to step 218 when negative determination is made at step 220, i.e. when the end condition relating to terminal management processing has not been satisfied. The terminal management processing is ended when affirmative determination is made at step 220, i.e. when the end condition relating to terminal management processing has been satisfied.

At step 222, the processing section 180 references the previously mentioned examination sequence information included in the patient information and the like received at step 208, and determines whether or not it is visual field tests that are to be performed alone from out of ophthalmic examinations. Processing transitions to step 226 when negative determination is made at step 222, i.e. when it is not the visual field tests that are to be performed alone from out of the ophthalmic examinations. Processing transitions to step 224 when affirmative determination is made at step 222, i.e. when it is the visual field tests that are to be performed alone from out of the ophthalmic examinations.

At step 224, the processing section 180 transmits visual field test instruction information to the wearable terminal device 12, and then processing transitions to step 236. Note that the visual field test instruction information indicates information instructing the wearable terminal device 12 to execute the visual field test processing (FIG. 9A and FIG. 9B), described later. Moreover, the visual field test instruction information encompasses the required information received at step 200, and the patient information and the like received by the wireless communication section 82 at step 208.

In the present exemplary embodiment, mark projection position information of plural marks for visual field test is incorporated in the terminal-side program 124A. The mark projection position information indicates information representing positions where marks are to be projected onto the retinas 46 (hereafter also referred to as "mark projection positions" or "projection positions"). Specific examples thereof include information to express the marks in a two-dimensional plane using XY coordinates and polar coordinates $r\theta$, and in three-dimensional space using XYZ coordinates and polar coordinates $r\theta_{\varphi}$.

The "marks" referred to here indicate, for example, marks sensed as white dots for normal retinas 46. The projection of the marks onto the retinas 46 is implemented by shining a laser beam of visible light.

Information indicating the brightness (intensity) of the laser beam may be combined with the mark projection position information, with the mark projection position information held for use in the visual field test. Combining the information about the projection position and the brightness enables information about the sensitivity of the retina to be obtained in visual field test.

Moreover, the mark projection position information of the plural marks in the terminal-side program 124A is employed by the control section 170 of the control device 18 to control the scanner 28. Namely, the laser beam is shone onto the positions (projection positions according to the mark projection position information) represented by the mark projection position information of the plural marks due to the scanner 28 being controlled by the control section 170 according to the mark projection position information of the plural marks.

For ease of explanation the positions where the marks are projected on to the retina 46 will be referred to below as "mark projection positions". The mark projection positions are an example of "identified positions" according to technology disclosed herein.

At step 226, the processing section 180 references the previously mentioned examination sequence information included in the patient information and the like received at step 208, and determines whether or not it is SLO image examinations that are to be performed alone from out of ophthalmic examinations. Processing transitions to step 230 when negative determination is made at step 224, i.e. when it is not the SLO image examinations that are to be performed alone from out of the ophthalmic examinations. Processing transitions to step 228 when affirmative determination is made at step 226, i.e. when it is the SLO image examinations that are to be performed alone from out of the ophthalmic examinations.

At step 228, the processing section 180 transmits SLO image examination instruction information to the wearable terminal device 12, and then processing transitions to step 236. Note that the SLO image examination instruction information indicates information to instruct the wearable terminal device 12 to execute SLO image examination processing (FIG. 9C), described later. The SLO image examination instruction information includes required information received at step 200, and patient information and the like received by the wireless communication section 82 at step 208.

At step 230, the processing section 180 references the previously mentioned examination sequence information included in the patient information and the like received at step 208, and determines whether or not it is OCT image examinations that are to be performed alone from out of ophthalmic examinations. Processing transitions to step 234 when negative determination is made at step 230, i.e. when it is not the OCT image examinations that are to be performed alone from out of the ophthalmic examinations. Processing transitions to step 232 when affirmative determination is made at step 230, i.e. when it is the OCT image examinations that are to be performed alone from out of the ophthalmic examinations.

At step 232, the processing section 180 transmits OCT image examination instruction information to the wearable terminal device 12, and then processing transitions to step 236. Note that the OCT image examination instruction information indicates information to instruct the wearable terminal device 12 to execute OCT image examination processing (FIG. 9D), described later. The OCT image examination instruction information includes required information received at step 200, and patient information and the like received by the wireless communication section 82 at step 208.

At step 234, the processing section 180 transmits successive examination instruction information to the wearable terminal device 12, and then processing transitions to step 236. Note that the successive examination instruction information indicates information to instruct the wearable terminal device 12 to execute successive examination processing (FIG. 8), described later. Successive examinations indicates, for example, a series of examinations performed in the sequence of a visual field test, then an SLO image examination, followed by an OCT image examination. The successive examination instruction information includes required information received at step 200, and the patient information and the like received by the wireless communication section 82 at step 208.

Note that although an example of successive examinations given in the present exemplary embodiment is of a series of examinations performed in the sequence of a visual field test, then an SLO image examination, followed by an OCT image examination, the technology disclosed herein is not limited thereto. The successive examination may, for example, be a combination of at least two or more examinations from out of visual field tests, SLO image examinations, and OCT image examinations.

At step 236, the acquisition section 182 determines whether or not the examination result information transmitted from the wearable terminal device 12 has been received by the wireless communication section 82. Note that the examination result information is transmitted from the wearable terminal device 12 by the processing of step 270 included in terminal-side processing, described later, executed by the processing section 171. The examination result information transmitted from the wearable terminal device 12 by the processing of step 270 included in terminal-side processing, described later, being executed by the processing section 171 indicates field-of-view defect map information, an SLO image, and/or an OCT image.

The field-of-view defect map information transmitted as the examination result information from the wearable terminal device 12 is generated by the processing of step 256V included in the visual field test processing, described later, being executed by the control section 170. The SLO image transmitted as the examination result information from the wearable terminal device 12 is obtained by performing SLO imaging on the retina 46 at step 262C and/or step 2621 illustrated in FIG. 9C. Furthermore, the OCT image transmitted as the examination result information from the wearable terminal device 12 is obtained by performing OCT imaging on the retina 46 at step 266C and/or step 2661 illustrated in FIG. 9D.

The SLO images are broadly divided into SLO low resolution images and SLO high resolution images. The SLO low resolution images are SLO images at low resolution, and are obtained by executing SLO low resolution imaging at step 262C illustrated in FIG. 9C. The SLO high resolution images are SLO images at high resolution, and are obtained by executing the SLO high resolution imaging at step 2621 illustrated in FIG. 9C. The SLO low resolution imaging indicates imaging of the retina 46 as the imaging subject at low resolution using SLO. The SLO high resolution imaging indicates imaging of the retina 46 as the imaging subject at high resolution using SLO.

The OCT images are broadly divided into OCT low resolution images and OCT high resolution images. The OCT low resolution images are OCT images at low resolution, and are obtained by executing the OCT low resolution imaging at step 266C illustrated in FIG. 9D. The OCT high resolution images are OCT images at high resolution, and are obtained by executing the OCT high resolution imaging at step 2661 illustrated in FIG. 9D. The OCT low resolution imaging indicates imaging of the retina 46 as the imaging subject at low resolution using OCT. The OCT high resolution imaging indicates imaging of the retina 46 as the imaging subject at high resolution using OCT.

Note that in the present exemplary embodiment "low resolution" has a wide image target area for each single pixel, and indicates a resolution obtained by imaging a fundus image in which each single pixel obtained covers a wide area. In contrast thereto, in the present exemplary embodiment "high resolution" has a narrow image target area for each single pixel, and indicates a resolution obtained by imaging a fundus image in which each single pixel obtained covers a narrow area. The "wide area" indicates, for example, a wider area than a predetermined area. Moreover, the "narrow area" indicates, for example, a narrower area than a predetermined area. Furthermore, a "high precision fundus image" indicates, for example, a fundus image having a higher precision than at least an image obtained by imaging at low resolution.

Processing transitions to step 242 when negative determination is made at step 236, i.e. when the examination result information transmitted from the wearable terminal device 12 is not received by the wireless communication section 82. Processing transitions to step 237 when affirmative determination is made at step 236, i.e. when the examination result information transmitted from the wearable terminal device 12 has been received by the wireless communication section 82.

At step 242, the processing section 180 determines whether or not the end condition relating to terminal management processing has been satisfied. Processing transitions to step 236 when negative determination is made at step 242, i.e. when the end condition relating to terminal management processing has not been satisfied. The terminal management processing is ended when affirmative determination is made at step 242, i.e. when the end condition relating to terminal management processing has been satisfied.

At step 237, the acquisition section 182 acquires the examination result information received by the wireless communication section 82 at step 236, and then processing transitions to step 238.

At step 238, the processing section 180 causes the right-eye inward-facing camera 48R and the left-eye inward-facing camera 48L to end imaging of the anterior segments of the subject eyes 44 by performing wireless communication with the control device 18, then processing transitions to step 240.

At step 240, the processing section 180 transmits the examination result information acquired by the acquisition section 182 at step 237 to the server device 15, and then ends the terminal management processing.

Figure 8:
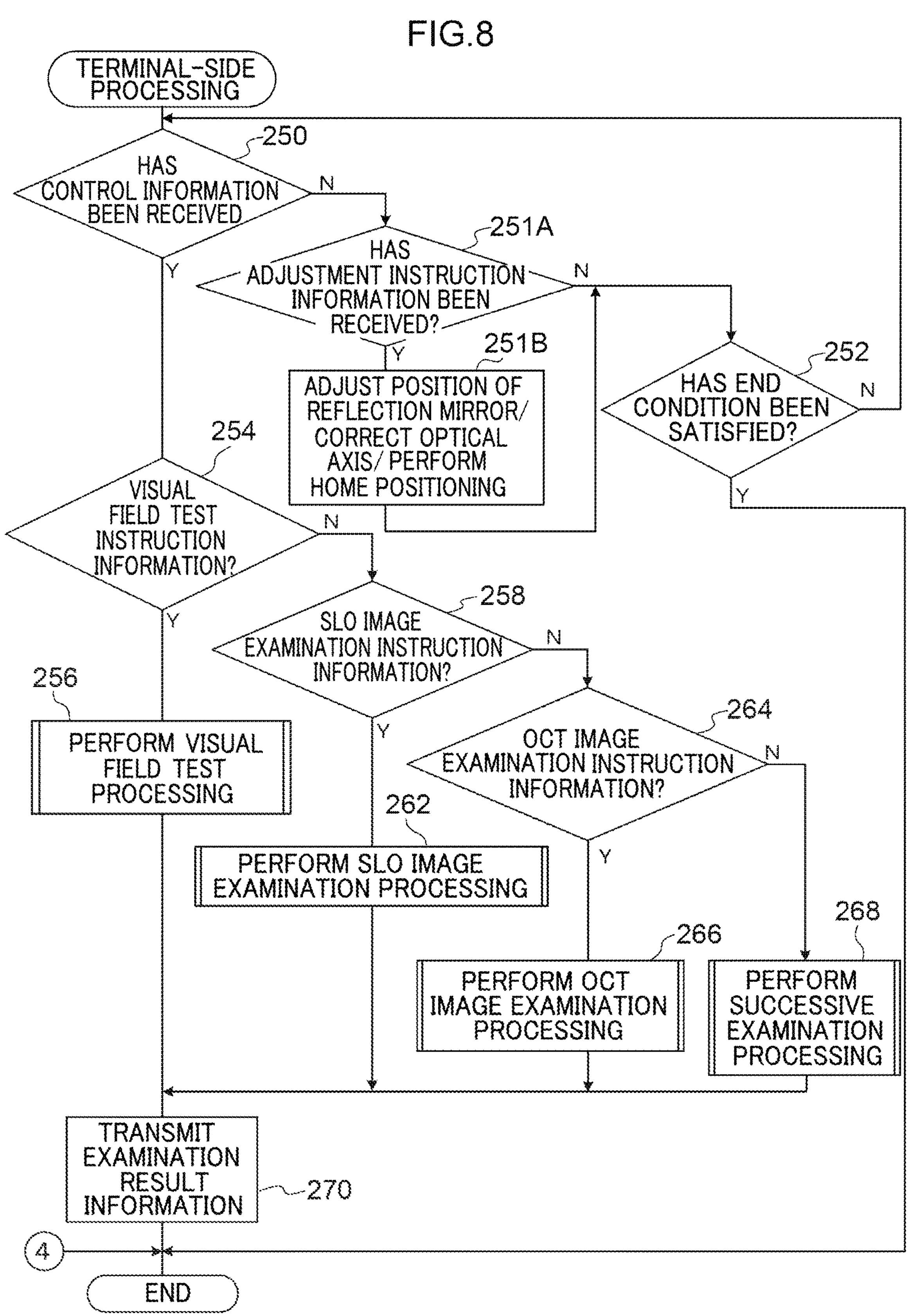
FIG. 8 is a flowchart illustrating an example of a flow of terminal management processing according to the first to third exemplary embodiments.

Next, explanation follows regarding the terminal-side processing implemented by the CPU 120 executing the terminal-side program 124A when the main power source (not illustrated in the drawings) for the wearable terminal device 12 is turned on, with reference to FIG. 8.

At step 250 in the terminal-side processing illustrated in FIG. 8, the processing section 171 determines whether or not the control information from the management device 14 has been received by the wireless communication section 112. The control information is information to control the control section 170, and is the previously mentioned visual field test instruction information, SLO image examination instruction information, OCT image examination instruction information, or successive examination instruction information.

Processing transitions to step 251 when negative determination is made at step 250, i.e. when the control information from the management device 14 has not been received by the wireless communication section 112. Processing transitions to step 254 when affirmative determination is made at step 250, i.e. when the control information from the management device 14 has been received by the wireless communication section 112.

At step 251A, the processing section 171 determines whether or not the adjustment instruction information, transmitted from the management device 14 by execution of the processing of step 217 included in the terminal management processing, has been received by the wireless communication section 112. Processing transitions to step 252 when negative determination is made at step 251A, i.e. when the adjustment instruction information has not been received by the wireless communication section 112. Processing transitions to step 251B when affirmative determination is made at step 251A, i.e. when the adjustment instruction information has been received by the wireless communication section 112.

Processing transitions to step 252 after the control section 170 has, at step 251B, performed adjustment of the position of the reflection mirror 42, correction of the optical axes of the laser beam, and home positioning.

In order to adjust the position of the reflection mirror 42, correct the optical axis of the laser beam, and perform home positioning at step 251B, first the inter-pupil distance is detected by the control section 170 based on the latest right-eye anterior segment image and the latest left-eye anterior segment image. Then, the adjustment of the position of the reflection mirror 42, correction of the optical axes of the laser beam, and home positioning is performed by the control section 170 based on the eyewear ID of the wearable terminal device 12, the detected inter-pupil distance, and the like. Note that the inter-pupil distance referred to here indicates the distance between the pupil in the anterior segment of the right eye 44R as represented in the right-eye anterior segment image and the pupil in the anterior segment of the left eye 44L as represented in the left-eye anterior segment image. Moreover, the position of the reflection mirror 42 is adjusted by the minor drive sources 72 being controlled by the control section 170. The correction of the optical axis of the laser beam and the home positioning is implemented by the scanner 28 being controlled by the control section 170.

At step 252, the processing section 171 determines whether or not the end condition relating to terminal-side processing has been satisfied. The end condition relating to terminal-side processing indicates a condition to end the terminal-side processing. Examples of the end condition relating to terminal-side processing include a condition that a specific period of time has elapsed, a condition that information has been received indicating that an end instruction from the management device 14, and/or a condition that a situation requiring the terminal-side processing to be forcibly ended has been detected by the CPU 120.

Processing transitions to step 250 when negative determination is made at step 252, i.e. when the end condition relating to terminal-side processing has not been satisfied. The terminal-side processing is ended when affirmative determination is made at step 252, i.e. when the end condition relating to terminal-side processing has been satisfied.

At step 254, the processing section 171 determines whether or not the control information received by the wireless communication section 112 at step 250 is the visual field test information. Processing transitions to step 258 when, at step 254, it transpires that the control information received by the wireless communication section 112 at step 250 is not the visual field test information. Processing transitions to step 256 when affirmative determination is made at step 254, i.e. when the control information received by the wireless communication section 112 at step 250 is the visual field test information.

Figure 9B:
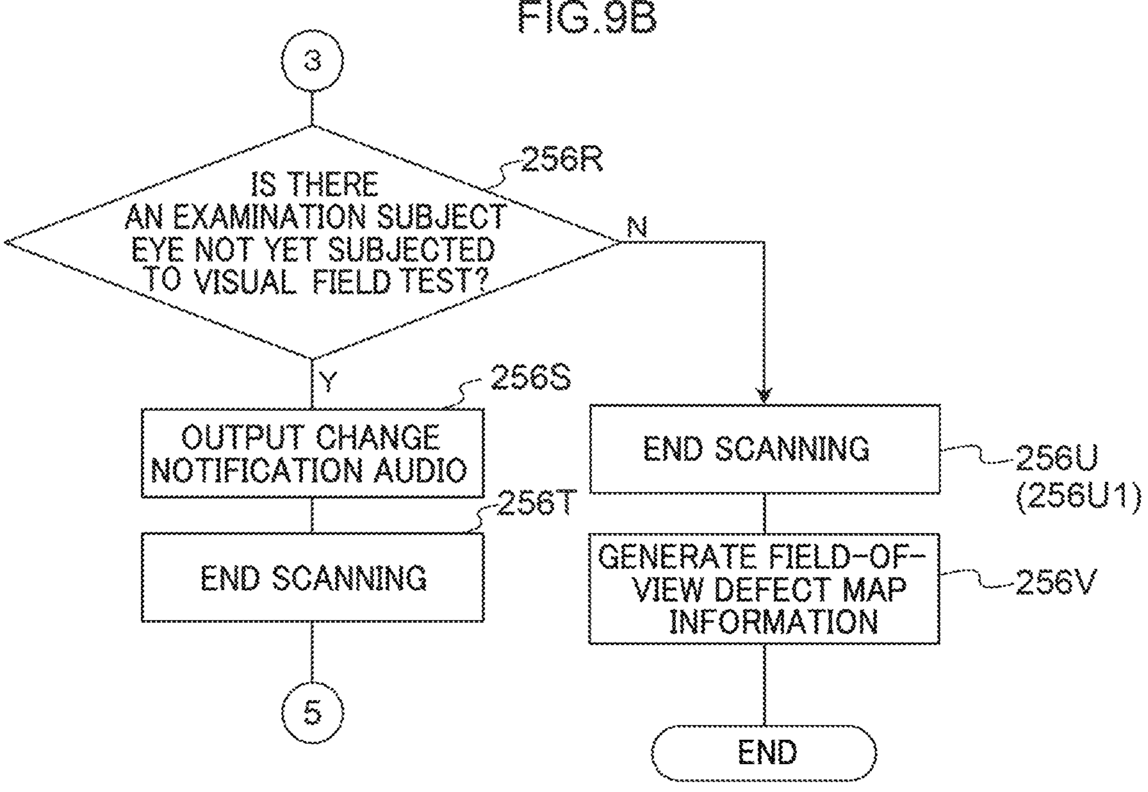
FIG. 9B is a continuation flowchart of the flowchart illustrated in FIG. 9A.

At step 256, the control section 170 executes the visual field test processing as illustrated in the example of FIG. 9A and FIG. 9B, and then processing transitions to step 270.

At step 258, the processing section 171 determines whether or not the control information received by the wireless communication section 112 at step 250 is the SLO image examination information. Processing transitions to step 264 when, at step 258, it transpires that the control information received by the wireless communication section 112 at step 250 is not the SLO image examination information. Processing transitions to step 262 when affirmative determination is made at step 258, i.e. when the control information received by the wireless communication section 112 at step 250 is the SLO image examination information.

At step 262, the control section 170 executes the SLO image examination processing in the example illustrated in FIG. 9C, and then processing transitions to step 270.

At step 264, the processing section 171 determines whether or not the control information received by the wireless communication section 112 at step 250 is the OCT image examination information. Processing transitions to step 268 when, at step 264, it transpires that the control information received by the wireless communication section 112 at step 250 is not the OCT image examination information. Processing transitions to step 266 when affirmative determination is made at step 264, i.e. when the control information received by the wireless communication section 112 at step 250 is the OCT image examination information.

Figure 9D:
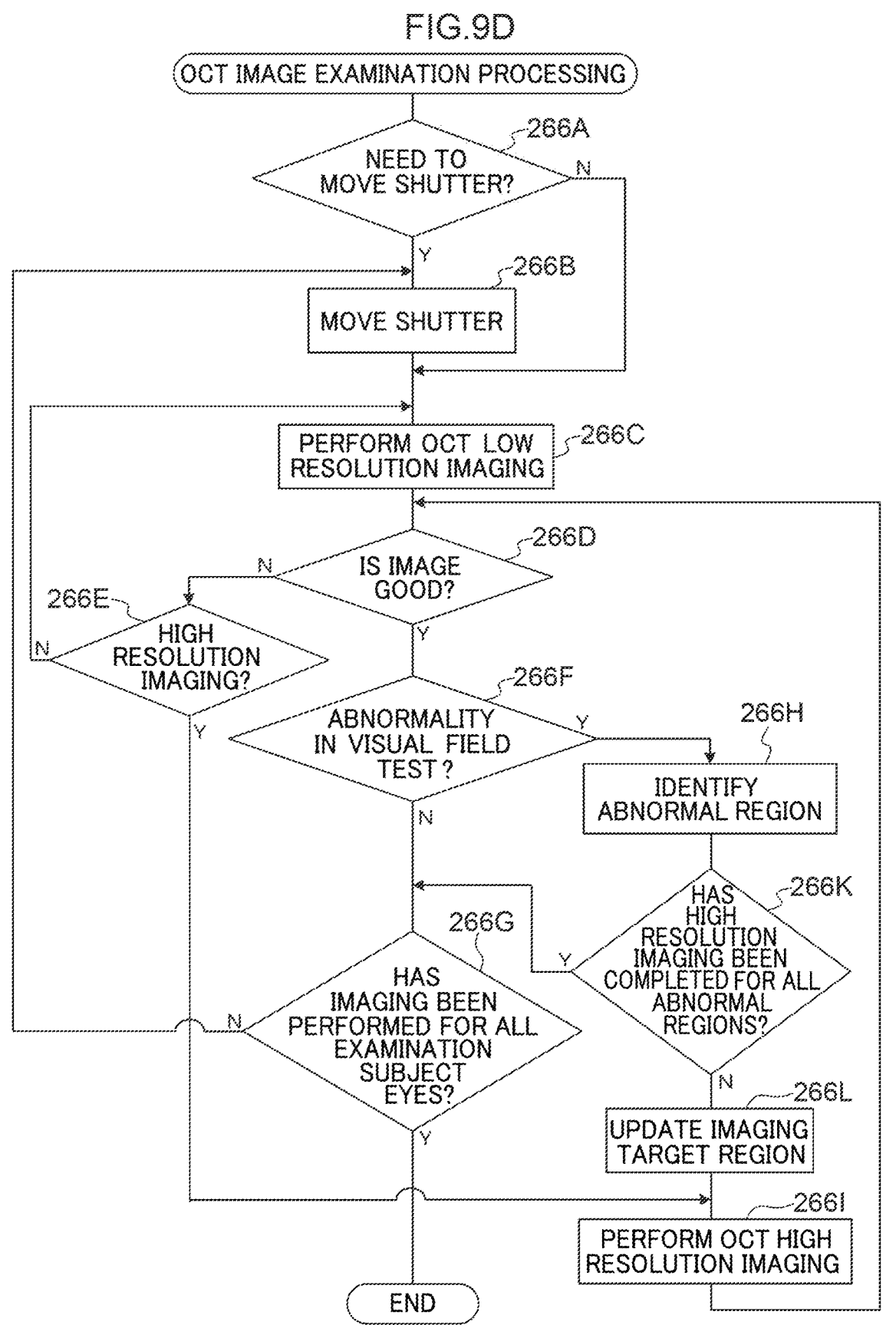

At step 266, the control section 170 executes the OCT image examination processing as illustrated in the example in FIG. 9D, and then processing transitions to step 270.

At step 268 the control section 170 executes the successive examination processing and then processing transitions to step 270. The successive examination processing executed at the present step 268 is, for example, processing in which the visual field test processing executed at step 256, the SLO image examination processing executed at step 262, and the OCT image examination processing executed at step 266 are executed in sequence.

Note that although an example of the successive examination processing is given here in which processing is executed in the sequence of the visual field test processing, then the SLO image examination processing, followed then by the OCT image examination processing, the technology disclosed herein is not limited thereto. For example, the successive examination processing may be performed by executing at least two types of processing from out of the visual field test processing, the SLO image examination processing, and the OCT image examination processing. Which combination of processing is executed from out of the visual field test processing, the SLO image examination processing, and the OCT image examination processing may be determined based on the previously mentioned patient information and the like included in successive examination information. More specifically, the combination of processing may be determined based on the previously mentioned examination sequence information included in the patient information and the like.

As illustrated in the example of FIG. 9A, at step 256A in the visual field test processing, the control section 170 determines whether or not a shutter 121 needs to be moved based on the examination subject eye instruction information in the previously mentioned required information included in the visual field test instruction information.

Processing transitions to step 256C when negative determination is made at step 256A, i.e. when there is no need to move the shutter 121. Processing transitions to step 256B when affirmative determination is made at step 256A, i.e. when there is a need to move the shutter 121.

At step 256B, the control section 170 moves the shutter 121 based on the examination subject eye instruction information in the previously mentioned required information included in the visual field test instruction information, and then processing transitions to step 256C.

At step 256C, the control section 170 causes the light management section 114 and the optical system 27 to start scanning the three primary color laser beam over the retina 46 of the examination subject eye, and then processing transitions to step 256D.

At step 256D, the control section 170 determines whether or not the three primary color laser beam has reached the mark projection position indicated by the mark projection position information for one mark out of the mark projection position information for plural marks in the terminal-side program 124A. At the present step 256D, the same mark projection position information is reused as the "mark projection position information for one mark" when this follows from affirmative determination being made at step 256M. Moreover, at the present step 256D, mark projection position information for an unused mark from out of the mark projection position information for plural marks is used as the "mark projection position information for one mark" when this follows from negative determination being made at step 256N.

In the present exemplary embodiment, although the sequence in which the mark projection position information for plural marks is used at the present step 256D is predetermined, the technology disclosed herein is not limited thereto. For example, mark projection position information instructed by a medical service professional via the management device 14 may be used at the present step 256D. Moreover, the sequence in which the mark projection position information is used at the present step 256D may be changeable by the medical service professional via the management device 14.

Processing transitions to step 256E when negative determination is made at step 256D, i.e. when the three primary color laser beam has not reached the mark projection position indicated by the mark projection position information for one mark out of the mark projection position information for plural marks in the terminal-side program 124A. Processing transitions to step 256F when affirmative determination is made at step 256D, i.e. when the three primary color laser beam has reached the mark projection position indicated by the mark projection position information for one mark out of the mark projection position information of the plural marks.

At step 256E, the control section 170 determines whether or not the end condition relating to terminal-side processing has been satisfied. Processing transitions to step 256D when negative determination is made at step 256E, i.e. when the end condition relating to terminal-side processing has not been satisfied. The terminal-side processing is ended when affirmative determination is made at step 256E, i.e. when the end condition relating to terminal-side processing has been satisfied.

At step 256F, the control section 170 projects the mark onto the retina 46 by controlling the laser light source unit 113 through the light source control circuit 115, and then processing transitions to step 256G. Note that the position where the mark is projected refers here to a mark projection position indicated by the latest mark projection position information employed at step 256D.

At step 256G, the control section 170 determines whether or not the response button 19 has been pressed. Whether or not the response button 19 has been pressed is determined by whether or not a response signal has been input from the response button 19.

Processing transitions to step 256H when negative determination is made at step 256G, i.e. when the response button 19 has not been pressed. Processing transitions to step 256J when affirmative determination is made at step 256G, i.e. when the response button 19 has been pressed.

At step 256J, the control section 170 stores the latest mark projection position information in the primary storage section 122, and then processing transitions to step 256K. The latest mark projection position information referred to here indicates the latest mark projection position information used at step 256D, in other words indicates the mark projection position information for the mark being projected onto the retina 46 at the timing when the response button 19 was pressed.

At step 256H, the control section 170 determines whether or not a predetermined period of time (for example, 2 seconds) has elapsed from when the processing of step 256F was executed. Processing transitions to step 256G when negative determination is made at step 256H, i.e. when the predetermined period of time has not elapsed from when the processing of step 256F was executed. Processing transitions to step 2561 when affirmative determination is made at step 256H, i.e. when the predetermined period of time has elapsed from when the processing of step 256F was executed.

At step 2561, the control section 170 determines whether or not the end condition relating to terminal-side processing has been satisfied. Processing transitions to step 256K when negative determination is made at step 2561, i.e. when the end condition relating to terminal-side processing has not been satisfied. The terminal-side processing is ended when affirmative determination is made at step 2561, i.e. when the end condition relating to terminal-side processing has been satisfied.

At step 256K, the control section 170 determines whether or not the gaze of the patient has wandered from the fixation target. The determination as to whether or not the gaze of the patient has wandered from the fixation target is determined based on the latest anterior segment image.

Processing transitions to step 256L when affirmative determination is made at step 256K, i.e. when the gaze of the patient has wandered from the fixation target. Processing transitions to step 256N when negative determination is made at step 256K, i.e. when the gaze of the patient has not wandered from the fixation target.

At step 256L, the control section 170 causes the speaker 140 to output gaze guiding audio, and then processing transitions to step 256M.

The gaze guiding audio indicates audio to guide the gaze in a direction toward the fixation target. The gaze guiding audio is generated according to the positional relationship between the gaze and the fixation target. The position of the gaze may be identified based on the latest anterior segment image. Examples of the gaze guiding audio include audio content of "PLEASE LOOK AT THE FIXATION TARGET", audio content of "A LITTLE BIT MORE TO THE RIGHT, PLEASE", etc.

At step 256M, the control section 170 determines whether or not wandering of the gaze of the patient from the fixation target has been eliminated. Determination as to whether or not wandering of the gaze of the patient from the fixation target has been eliminated is determined based on the latest anterior segment image.

Processing transitions to step 256L when negative determination is made at step 256M, i.e. when wandering of the gaze of the patient from the fixation target has not been eliminated. Processing transitions to step 256D when affirmative determination is made at step 256M, i.e. when wandering of the gaze of the patient from the fixation target has been eliminated.

At step 256N, the control section 170 determines whether or not marks have been projected onto all of the mark projection positions. Processing transitions to step 256N when negative determination is made at step 256N, i.e. when marks have not yet been projected onto all of the mark projection positions. Processing transitions to step 256R of FIG. 9B when affirmative determination is made at step 256N, i.e. when marks have been projected onto all of the mark projection positions.

At step 256R, the control section 170 determines whether or not there is still an examination subject eye that has not yet been subjected to the visual field test. Determination as to whether or not there is still an examination subject eye that has not yet been subjected to the visual field test is determined based on the examination subject eye instruction information in the previously mentioned required information included in the visual field test instruction information and based on the current position of the shutter 121.

Processing transitions to step 256S when affirmative determination is made at step 256R, i.e. when there is still an examination subject eye that has not yet been subjected to the visual field test. Processing transitions to step 256U when negative determination is made at step 256R, i.e. when there is not an examination subject eye that has not yet been subjected to the visual field test.

At step 256S, the control section 170 causes change notification audio to be output by the speaker 140, and then processing transitions to step 256T. The change notification audio indicates audio to notify the patient of a change to the examination subject eye. An example of the change notification audio is audio content of "THE VISUAL FIELD TEST FOR THE RIGHT EYE IS NOW COMPLETE AND THE VISUAL FIELD TEST WILL NOW BE PERFORMED ON THE LEFT EYE".

At step 256T, the control section 170 controls the light management section 114 and the optical system 27 so as to cause the light management section 114 and the optical system 27 to stop scanning of the three primary color laser beam on the retina 46 of the examination subject eye, and then processing transitions to step 256B.

At step 256U, the control section 170 controls the light management section 114 and the optical system 27 so as to cause the light management section 114 and the optical system 27 to stop scanning of the three primary color laser beam on the retina 46 of the examination subject eye, and then processing transitions to step 256V.

At step 256V, the control section 170 generates field-of-view defect map information based on the mark projection position information stored in the primary storage section 122 by executing the processing of step 256J, and then ends the visual field test processing. Note that the field-of-view defect map information indicates information including the patient ID, information to draw field-of-view defect map, an image of a field-of-view defect map, and the like. The field-of-view defect map indicates a map enabling the identification of defective sites in the field of view of the patient. A field-of-view defect map 240 is displayed in an image display region 190B3 of the second state-of-progress screen 190B illustrated in FIG. 14. In the field-of-view defect map 240, defective sites and normal sites are represented by the tone of a gray scale, with the principle defective sites being displayed in black.

Note that a configuration may be adopted in which, not only is the field-of-view defect map 240 generated by the wearable terminal device 12 or the management device 14, but a field-of-view defect map is plotted in advance by the server device 15 so as to generate the visual field test result report. Moreover, for example, a configuration may be adopted in which, the field-of-view defect map is not generated with only the field-of-view defect map information for the same patient (patient having the same patient ID), but a field-of-view defect area is displayed in overlay on a fundus image, or a field-of-view defect area is displayed in overlay on a 3D-OCT image.

Explanation now follows regarding the SLO image examination processing illustrated in FIG. 9C. Note that for ease of explanation, the assumption will be made in the description that the visual field test processing has been executed previously to the SLO image examination processing illustrated in FIG. 9C.

As illustrated in the example of FIG. 9C, at step 262A in the SLO image examination processing, the control section 170 determines whether or not a shutter 121 needs to be moved based on the examination subject eye instruction information in the previously mentioned required information included in the SLO image examination information.

Processing transitions to step 262C when negative determination is made at step 262A, i.e. when there is no need to move the shutter 121. Processing transitions to step 262B when affirmative determination is made at step 262A, i.e. when there is a need to move the shutter 121.

At step 262B, the control section 170 moves the shutter 121 based on the examination subject eye instruction information in the previously mentioned required information included in the SLO image examination instruction information, and then processing transitions to step 262C.

At step 262C, the control section 170 executes the SLO low resolution imaging, and then processing transitions to step 262D. At the present step 262C, for example, a range determined by default (for example, a range determined in advance) may be employed as the imaging target region for the SLO low resolution imaging.

At step 262D, the control section 170 determines whether or not the SLO image is good. Processing transitions to step 262E when negative determination is made at step 262D, i.e. when the SLO image is not good. Processing transitions to step 262F when affirmative determination is made at step 262D, i.e. when the SLO image is good.

At step 262E, the control section 170 determines whether or not the SLO image that is subjected to determination at step 262D is an SLO high resolution image. Processing transitions to step 262C when negative determination is made at step 262E, i.e. when the SLO image subjected to determination at step 262D is an SLO low resolution image. Processing transitions to step 2621 when affirmative determination is made at step 262E, i.e. when the SLO image subjected to determination at step 262D is an SLO high resolution image.

At step 262F, the control section 170 determines whether or not there is an abnormality in the visual field test. Namely, whether or not there is an abnormality in the visual field test is determined based on the field-of-view defect map information generated by execution of the processing of step 256V included in the visual field test processing illustrated in FIG. 9B.

Processing transitions to step 262G when negative determination is made at step 262F, i.e. when there was no abnormality in the visual field test. Processing transitions to step 262H when affirmative determination is made at step 262F, i.e. when there was an abnormality in the visual field test.

At step 262G, the control section 170 determines whether or not the SLO low resolution imaging has been executed for all of the examination subject eyes based on the examination subject eye instruction information in the previously mentioned required information included in the visual field test instruction information. Processing transitions to step 262B when negative determination is made at step 262G, i.e. when the SLO low resolution imaging has not yet been executed for all of the examination subject eyes. The SLO image examination processing is ended when affirmative determination is made at step 262G, i.e. when the SLO low resolution imaging has been executed for all of the examination subject eyes.

At step 262H, the control section 170 identifies one or more abnormal regions based on the field-of-view defect map, and then processing transitions to step 262K. The abnormal region at the present step 262H and at step 266H, described later (see FIG. 9D), indicates, for example, a specific range including a region out of the total region of the retina 46 that is determined to "have an abnormality" in the field-of-view defect map. Note that the field-of-view defect map employed in the processing of the present step 262H is included in the field-of-view defect map information generated by the execution of the processing of step 256V included FIG. 9B.

At step 262K, the control section 170 determines whether or not the SLO high resolution imaging at step 2621, described later, has been completed for all of the abnormal regions identified at step 262H. Processing transitions to step 262G when affirmative determination is made at step 262K, i.e. when the SLO high resolution imaging at step 2621, described later, has been completed for all of the abnormal regions identified at step 262H. Processing transitions to step 262L when negative determination is made at step 262K, i.e. when the SLO high resolution imaging at step 2621, described later, has not been completed for all of the abnormal regions identified at step 262H.

At step 262L, the control section 170 updates the latest imaging target region with the imaging target region currently being employed, and then processing transitions to step 2621. At the present step 262L, the latest imaging target region indicates, for example, a region including a region from out of the total region of the retina 46 identified as being an abnormal region by execution of the processing of step 262H.

At step 2621, the control section 170 executes the SLO high resolution imaging, and then ends the SLO image examination processing. Note that the imaging target region for the SLO high resolution imaging is an imaging target region updated by execution of the processing of step 262L.

Explanation follows regarding the OCT image examination processing illustrated in FIG. 9D. Note that for ease of explanation, the assumption will be made in the description that the visual field test processing has been executed previously to the OCT image examination processing illustrated in FIG. 9D.

At step 266A in the OCT image examination processing illustrated in FIG. 9D, the control section 170 determines whether or not a shutter 121 needs to be moved based on the examination subject eye instruction information in the previously mentioned required information included in the OCT image examination information.

Processing transitions to step 266C when negative determination is made at step 266A, i.e. when there is no need to move the shutter 121. Processing transitions to step 266B when affirmative determination is made at step 266A, i.e. when there is a need to move the shutter 121.

At step 266B, the control section 170 moves the shutter 121 based on the examination subject eye instruction information in the previously mentioned required information included in the OCT image examination instruction information, and then processing transitions to step 266C.

At step 266C, the control section 170 executes the OCT low resolution imaging and then processing transitions to step 266D. At the present step 266C, for example, a range determined by default (for example, a range determined in advance) may be employed as the imaging target region for the OCT low resolution imaging.

At step 266D, the control section 170 determines whether or not the OCT image is good. Processing transitions to step 266E when negative determination is made at step 266D, i.e. when the OCT image is not good. Processing transitions to step 266F when affirmative determination is made at step 266D, i.e. when the OCT image is good.

At step 266E, the control section 170 determines whether or not the OCT image that is subjected to determination at step 266D is an OCT high resolution image. Processing transitions to step 266C when negative determination is made at step 266E, i.e. when the OCT image subjected to determination at step 266D is an OCT low resolution image. Processing transitions to step 2661 when affirmative determination is made at step 266E, i.e. when the OCT image subjected to determination at step 266D is an OCT high resolution image.

At step 266F, the control section 170 determines whether or not there is an abnormality in the visual field test. Namely, whether or not there is an abnormality in the visual field test is determined based on the field-of-view defect map information generated by execution of the processing of step 256V included in the visual field test processing illustrated in FIG. 9B.

Processing transitions to step 266G when negative determination is made at step 266F, i.e. when there is no abnormality in the visual field test. Processing transitions to step 266H when affirmative determination is made at step 266F, i.e. when there is an abnormality in the visual field test.

At step 266G, the control section 170 determines whether or not the OCT low resolution imaging has been executed for all of the examination subject eyes based on the examination subject eye instruction information in the previously mentioned required information included in the visual field test instruction information. Processing transitions to step 266B when negative determination is made at step 266G, i.e. when the OCT low resolution imaging has not yet been executed for all of the examination subject eyes. The OCT image examination processing is ended when affirmative determination is made at step 266G, i.e. when the OCT low resolution imaging has been executed for all of the examination subject eyes.

At step 266H, the control section 170 identifies one or more abnormal regions based on the field-of-view defect map, and then processing transitions to step 266K.

At step 266K, the control section 170 determines whether or not the OCT high resolution imaging at step 2661, described later, has been completed for all of the abnormal regions identified at step 266H. Processing transitions to step 266G when affirmative determination is made at step 266K, i.e. when the OCT high resolution imaging at step 2661, described later, has been completed for all of the abnormal regions identified at step 266H. Processing transitions to step 266L when negative determination is made at step 266K, i.e. when the OCT high resolution imaging at step 2661, described later, has not been completed for all of the abnormal regions identified at step 266H.

At step 266L, the control section 170 updates the latest imaging target region with the imaging target region currently being employed, and then processing transitions to step 2661. At the present step 266L, examples of the latest imaging target region include a tomographic region in the thickness direction of the retina 46 identified by a first line, and a tomographic region in the thickness direction of the retina 46 identified by a second line, in a region including a region from out of the total region of the retina 46 identified as being an abnormal region by execution of the processing of step 266H. The first line indicates a line of a specific length cutting across a center line of an abnormal region. The second line indicates a line of a specific length perpendicular to the first line.

At step 2661, the control section 170 executes the OCT high resolution imaging, and then ends the OCT image examination processing. Note that the imaging target region for the OCT high resolution imaging is an imaging target region updated by execution of the processing of step 266L.

At step 270 illustrated in FIG. 8, the processing section 171 transmits the previously mentioned examination result information (the field-of-view defect map information, the SLO image, and/or the OCT image) to the management device 14 through the wireless communication section 112, and then ends the terminal-side processing.

Next, explanation follows regarding server-side processing implemented by the CPU 160 executing the server-side program 164B when power is turned on to a main power source (not illustrated in the drawings) of the server device 15, with reference to FIG. 10.

In the server-side processing illustrated in FIG. 10, the CPU 160 first determines at step 255A whether or not management device information has been received. The management device information indicates information transmitted to the server device 15 by the terminal management processing being executed by the CPU 90 of the management device 14.

Processing transitions to step 255F when negative determination is made at step 255A, i.e. when the management device information has not been received. Processing transitions to step 255B when affirmative determination is made at step 255A, i.e. when the management device information has been received.

At step 255B, the CPU 160 determines whether or not the management device information received at step 255A is the transmission request information. Processing transitions to step 255D when negative determination is made at step 255B, i.e. when the management device information received at step 255A is not the transmission request information, namely, when the management device information received at step 255A is the field-of-view defect map information. Processing transitions to step 255E when affirmative determination is made at step 255B, i.e. when the management device information received at step 255A is the transmission request information.

At step 255D, the CPU 160 generates a visual field test result report that is a report to indicate the results of the visual field test based on the field-of-view defect map information, stores the generated visual field test result report in the secondary storage section 164, and then transitions processing to step 255F. The generated visual field test result report is, for example, transmitted to an external device, such as the viewer 17 or the like when requested by the viewer 17 or the like.

At step 255E, the CPU 160 transmits the previously mentioned patient information and the like to the management device 14, and then transitions processing to step 255F. The patient information 164A included in the patient information and the like is acquired from the secondary storage section 164. The examination sequence information included in the patient information and the like is, for example, generated according to an instruction received by the reception device 154, or is acquired through the external OF 158 from an external device such as a USB memory, personal computer, and/or server device or the like.

At step 255F, the CPU 160 determines whether or not the end condition relating to server-side processing has been satisfied. The end condition relating to server-side processing indicates a condition to end the server-side processing. Examples of the end condition relating to server-side processing include a condition that a specific period of time has elapsed, a condition that the reception device 154 has received an end instruction, and/or a condition that a situation requiring the server-side processing to be forcibly ended has been detected by the CPU 160.

Processing transitions to step 255F when negative determination is made at step 255F, i.e. when the end condition relating to server-side processing has not been satisfied. The server-side processing is ended when affirmative determination is made at step 258, i.e. when the end condition relating to server-side processing has been satisfied.

Figure 11:
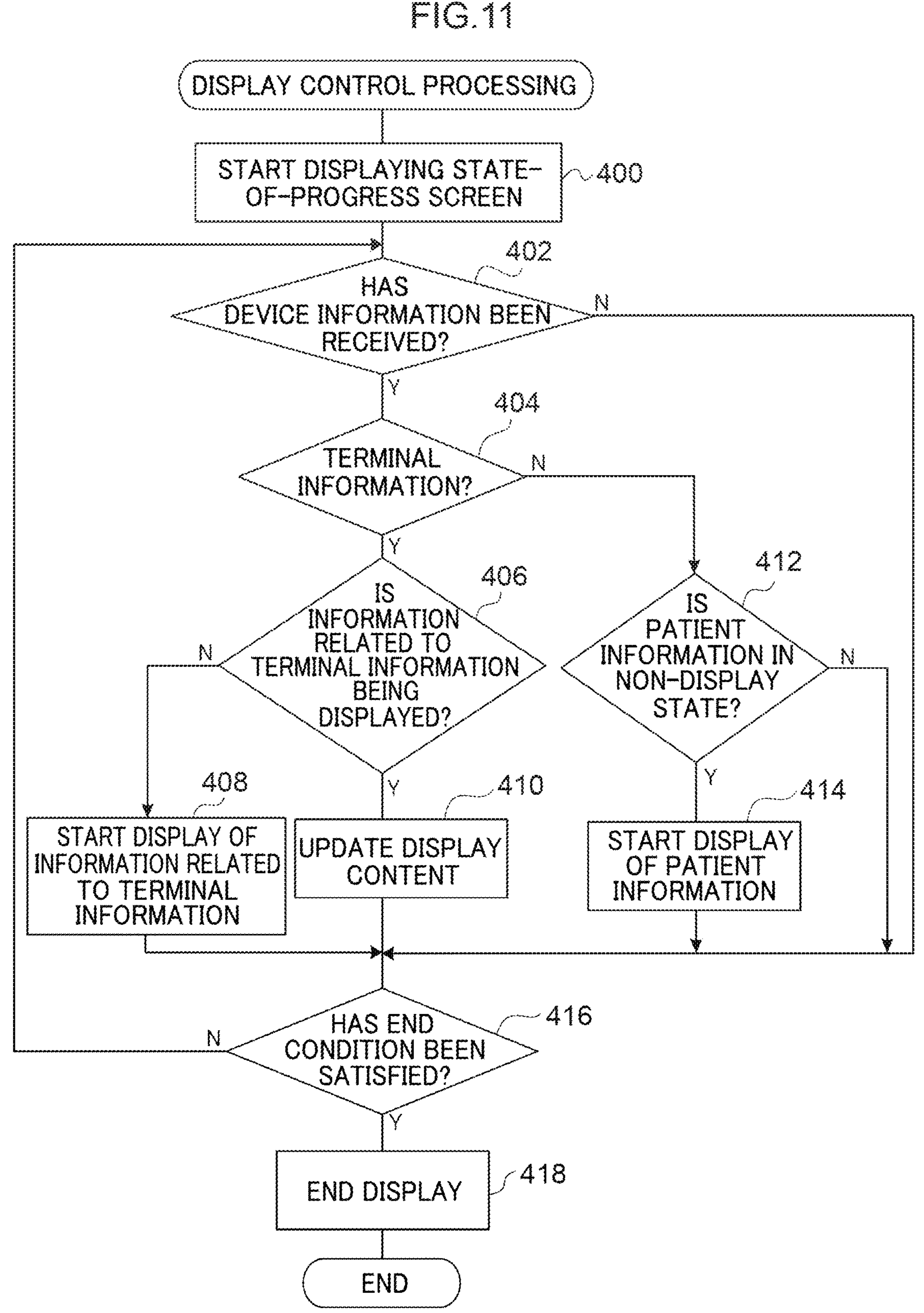
FIG. 11 is a flowchart illustrating an example of a flow of display control processing according to the first to third exemplary embodiments.

Explanation next follows regarding the display control processing implemented by the CPU 90 executing the display control program 94B by starting to execute the terminal management processing, with reference to FIG. 11.

In the following description, for ease of explanation, all of the required information will be assumed to have been received by the reception device 84 through the execution of the processing of step 200 included in the terminal management processing illustrated in FIG. 7A.

Moreover, in the following description, for ease of explanation, the management device 14 will be assumed to be capable of managing a maximum of six of the wearable terminal devices 12. Note that six devices is merely an example of the number of devices, and configurations that have various maximum numbers of manageable devices may be adopted. Furthermore, in the following, for ease of explanation, an example will be described in which there is an assumption that a state of communication has been established between the management device 14 and the six wearable terminal devices 12, and that the display control processing is for one of the wearable terminal devices 12 from out of the six wearable terminal devices 12.

Moreover, when there is no need to discriminate in the description between low resolution simultaneous imaging and high resolution simultaneous imaging, these will be referred to as “simultaneous imaging”. Moreover, when there is no need to discriminate in the description between SLO low resolution simultaneous imaging and SLO high resolution simultaneous imaging, these will be referred to as “SLO simultaneous imaging”. Moreover, when there is no need to discriminate in the description between OCT low resolution simultaneous imaging and OCT high resolution simultaneous imaging, these will be referred to as “OCT simultaneous imaging”.

Furthermore, when there is no need to discriminate in the description between SLO low resolution images and SLO high resolution images, these will be referred to as "SLO images", and when there is no need to discriminate in the description between OCT low resolution images and OCT high resolution images, these will be referred to as "OCT images".

At step 400 of the display control processing illustrated in FIG. 11, the display control section 184 causes the display 86A to start to display the state-of-progress screen 190, as illustrated in the example of FIG. 13, and then processing transitions to step 402.

At step 402, the display control section 184 determines whether or not the device information has been received. Reference here to "device information" indicates terminal information transmitted from the processing section 171 of the wearable terminal device 12 through the wireless communication section 112 by communication performed with the wearable terminal devices 12, patient information transmitted from the server device 15 by communication performed with the server device 15, and the like. The terminal information is information related to the wearable terminal device 12. The information related to the wearable terminal device 12 indicates, for example, information related to the state of progress of ophthalmic examination. The information related to the state of progress of ophthalmic examination includes the latest anterior segment image, state-of-progress information indicating the state of progress of visual field test, and eyewear worn/not-worn information indicating whether or not the patient is wearing the eyewear terminal device 16 correctly. Moreover, in the eyewear terminal device 16, an SLO image is included in the device information when SLO imaging has been performed. Moreover, in the eyewear terminal device 16, an OCT image is included in the device information when OCT imaging has been performed.

Processing transitions to step 416 when negative determination is made at step 402, i.e. when the device information has not been received. Processing transitions to step 404 when affirmative determination is made at step 402, i.e. when the device information has been received.

At step 404, the display control section 184 determines whether or not the received device information is the terminal information. Processing transitions to step 412 when negative determination is made at step 404, i.e. when the received device information is not the terminal information, namely, when the received device information is the patient information 164A. Processing transitions to step 406 when affirmative determination is made at step 404, i.e. when the received device information is terminal information.

At step 406, the display control section 184 determines whether or not information related to the received terminal information is being displayed on the state-of-progress screen 190. Processing transitions to step 408 when negative determination is made at step 406, i.e. when the information related to the received terminal information is not being displayed on the state-of-progress screen 190. Processing transitions to step 410 when affirmative determination is made at step 406, i.e. when the information relating to the received terminal information is being displayed on the state-of-progress screen 190.

At step 408, the display control section 184 causes the display 86A to start displaying the information related to the terminal information, and then processing transitions to step 416. The information related to the terminal information is thereby displayed on the state-of-progress screen 190.

As illustrated in the example of FIG. 13, the first state-of-progress screen 190A includes a terminal ID display region 190A1, a state-of-progress display region 190A2, an image display region 190A3, an eyewear wearing state display region 190A4, and a patient information display region 190A5. Information related to the terminal information is displayed in the terminal ID display region 190A1, the state-of-progress display region 190A2, the image display region 190A3, and the eyewear wearing state display region 190A4, and the patient information 164A is displayed in the patient information display region 190A5. Moreover, information based on the examination subject eye instruction information and the like is displayed in the state-of-progress display region 190A2.

A terminal ID enabling unique identification of a first wearable terminal device 12 from out of the six wearable terminal devices 12 with established communication with the management device 14 is displayed in the terminal ID display region 190A1. In the present exemplary embodiment an eyewear ID of the eyewear terminal device 16 corresponding to the received terminal information is employed as the terminal ID.

The state of progress of visual field test is mainly displayed in the state-of-progress display region 190A2. In the example thereof illustrated in FIG. 13, information content of "VISUAL FIELD TEST SUBJECT: BOTH EYES" is displayed as information enabling the visual field test subject eyes to be identified, information content of "LEFT EYE: PERFORMING OCT IMAGING" is displayed as information enabling the current examination status to be identified, and an indicator indicating the state of progress is displayed. The indicator is displayed in the state-of-progress display region 190A2 at a being-examined position. Moreover, information content of "EXAMINATION CONTENT: FIELD OF VIEW/SLO/OCT" is displayed in the state-of-progress display region 190A2 as an example of information based on the examination subject eye instruction information and the like. Information content of "EXAMINATION SUBJECT: BOTH EYES" is also displayed to indicate the examination subject eyes in the state-of-progress display region 190A2 as an example of information based on the examination subject eye instruction information.

An anterior segment image, an SLO image, an OCT image, and/or the field-of-view defect map 240 are displayed in the image display region 190A3 as subject eye feature information expressing features of the subject eye 44. Similar also applies to the image display regions 190B3, 190C3, 190D3, 190F3, described later.

The patient's latest anterior segment image identified by the patient information 164A being displayed in the patient information display region 190A5 is displayed in the image display region 190A3. The patient identified by the patient information 164A being displayed in the patient information display region 190A5 indicates, in other words, the patient who is currently using the wearable terminal device 12 identified by the terminal ID being displayed in the terminal ID display region 190A1. In the example illustrated in FIG. 13, the right-eye anterior segment image and the left-eye anterior segment image are displayed, with the anterior segment image of the left-eye that is not the examination subject eye displayed grayed out.

Information indicating whether or not the eyewear terminal device 16 is being worn by the patient is displayed in the eyewear wearing state display region 190A4. In the example illustrated in FIG. 13, information content of "BEING WORN" is displayed to indicate that the eyewear terminal device 16 is being worn by the patient. The background color of the eyewear wearing state display region 190A4 changes according to the state of progress. For example, the background color is a white, yellow, pink, or gray color. White indicates a state prior to the visual field test, yellow indicates a state during the visual field test, pink indicates that the visual field test has been completed, and gray indicates an examination subject eye has not yet been instructed for the visual field test.

In the example illustrated in FIG. 13, the first state-of-progress screen 190A is a screen corresponding to the wearable terminal device 12 including the eyewear terminal device 16 for which the terminal ID is "EA". The second state-of-progress screen 190B is a screen corresponding to the wearable terminal device 12 including the eyewear terminal device 16 for which the terminal ID is "EC". The third state-of-progress screen 190C is a screen corresponding to the wearable terminal device 12 including the eyewear terminal device 16 for which the terminal ID is "YV". The fourth state-of-progress screen 190D is a screen corresponding to the wearable terminal device 12 including the eyewear terminal device 16 for which the terminal ID is "MI". Moreover, the fifth state-of-progress screen 190E is a screen corresponding to the wearable terminal device 12 including the eyewear terminal device 16 for which the terminal ID is "GZ". Furthermore, the sixth state-of-progress screen 190E is a screen corresponding to the wearable terminal device 12 including the eyewear terminal device 16 for which the terminal ID is "YW".

The second state-of-progress screen 190B includes a terminal ID display region 190B1, a state-of-progress display region 190B2, an image display region 190B3, an eyewear wearing state display region 190B4, and a patient information display region 190B5.

In the example illustrated in FIG. 13, a terminal ID enabling unique identification of a second wearable terminal device 12 from out of the six wearable terminal devices 12 with established communication with the management device 14 is displayed in the terminal ID display region 190B1. Information content of "LEFT EYE: PERFORMING OCT IMAGING" is displayed in the state-of-progress display region 190B2 to indicate that OCT imaging is being performed on the left eye 44L. Information content of "LEFT EYE: PERFORMING OCT IMAGING" is displayed in the state-of-progress display region 190B2 to indicate that OCT imaging is being performed on the left eye 44L. Moreover, information content of "EXAMINATION CONTENT: FIELD OF VIEW/SLO/OCT" is displayed in the state-of-progress display region 190B2 to indicate the content and sequence of examination. Information content of "BOTH EYES" is also displayed to indicate the examination subject eyes in the state-of-progress display region 190B2. An indicator is displayed in the state-of-progress display region 190B2 at an examination-completed position.

Moreover, the field-of-view defect map 240 related to the subject eye 44, the SLO image related to the retina 46, the OCT image related to the retina 46R, and the left-eye anterior segment image are displayed in the image display region 190B3. Moreover, information content of "NOT BEING WORN" is displayed in the eyewear wearing state display region 190B4 as information to indicate that the eyewear terminal device 16 is being worn by the patient.

The third state-of-progress screen 190C includes a terminal ID display region 190C1, a state-of-progress display region 190C2, an image display region 190C3, an eyewear wearing state display region 190C4, and a patient information display region 19005.

In the example illustrated in FIG. 13, a terminal ID enabling unique identification of a third wearable terminal device 12 from out of the six wearable terminal devices 12 with established communication with the management device 14 is displayed in the terminal ID display region 190C1. Information content of "LEFT EYE: PERFORMING SLO IMAGING" is displayed in the state-of-progress display region 190B2 to indicate that SLO imaging is being performed on the left eye 44L. Moreover, information content of "EXAMINATION CONTENT: FIELD OF VIEW/SLO" is displayed in the state-of-progress display region 190C2 to indicate the content and sequence of examination. Information content of "LEFT EYE ONLY" is also displayed to indicate the examination subject eye in the state-of-progress display region 190C2. An indicator is displayed in the state-of-progress display region 190C2 at a being-examined position. The field-of-view defect map 240 for the left eye 44L and the left-eye anterior segment image are displayed in the image display region 190C3.

Information content of "BEING WORN" and information content of "ERROR" are also displayed in the eyewear wearing state display region 190C4 as information to indicate that the eyewear terminal device 16 is being worn by a patient. Note that the display of the information content of "ERROR" is implemented by execution of error processing of step 452, described later.

The fourth state-of-progress screen 190D includes a terminal ID display region 190D1, a state-of-progress display region 190D2, an image display region 190D3, an eyewear wearing state display region 190D4, and a patient information display region 190D5.

In the example illustrated in FIG. 13, a terminal ID enabling unique identification of a fourth wearable terminal device 12 from out of the six wearable terminal devices 12 with established communication with the management device 14 is displayed in the terminal ID display region 190D1. Information content of "UNDER AUDIO GUIDANCE" is displayed in the state-of-progress display region 190D2. The "UNDER AUDIO GUIDANCE" indicates, for example, a state in which the patient is being guided by audio output from the speaker 140 by execution of the processing of step 256L illustrated in FIG. 9A or the processing of step 256S illustrated in FIG. 9B. Moreover, information content of "EXAMINATION CONTENT: FIELD OF VIEW/SLO/OCT" is displayed in the state-of-progress display region 190D2 to indicate the content and sequence of examination. Moreover, information content of "BOTH EYES" is also displayed in the state-of-progress display region 190C2 to indicate the examination subject eyes.

The latest anterior segment image of the patient identified by the patient information 164A displayed in the patient information display region 190D5 is displayed in the image display region 190D3. The information content of "BEING WORN" is displayed in the eyewear wearing state display region 190D4 as information to indicate that the eyewear terminal device 16 is being worn by the patient.

In the example illustrated in FIG. 13, a terminal ID enabling unique identification of a fifth wearable terminal device 12 from out of the six wearable terminal devices 12 with established communication with the management device 14 is displayed in the terminal ID display region 190E1.

In the example illustrated in FIG. 13, the wearable terminal device 12 including the eyewear terminal device 16 with the terminal ID "GZ" is being charged, and so the information content "BEING CHARGED" is displayed in the fifth state-of-progress screen 190E as information to enable the status of being charged to be recognized visually. Information content of "BATTERY 88%" and an indicator of the capacity of the battery is displayed in the fifth state-of-progress screen 190E as information indicating the capacity of the battery.

In the example illustrated in FIG. 13, a terminal ID enabling unique identification of a sixth wearable terminal device 12 from out of the six wearable terminal devices 12 with established communication with the management device 14 is displayed in the terminal ID display region 190F1. Information content of "LEFT EYE: PERFORMING SLO IMAGING" is displayed in the state-of-progress display region 190F2 to indicate that SLO imaging is being performed on the left eye 44R. The information content of "EXAMINATION CONTENT: SLO/OCT" is also displayed in the state-of-progress display region 190F2 to indicate the content and sequence of examination. The information content of "LEFT EYE ONLY" is also displayed to indicate the examination subject eye in the state-of-progress display region 190F2. An indicator is displayed in the state-of-progress display region 190F2 at a being-examined position.

A field-of-view defect map and a right-eye anterior segment image related to the subject eye 44, an SLO image related to the retina 46L, and an OCT image related to the retina 46L are also displayed in the image display region 190F3. Moreover, information content of "BEING WORN" is displayed as information to indicate that the eyewear terminal device 16 is being worn by the patient, and information content of "ERROR" is displayed in the eyewear wearing state display region 190F4.

At step 410 illustrated in FIG. 11, the display control section 184 causes the display 86A to update the display content of information related to the terminal information, and the processing transitions to step 416. The display content of the terminal ID display region 190A1, the state-of-progress display region 190A2, the image display region 190A3, and the eyewear wearing state display region 190A4 is thereby updated.

For example, when the eyewear terminal device 16 is taken off the patient, in the eyewear wearing state display region 190A4, "NOT BEING WORN" is displayed as the information content in the eyewear wearing state display region 190B4 of the second state-of-progress screen 190B. Furthermore, when the error processing of the step 452, described later, is executed, information content of "ERROR" is displayed so as to be indicated in the eyewear wearing state display region 190C4 of the third state-of-progress screen 190C. Moreover, when the OCT imaging is complete, the information content of "OCT IMAGING COMPLETED" is displayed. Moreover, when all the scheduled examinations are complete, a state is adopted in which the indicator is at the examination-completed position. Furthermore, when under guidance of audio from the speaker 140, the information content of "UNDER AUDIO GUIDANCE" is displayed so as to be indicated on the state-of-progress display region 190D2 of the fourth state-of-progress screen 190D.

At step 412, the display control section 184 determines whether or not the patient information 164A is in a non-display state. For example, the display control section 184 determines whether or not the patient information 164A related to the patient using the wearable terminal device 12 identified by the terminal ID being displayed in the terminal ID display region 190A1 is being displayed in the patient information display region 190A5.

Processing transitions to step 414 when affirmative determination is made at step 412, i.e. when the patient information 164A is in the non-display state. Processing transitions to step 416 when negative determination is made at step 412, i.e. when the patient information 164A is in the non-display state, namely when the patient information 164A is being displayed.

At step 414, the display control section 184 causes the display 86A to start displaying the patient information 164A, and then processing transitions to step 416. Thereby, for example, as long as there is patient information 164A related to the patient using the wearable terminal device 12 identified by the terminal ID being displayed in the terminal ID display region 190A1 then the patient information 164A is displayed in the patient information display region 190A5.

At step 416, the display control section 184 determines whether or not an end condition relating to display control processing has been satisfied. The end condition relating to display control processing indicates a condition to end the display control processing. Examples of the end condition relating to display control processing include a condition that a specific period of time has elapsed, a condition that the reception device 84 has received an end instruction, and/or a condition that a situation requiring the display control processing to be forcibly ended has been detected by the CPU 90.

Processing transitions to step 402 when negative determination is made at step 416, i.e. when the end condition relating to display control processing has not been satisfied. Processing transitions to step 418 when affirmative determination is made at step 416, i.e. when the end condition relating to display control processing has been satisfied.

At step 418, the display control section 184 causes the display 86A to end the display of the state-of-progress screen 190, and then ends the display control processing.

Figure 12:
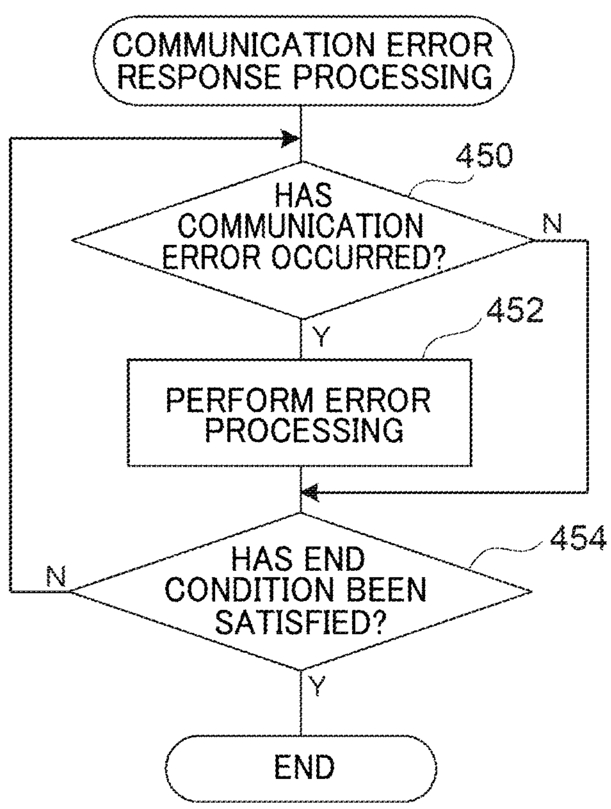
FIG. 12 is a flowchart illustrating an example of a flow of communication error response processing according to the first and second exemplary embodiments.

Next, explanation follows regarding communication error response processing implemented by the CPU 90 executing the communication error response program 94C by the start of execution of the terminal management processing, with reference to FIG. 12. In the following description of the communication error response processing, for ease of explanation, an example will be described of the wearable terminal device 12 identified by the terminal ID being displayed in the terminal ID display region 190C1 of the third state-of-progress screen 190C illustrated in FIG. 13, the management device 14, and the server device 15.

At step 450 in the communication error response processing illustrated in FIG. 12, the display control section 184 determines whether or not a communication error has occurred. The "communication error" referred to here indicates, for example, an error in the communication between the wearable terminal device 12 and the management device 14, or an error in the communication between the management device 14 and the server device 15. These errors in the communication indicate, for example, a phenomenon in which communication is interrupted at an unintentional timing.

Processing transitions to step 454 when negative determination is made at step 450, i.e. when a communication error is not occurring. Processing transitions to step 452 when affirmative determination is made at step 450, i.e. when a communication error has occurred.

At step 452, the display control section 184 executes error processing, and then processing transitions to step 454. The error processing indicates, for example, processing to control the display 86A so as to display information content of "ERROR" in the eyewear wearing state display region 190C4. Moreover, other examples of the error processing include processing to cause a speaker (not illustrated in the drawings) to output audio such as "A COMMUNICATION ERROR HAS OCCURRED".

At step 454, the display control section 184 determines whether or not an end condition relating to communication error response processing has been satisfied. The end condition relating to communication error response processing indicates a condition to end the communication error response processing. Examples of the end condition relating to communication error response processing include a condition that a specific period of time has elapsed, a condition that the reception device 84 has received an end instruction, and/or a condition that a situation requiring the communication error response processing to be forcibly ended has been detected by the CPU 90.

Processing transitions to step 450 when negative determination is made at step 454, i.e. when the end condition relating to communication error response processing has not been satisfied. The communication error response processing is ended when affirmative determination is made at step 454, i.e. when the end condition relating to communication error response processing has been satisfied.

Figure 15:
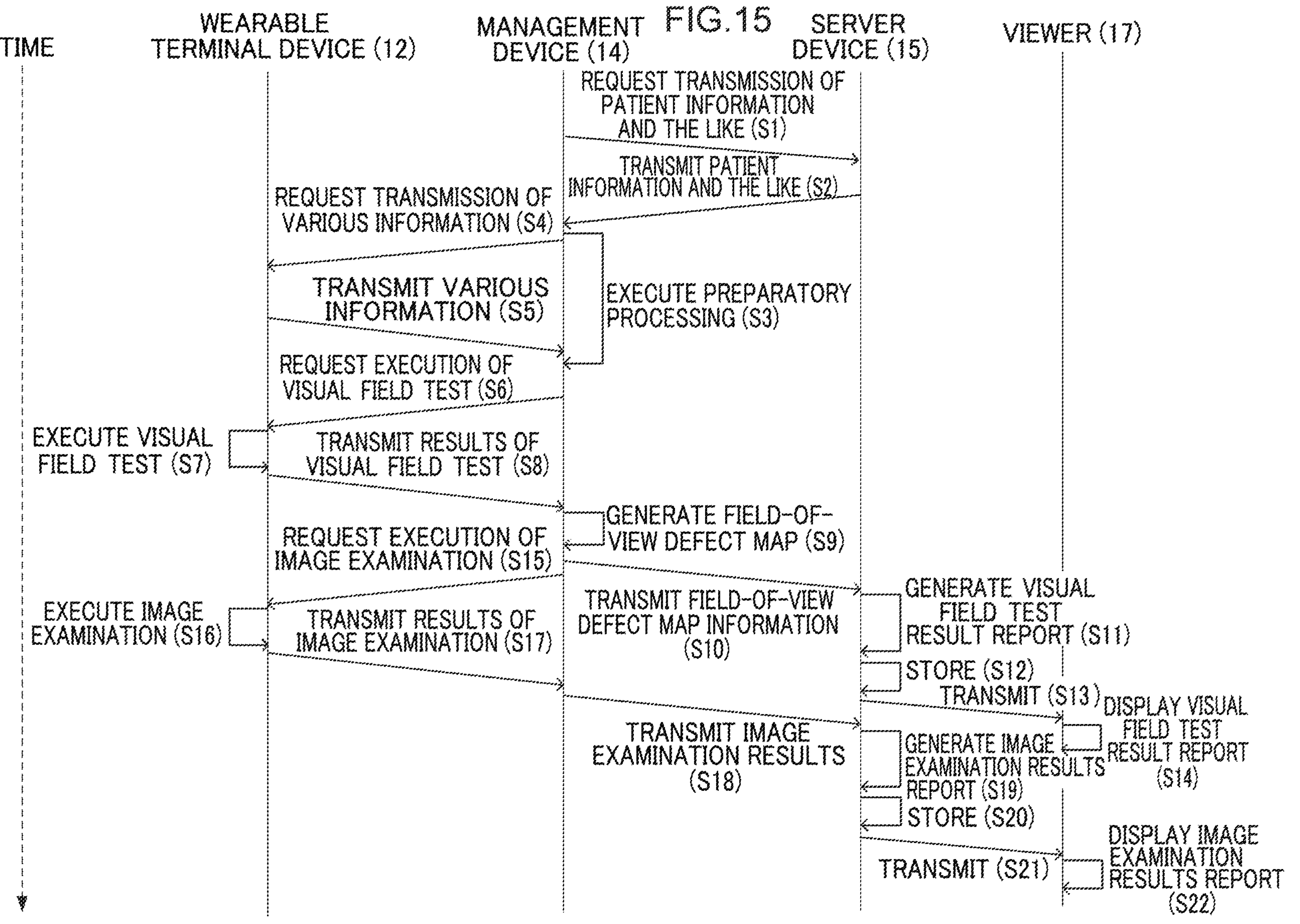
FIG. 15 is a sequencing diagram illustrating an example of principle interactions between a wearable terminal device, a management device, a server device, and a viewer included in an ophthalmic system according to the first exemplary embodiment.

Next explanation follows regarding an example of a flow of processing between the wearable terminal device 12, the management device 14, and the server device 15, with reference to FIG. 15.

As illustrated in the example in FIG. 15, the management device 14 requests transmission of patient information and the like from the server device 15 (S1). The server device 15 transmits the patient information and the like to the management device 14 in response to the request from the management device 14 (S2).

On receipt of the patient information and the like transmitted from the server device 15, the management device 14 executes preparatory processing (S3). The preparatory processing referred to here indicates, for example, the processing of step 212 to step 220 illustrated in FIG. 7A and FIG. 7B. In the preparatory processing, the management device 14 requests the wearable terminal device 12 to transmit various information (S4). The various information indicates, for example, information about the operational status of the wearable terminal device 12. The various information also indicates, for example, information as to whether or not imaging of the anterior segments of the subject eyes 44 has started, information as to whether or not the inter-pupil distance has been detected, and/or information as to whether or not the response button 19 has been pressed.

In response to the request from the management device 14, the wearable terminal device 12 transmits the various information to the management device 14 (S5). On completion of the preparatory processing, the management device 14 requests the wearable terminal device 12 to execute the visual field test (S6).

In response to the request from the management device 14, the wearable terminal device 12 executes the visual field test on the examination subject eye by executing the terminal-side processing as illustrated in the example of FIG. 9A and FIG. 9B (S7). The wearable terminal device 12 transmits visual field test results to the management device 14 (S8). The "visual field test results" referred to here indicates, for example, mark projection position information and sensory information. Note that the "visual field test results" may be merely the mark projection position information related to the position of the mark projected at the timing when the response button 19 was pressed.

In the first exemplary embodiment, as illustrated in the example of FIG. 9B, the wearable terminal device 12 generates the field-of-view defect map information, however technology disclosed herein is not limited thereto and, for example as illustrated in FIG. 15, the management device 14 may generate the field-of-view defect map information.

Namely, in the example illustrated in FIG. 15, the management device 14 generates the field-of-view defect map 240 (see FIG. 13) based on the visual field test results (S9). Thus when the field-of-view defect map 240 is generated by the management device 14, the management device 14 transmits the field-of-view defect map information that is information including the generated field-of-view defect map 240 to the server device 15 (S10).

The server device 15 receives the field-of-view defect map information transmitted from the management device 14, and then generates a visual field test result report indicating the results of the visual field test based on the field-of-view defect map information received (S11). Moreover, the server device 15 stores the generated visual field test result report in the secondary storage section 94 (S12). The server device 15 then transmits the generated visual field test result report to the viewer 17 (S13).

On receipt of the visual field test result report, the viewer 17 displays the received visual field test result report on the display 17C (S14).

The management device 14, however, requests the wearable terminal device 12 to execute an image examination (S15). The wearable terminal device 12 executes the image examination in response to the request from the management device 14 (S16). The wearable terminal device 12 transmits the results of the image examination to the management device 14 (S17).

The management device 14 generates image examination information based on the image examination results transmitted from the wearable terminal device 12, and transmits the generated image examination information to the server device 15 (S18).

The server device 15 receives the image examination information, and generates an image examination report expressing the results of the image examination based on the received image examination information (S19). The server device 15 stores the generated image examination report in the secondary storage section 164 (S20). The server device 15 then transmits the generated image examination report to the viewer 17 (S21).

The viewer 17 receives the image examination report, and displays the received image examination report on the display 17C (S20). Note that the processing indicated at S14 and S20 by the viewer 17 is processing implemented by the CPU 17H reading the viewer-side program 17J1, and executing the read viewer-side program 17J1.

As explained above, the wearable terminal device 12 is equipped with the light management section 116 that includes the light source 114 including the laser light source units 113 and the IR laser light source 114D, and that emits the examination light from the light source 114. The wearable terminal device 12 is equipped with the optical system 27 to guide the light emitted from the light management section 116 to the retina 46R and/or to the retina 46L. The control section 170 is also provided to control the light management section 116 and the optical system 27 such that the examination light is shone onto the retina 46R and/or the retina 46L. Thus the wearable terminal device 12 is able to contribute to carrying out the ophthalmic examinations efficiently.

Moreover, the optical system 27 in the wearable terminal device 12 includes the right-eye optical system 27R to guide the examination light emitted from the light management section 116 onto the retina 46R, and the left-eye optical system 27L to guide the examination light emitted from the light management section 116 onto the retina 46L. Thus the wearable terminal device 12 enables the ophthalmic examinations to be performed on both eyes even without separately securing a light source for the left eye 44L and a light source for the right eye 44R.

Moreover, in the wearable terminal device 12 the light source 114 includes the laser light source units 113, and the control section 170 controls the light management section 116 and the optical system 27 so as to perform visual field test by shining the three primary color laser beam from the laser light source units 113 onto identified positions on the retinas 46. Thus the wearable terminal device 12 enables the laser light source units 113 to perform the visual field tests.

In the wearable terminal device 12, the light source 114 includes the laser light source units 113, and the control section 170 controls the light management section 116 and the optical system 27 so as to perform SLO imaging of the retinas 46 by scanning the three primary color laser beam from the laser light source units 113 onto the retinas 46. Thus the wearable terminal device 12 enables the laser light source units 113 to perform SLO imaging.

Moreover, in the wearable terminal device 12, the light source 114 includes the IR laser light source 114D, and the control section 170 controls the light management section 116 and the optical system 27 so as to perform OCT imaging of the retinas 46 by scanning the IR laser beam from the IR laser light source onto the retinas 46. Thus the wearable terminal device 12 enables the IR laser light source 114D to perform OCT imaging.

Moreover, in the wearable terminal device 12 the control section 170 controls the light management section 116 and the optical system 27 so as to perform a visual field test, SLO imaging, and OCT imaging in the previously mentioned first sequence pattern. Thus the wearable terminal device 12 enables the SLO imaging and the OCT imaging to be performed sequentially based on the results of the visual field test.

The wearable terminal devices 12 are each also equipped with the scanner 28 to scan the three primary color laser beam, and the reflection minor 42 to reflect the three primary color laser beam scanned by the scanner 28 onto the retinas 46. Thus even for patients with cataracts, namely, patients whose lenses are cloudy, the wearable terminal devices 12 enable the three primary color laser beam for visual field tests to be sensed visually.

Moreover, the wearable terminal devices 12 are each also equipped with the right-eye inward-facing camera 48R and the left-eye inward-facing camera 48L to image the anterior segments of the subject eyes 44. The control section 170 then detects the inter-pupil distance based on the right-eye anterior segment image and the left-eye anterior segment image obtained by imaging with the right-eye inward-facing camera 48R and the left-eye inward-facing camera 48L, and controls the position of the reflection mirror 42 based on the detected inter-pupil distance. The wearable terminal devices 12 thereby enable visual field tests to be carried out with good precision even though the inter-pupil distance varies between patients.

Moreover, the wearable terminal devices 12 are each also equipped with the response button 19 to receive operation to indicate whether or not the patient has sensed the three primary color laser beam when the three primary color laser beam has been shone onto the retinas 46. Moreover, the wearable terminal devices 12 are each also equipped with the processing section 171 to output information in response to receipt of operation by the response button 19. In the first exemplary embodiment described above, the processing section 171 transmits sensory information to the management device 14. The wearable terminal devices 12 thus thereby enable a medical service professional to easily ascertain positions on the retinas 46 that are not sensitive to the three primary color laser beam.

Moreover, the wearable terminal devices 12 are each also equipped with the wireless communication section 112 to perform communication with the management device 14 so as to enable the management device 14 to manage the visual field test. The wearable terminal devices 12 thereby enable a reduction to be achieved in the processing load related to management of the visual field test.

Note that the management of the visual field tests is, for example, management including management of the three primary color laser beam used in the visual field tests, and including, by shining the three primary color laser beam onto the retinas 46, management of the sensory information to indicate that patients have visually sensed the shone three primary color laser beam. The wearable terminal devices 12 thus thereby enable at least a reduction to be achieved in the processing load related to managing the three primary color laser beam employed in visual field tests and related to managing the sensory information.

The management device 14 is equipped with the wireless communication section 82 to transmit the control information to the wearable terminal devices 12. The management device 14 is equipped with the acquisition section 182 to acquire from the wearable terminal devices 12 the field-of-view defect map 240, the SLO image, and/or the OCT image that are the results of the ophthalmic examinations performed by shining the examination light onto the retina 46R and/or the retina 46L. Thus the management device 14 enables a contribution to be made to carrying out the ophthalmic examinations efficiently.

Moreover, the management device 14 is also equipped with the display control section 184 to control the display 86A so as to cause the state-of-progress screen 190 that accords with the state of progress of ophthalmic examinations to be displayed on the display 86A. The wearable terminal devices 12 thereby enable a medical service professional to easily ascertain the state of progress of ophthalmic examinations.

Moreover, in the management device 14, the display control section 184 controls the display 86A so as to cause the indicator functioning as the state-of-progress information to indicate the state-of-progress of the ophthalmic examinations to be displayed on the state-of-progress screen 90. Moreover, the display control section 184 controls the display 86A so as to cause the anterior segment image, the SLO image, the OCT image, and/or the field-of-view defect map 240 to be displayed as subject eye feature information expressing features of the subject eye 44 on the state-of-progress screen 90. Thus the wearable terminal device 12 enables a medical service professional to easily ascertain details regarding the state-of-progress of the ophthalmic examinations.

Moreover, in the management device 14, the wireless communication section 82 transmits the examination subject eye instruction information and the patient information 164A to each of the wearable terminal devices 12 by performing wireless communication with each of the plural wearable terminal devices 12. The acquisition section 182 acquires the field-of-view defect map 240, the SLO image, and/or the OCT image that are the results of the ophthalmic examinations from each of the wearable terminal devices 12 by performing wireless communication with each of the plural wearable terminal devices 12. The wearable terminal devices 12 thereby enable a single medical service professional to carry out the ophthalmic examinations on plural patients in parallel.

Second Exemplary Embodiment

Figure 16:
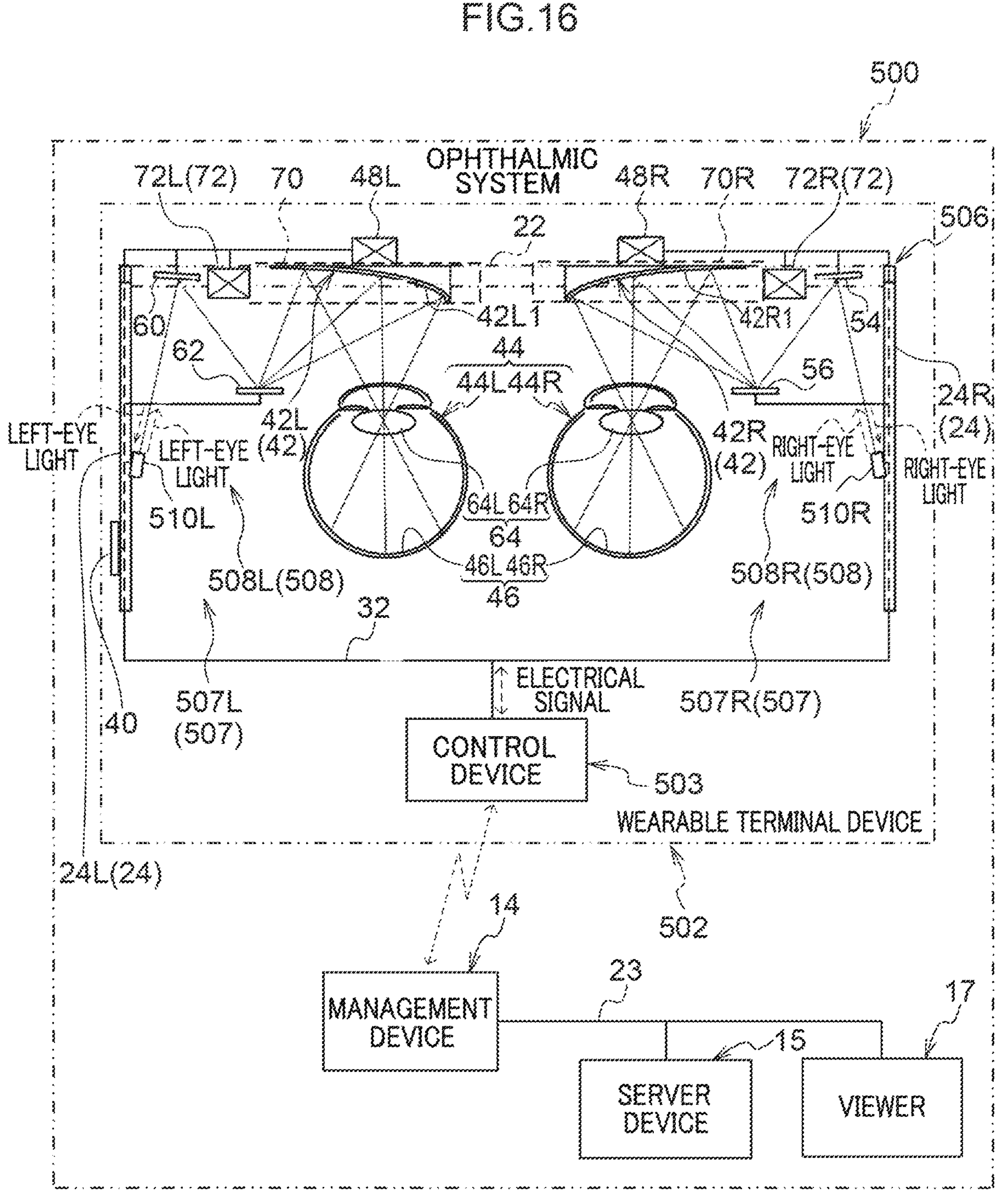
FIG. 16 is a schematic plan view configuration diagram of an example of a configuration of a wearable terminal device included in an ophthalmic system according to the second exemplary embodiment.

Although in the first exemplary embodiment an example has been given in which the light management section 116 manages the examination light and the fundus light, in the second exemplary embodiment explanation follows regarding a case in which the examination light and the fundus light are managed by a right-eye light management section 510R and a left-eye light management section 510L, as in the example illustrated in FIG. 16. Note that configuration elements in the second exemplary embodiment that are the same as those of the first exemplary embodiment are appended with the same reference numerals, duplicate explanation is omitted, and portions that differ from the first exemplary embodiment will be described.

As illustrated in the example of FIG. 16, an ophthalmic system 500 according to the second exemplary embodiment differs from the ophthalmic system 10 in that it includes a wearable terminal device 502 instead of the wearable terminal device 12.

The wearable terminal device 502 differs from the wearable terminal device 12 in that it includes the control device 503 instead of the control device 18, in that it includes an eyewear terminal device 506 instead of the eyewear terminal device 16, and that it does not include the optical splitter 20. Moreover, the wearable terminal device 502 also differs from the wearable terminal device 12 in that it does not include the optical fibers 30, 38, 40. Note that, similarly to the ophthalmic system 10, the ophthalmic system 500 also includes plural of the wearable terminal devices 502, with each of the wearable terminal devices 502 being connected to the management device 14 so as to be in a state capable of wireless communication therewith.

The eyewear terminal device 506 differs from the eyewear terminal device 16 in that it includes the optical system 507 instead of the optical system 27 and includes the scanner 508 instead of the scanner 28

The optical system 507 differs from the optical system 27 in that it includes the right-eye optical system 507R instead of the right-eye optical system 27R and in that it includes the left-eye optical system 507L instead of the left-eye optical system 27L. Moreover, the optical system 507 differs from the optical system 27 in that it includes the scanner 508 instead of the scanner 28.

The scanner 508 differs from the scanner 28 in that it includes a right-eye scanner 508R instead of the right-eye scanner 28R, and includes the left-eye scanner 508L instead of the left-eye scanner 28L.

The right-eye scanner 508R differs from the right-eye scanner 28R in that it includes the right-eye light management section 510R instead of the right-eye light exchange section 52. The left-eye scanner 508L differs from the left-eye scanner 28L in that it includes the left-eye light management section 510L instead of the left-eye light exchange section 58. Namely, the right-eye light management section 510R and the left-eye light management section 510L are built into the eyewear terminal device 506.

As illustrated in the example of FIG. 17, the control device 503 differs from the control device 18 in that it includes a main control section 509 instead of the main control section 110. The main control section 509 differs from the main control section 110 in that it stores a terminal-side program 524A in the secondary storage section 124 instead of the terminal-side program 124A.

The CPU 120 reads the terminal-side program 524A from the secondary storage section 124, and expands the read terminal-side program 524A into the primary storage section 162. The CPU 120 executes the terminal-side program 524A that has been expanded into the primary storage section 122.

The CPU 120 operates as the control section 570 and the processing section 171 by executing the terminal-side program 524A, as illustrated in the example of FIG. 14. The control section 570 differs from the control section 170 in that it controls the optical system 507 instead of the optical system 27. The control section 570 also differs from the control section 170 in that it controls the right-eye light management section 510R and the left-eye light management section 510L instead of the light management section 116.

The right-eye light management section 510R differs from the left-eye light management section 510L in its attachment position to the wearable terminal device 12, however, the internal configuration thereof is similar to the configuration of the left-eye light management section 510L.

Figure 18:
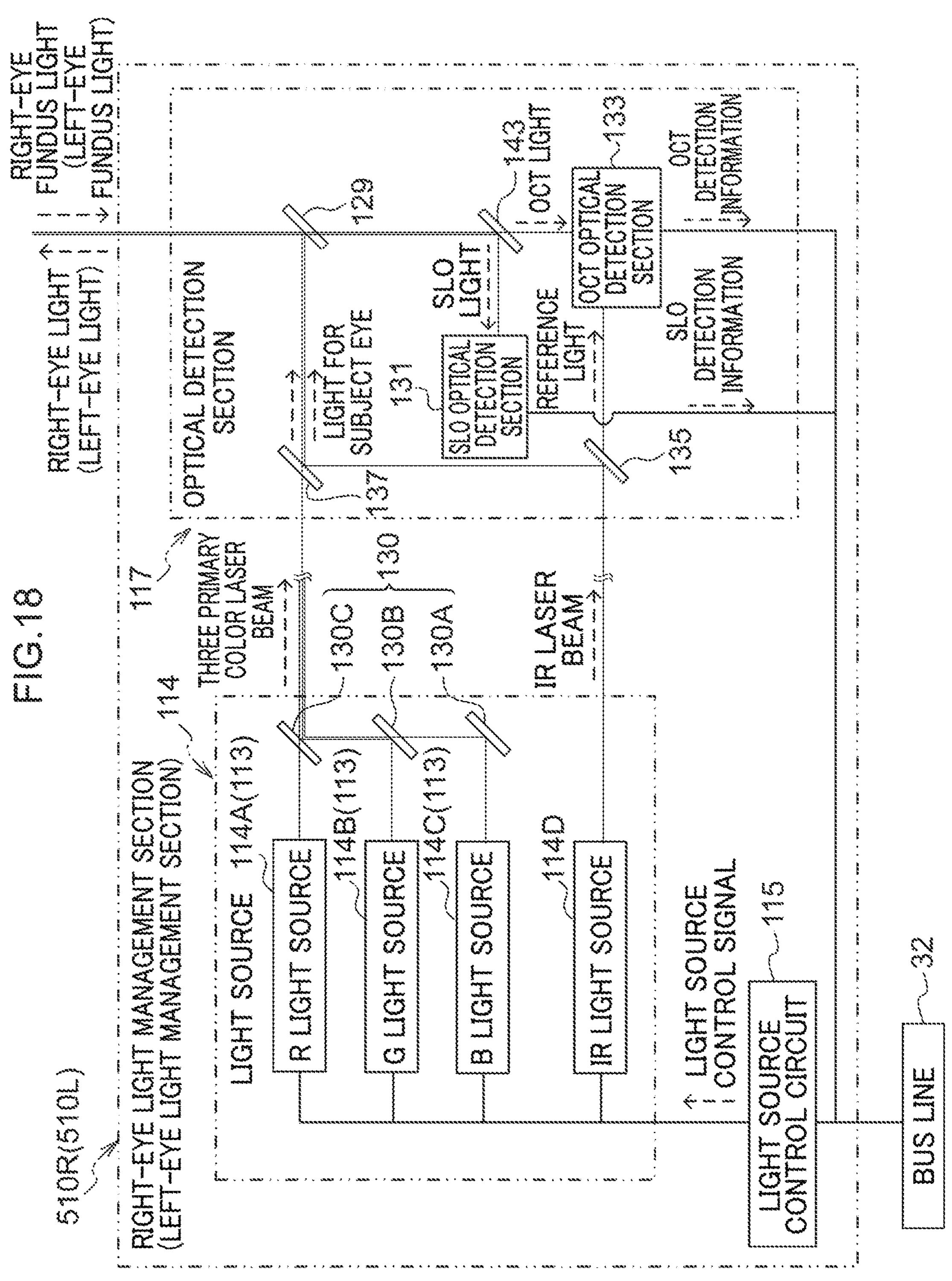
FIG. 18 is a schematic configuration diagram illustrating an example of a configuration of a right-eye light management section (left-eye light management section) of a wearable terminal device included in an ophthalmic system according to the second exemplary embodiment.

As illustrated in the example of FIG. 18, the right-eye light management section 510R differs from the light management section 116 in that the light source control circuit 115 is connected to a bus line. Moreover, the right-eye light management section 510R also differs from the light management section 116 in including an optical detection section 117A instead of the optical detection section 117. The optical detection section 117A differs from the optical detection section 117 in not including a drive source control circuit 119, a detection shutter drive source 123, a minor drive source 125, a shutter 127, a first sliding mechanism 145, or a second sliding mechanism 147.

Moreover, in contrast to the light management section 116 that supplies the right-eye light into the optical fiber 30 and receives the right-eye fundus light from the optical fiber 30, the right-eye light management section 510R emits the right-eye light onto the MEMS minors 54, as in the example illustrated in FIG. 16. Moreover, as illustrated in the example of FIG. 16, the right-eye light management section 510R receives the right-eye fundus light guided by the MEMS minors 54. Note that the right-eye light management section 510R is an example of a right-eye light emitter of the technology disclosed herein. The reference here to "right-eye light" is an example of right-eye examination light according to technology disclosed herein.

As illustrated in the example of FIG. 16, the left-eye light management section 510L is an example of a right-eye light emitter according to technology disclosed herein. The left-eye light management section 510L emits the left-eye light onto the MEMS minor 60, and receives the left-eye fundus light guided by the MEMS minor 60. Reference here to "left-eye light" is an example of left-eye examination light according to technology disclosed herein.

Note that in the wearable terminal device 502 according to the second exemplary embodiment, the right-eye light management section 510R is usable when a right-eye light management section flag is switched ON, and the left-eye light management section 510L is usable when a left-eye light management section flag is switched ON. For ease of explanation, when there is no need in the following to discriminate in the description between the right-eye light management section flag and the left-eye light management section flag they will be referred to as "light management section flags".

Explanation next follows regarding terminal-side processing implemented by the CPU 120 executing the terminal-side program 524A when the main power source (not illustrated in the drawings) of the wearable terminal device 502 has been turned on, with reference to FIG. 19A to FIG. 19C and FIG. 11B.

Note that, for ease of explanation, processing the same as that of the terminal management processing according to the first exemplary embodiment will be appended with the same step number, and explanation thereof will be omitted.

Figure 19A:
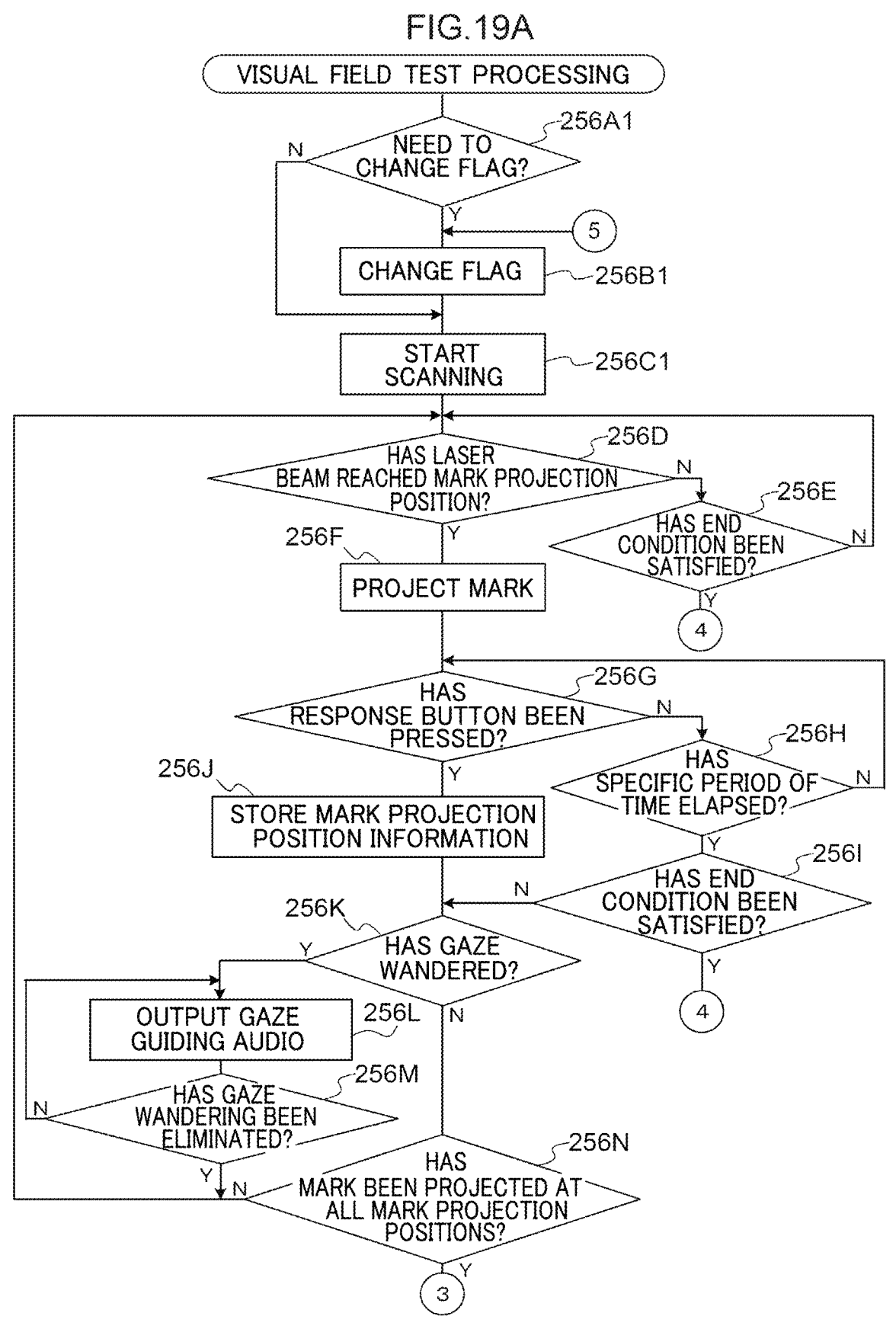

The terminal-side processing according to the second exemplary embodiment differs from the terminal-side processing according to the first exemplary embodiment in including the visual field test processing illustrated in FIG. 19A and FIG. 9B instead of the visual field test processing illustrated in FIG. 9A and FIG. 9B. The visual field test processing according to the second exemplary embodiment (see FIG. 19A) differs from the visual field test processing according to the first exemplary embodiment in including a step 256A1 instead of step 256A, and including step 256B1 instead of step 256B. Moreover, the visual field test processing according to the second exemplary embodiment (see FIG. 19A) differs from the visual field test processing according to the first exemplary embodiment in including a step 256C1 instead of step 256C. Furthermore, the visual field test processing according to the second exemplary embodiment (see FIG. 9B) differs from the visual field test processing according to the first exemplary embodiment in including a step 256U1 instead of step 256U.

Figure 19B:
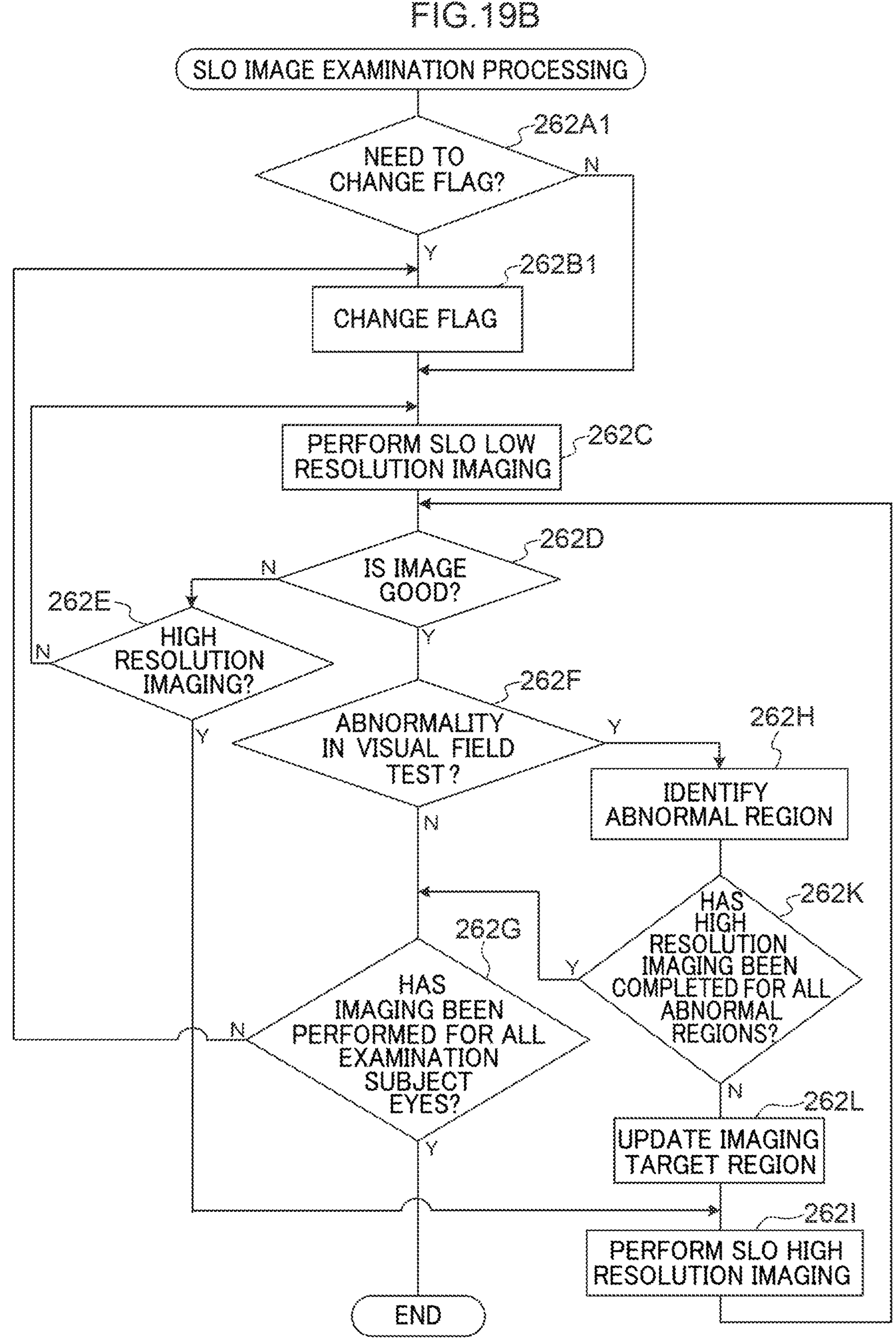
FIG. 19B is a flowchart illustrating an example of a flow of SLO image examination processing included in terminal-side processing according to the second exemplary embodiment.

The terminal-side processing according to the second exemplary embodiment differs from the terminal-side processing according to the first exemplary embodiment in including the SLO image examination processing illustrated in FIG. 19B instead of the SLO image examination processing illustrated in FIG. 9C. The SLO image examination processing according to the second exemplary embodiment (FIG. 19B) differs from the SLO image examination processing according to the first exemplary embodiment in including step 262A1 instead of step 262A, and in including step 262B1 instead of step 262B.

Figure 19C:
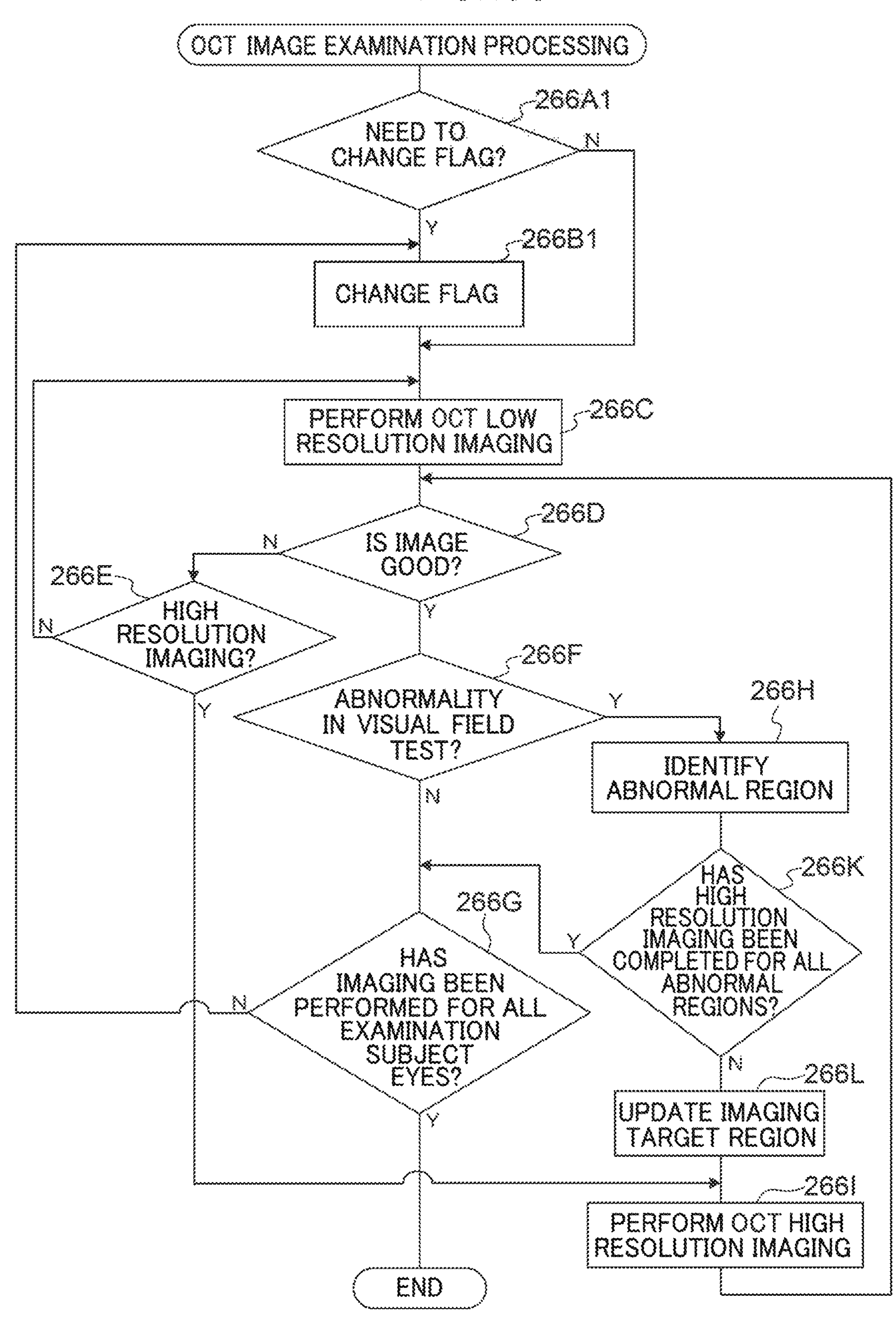
FIG. 19C is a flowchart illustrating an example of a flow of OCT image examination processing included in terminal-side processing according to the second exemplary embodiment.

Moreover, the terminal-side processing according to the second exemplary embodiment differs from the terminal-side processing according to the first exemplary embodiment in including OCT image examination processing illustrated in FIG. 19C instead of the OCT image examination processing illustrated in FIG. 9D. The OCT image examination processing according to the second exemplary embodiment (FIG. 19C) differs from the OCT image examination processing according to the first exemplary embodiment in including step 266A1 instead of step 266A, and including step 266B1 instead of step 266B.

At step 256A1 illustrated in FIG. 19A, the control section 570 determines whether or not a currently ON light management section flag needs to be changed based on the examination subject eye instruction information in the previously mentioned required information included in the visual field test instruction information.

Processing transitions to step 256C1 when negative determination is made at step 256A1, i.e. when there is no need to change the currently ON light management section flag. Processing transitions to step 256B1 when affirmative determination is made at step 256A1, i.e. when the currently ON light management section flag needs to be changed.

Note that processing similar to the processing of step 304A is performed at each of step 262A1 illustrated in FIG. 19B and step 266A1 illustrated in FIG. 19C, and so explanation will be omitted thereof.

At step 256B1, the control section 570 changes the light management section flag based on the examination subject eye instruction information in the previously mentioned required information included in the visual field test instruction information, and then processing transitions to step 256C1. The "changing of the light management section flag" referred to here indicates switching a light management section flag that is ON to OFF, or switching a light management section flag that is OFF to ON.

For example, the right-eye light management section flag is ON and the left-eye light management section flag is OFF when scanning is being performed on the retina 46R with a laser beam. Moreover, the left-eye light management section flag is ON and the right-eye light management section flag is OFF when scanning is being performed on the retina 46L with a laser beam.

Note that processing similar to the processing of step 306A is performed at each of step 262B1 illustrated in FIG. 19B and step 266B1 illustrated in FIG. 19C, and so explanation will be omitted thereof.

At step 256C1, the control section 570 causes the laser beam to start being shone from the light management section corresponding to the light management section flag currently in an ON state from out of the right-eye light management section 510R and the left-eye light management section 510L, so as to start scanning the laser beam onto the retina 46. For example, when the right-eye light management section flag is currently ON, scanning of the retina 46R with the right-eye laser beam is started by starting to shine the right-eye laser beam from the right-eye light management section 510R. Moreover, for example, when the left-eye light management section flag is currently ON, then scanning of the left-eye laser beam onto the retina 46L is started by starting to shine the left-eye laser beam from the left-eye light management section 510L.

At step 256U1 illustrated in FIG. 9B, the control section 570 controls the right-eye light management section 510R when the retina 46R is being scanned by the right-eye laser beam so as to end scanning by the right-eye light management section 510R. The control section 570 also controls the left-eye light management section 510L when the retina 46L is being scanned by the left-eye laser beam so as to end scanning by the left-eye light management section 510L.

As described above, the wearable terminal device 502 is equipped with the optical system 507 to guide the right-eye light to the retina 46R and to guide the left-eye light to the retina 46L. The wearable terminal device 502 is equipped with the control section 570 to control the right-eye light management section 510R and the left-eye light management section 510L so that examination light is shone on the retina 46R and/or the retina 46L. The wearable terminal device 502 is thereby able to contribute to carrying out the ophthalmic examinations efficiently. The wearable terminal device 502 also enables SLO imaging to be performed on one out of the right eye 44R or the left eye 44L while performing OCT imaging on the other thereof. Furthermore, the wearable terminal device 502 enables a visual field test to be performed on one out of the right eye 44R or the left eye 44L while performing at least one out of SLO imaging or OCT imaging on the other thereof.

Third Exemplary Embodiment

Although in the first exemplary embodiment a case applied with the optical splitter 20 was described, in the third exemplary embodiment an example of implementing the technology disclosed herein without using an optical splitter 20 will be described. Note that in the third exemplary embodiment the same reference numerals will be appended to configuration elements that are the same as those of the first exemplary embodiment and explanation thereof will be omitted, with explanation given of portions that differ from the first exemplary embodiment.

Figure 23:
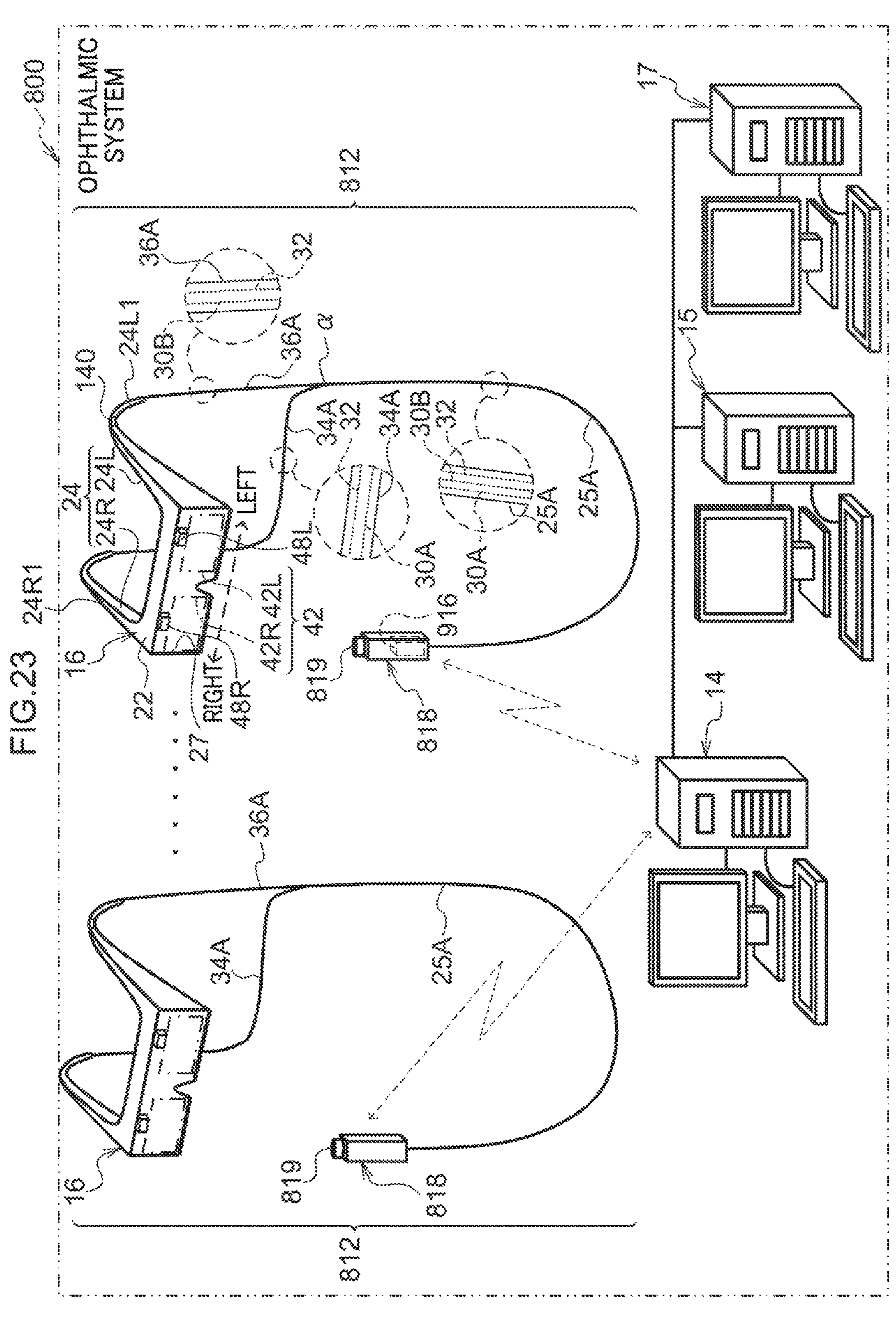
FIG. 23 is a schematic diagram illustrating an example of an overall configuration of an ophthalmic system according to the third exemplary embodiment.

As illustrated in the example of FIG. 23, an ophthalmic system 800 according to the third exemplary embodiment differs from the ophthalmic system 10 of the first exemplary embodiment in that it includes a wearable terminal device 812 instead of the wearable terminal device 12.

The wearable terminal device 812 differs from the wearable terminal device 12 in that it does not include an optical splitter 20. Moreover, the wearable terminal device 812 differs from the wearable terminal device 12 in that it includes a control device 818 instead of the control device 18. Furthermore, the wearable terminal device 812 differs from the wearable terminal device 12 in that it includes a cable 25A instead of the cable 25, includes a cable 34A instead of the cable 34, and includes a cable 36A instead of the cable 36.

The cable 25A differs from the cable 25 in that it includes optical fibers 30A, 30B instead of the optical fiber 30. The cable 34A differs from the cable 34 in that it includes the optical fiber 30A instead of the optical fiber 38. The cable 36A differs from the cable 36 in that it includes an optical fiber 36B instead of the optical fiber 40. Namely, the cable 25A in the third exemplary embodiment is branched into two cables, the cables 34A, 36A, at a branch section a.

The control device 818 differs from the control device 18 in that it includes a light management section 819 instead of the light management section 116.

As illustrated in the example in FIG. 24, the light management section 916 differs from the light management section 116 in that it includes an optical detection section 917 instead of the optical detection section 117. The optical detection section 917 differs from the optical detection section 117 in that it further includes a drive source control circuit 119, a detection shutter drive source 123, a mirror drive source 125, a shutter 127, a mirror 141, a first sliding mechanism 145, and a second sliding mechanism 147.

The second sliding mechanism 147 holds the beam splitter 129 so as to be slideable between a seventh position P7 and an eighth position P8. The seventh position P7 indicates a position to guide left-eye light into the optical fiber 30 by reflecting examination light that has been guided by the mirror 137. The eighth position P8 indicates a position to guide right-eye light to the optical fiber 30A by reflecting examination light that has been guided by the mirror 137.

The first sliding mechanism 145 holds the shutter 127 so as to be slideable between a fifth position P5 and a sixth position P6. The fifth position P5 indicates a position to transmit right-eye light guided by the beam splitter 129 at the eighth position P8 and to guide the right-eye light into the optical fiber 30A. The sixth position P6 indicates a position to transmit left-eye light guided by the beam splitter 129 at the seventh position P7 and to guide the left-eye light into the optical fiber 30B.

Examples of the detection shutter drive source 123 and the minor drive source 125 include a stepping motor, a solenoid, and a piezoelectric element or the like. The detection shutter drive source 123 and the mirror drive source 125 are connected to the drive source control circuit 119, and the drive source control circuit 119 is connected to the I/O 128. A drive source control signal from the CPU 120 is input to the drive source control circuit 119, and the drive source control circuit 119 controls the detection shutter drive source 123 and the mirror drive source 125 according to the input drive source control signal. For example, the drive source control circuit 119 controls the detection shutter drive source 123 by supplying a detection shutter control signal to the detection shutter drive source 123, and controls the mirror drive source 125 by supplying a minor control signal to the minor drive source 125.

The first sliding mechanism 145 is connected to the detection shutter drive source 123, and slides the shutter 127 between the fifth position P5 and the sixth position P6 on receipt of motive force generated by the detection shutter drive source 123.

The second sliding mechanism 147 is connected to the mirror drive source 125, and slides the beam splitter 129 between the seventh position P7 and the eighth position P8 on receipt of motive force generated by the mirror drive source 125.

The mirror 141 is a reflection mirror, and by reflecting the right-eye fundus light that has been transmitted through the beam splitter 129 in the eighth position P8, guides the right-eye fundus light to the minor 143. The minor 143 is disposed along the direction of progression of the left-eye fundus light that has been transmitted through the beam splitter 129 in the seventh position P7, and along the direction of progression of the right-eye fundus light reflected by the mirror 141.

The mirror 143 is a dichroic mirror that separates the fundus light into SLO light and OCT light, guides the SLO light into the SLO optical detection section 131, and guides the OCT light into the OCT optical detection section 133. Namely, the mirror 143 transmits the right-eye SLO light from out of the right-eye fundus light guided by the minor 141, so as to guide the right-eye SLO light into the SLO optical detection section 131, and reflects the right-eye OCT light so as to guide the right-eye OCT light into the OCT optical detection section 133. Moreover, the mirror 143 reflects the left-eye SLO light from out of the left-eye fundus light that has been transmitted through the beam splitter 129 in the seventh position P7 so as to guide the left-eye SLO light into the SLO optical detection section 131, and transmits the left-eye OCT light so as to be guided into the OCT optical detection section 133.

In the wearable terminal device 812 configured as described above, the right-eye light from the light management section 916 is supplied into the right-eye optical system 27R through the optical fiber 30A, and the left-eye light from the light management section 916 is supplied into the left-eye optical system 27L through the optical fiber 30B.

Figure 20:
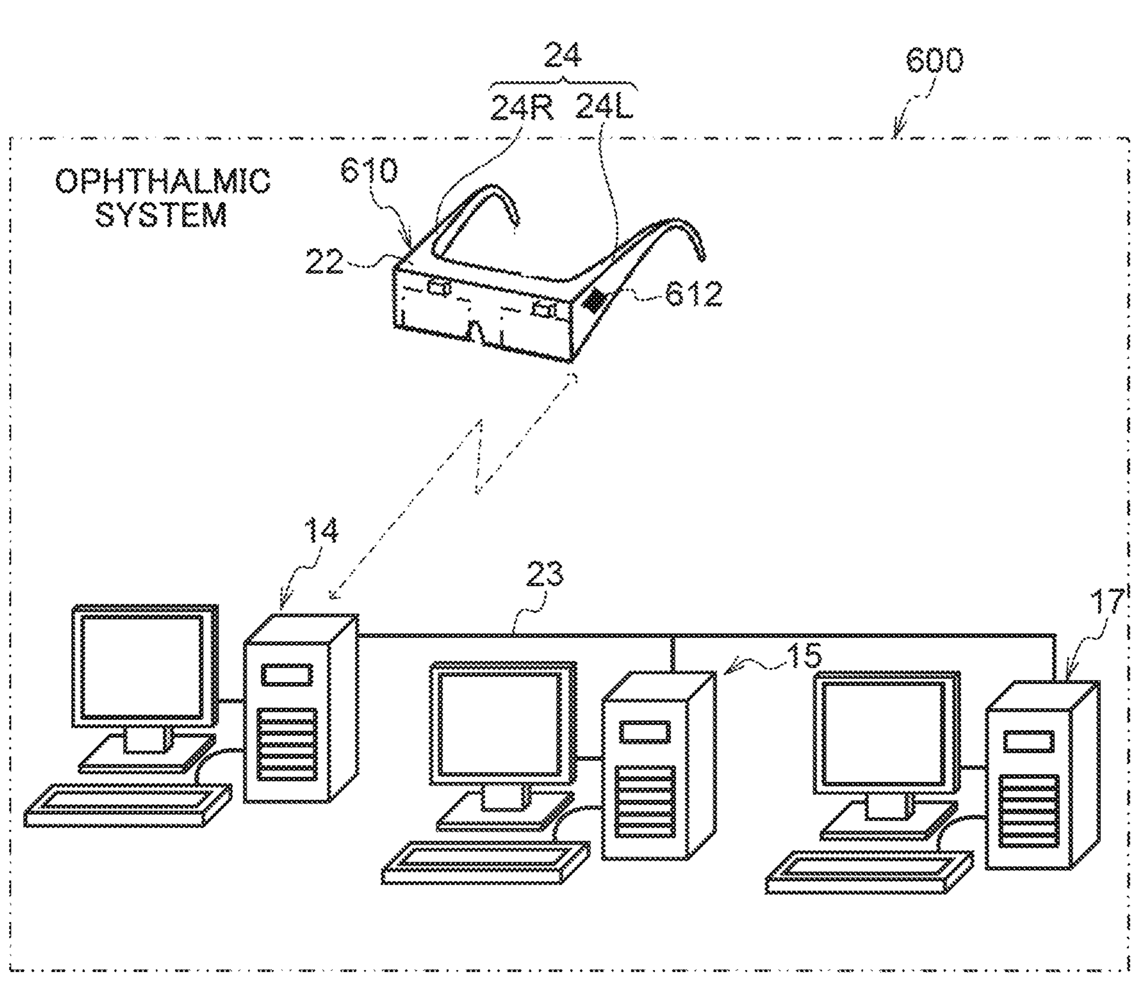
FIG. 20 is a schematic diagram illustrating a modified example of an ophthalmic system according to the first and second exemplary embodiments.

Note that although an example is given in the first exemplary embodiment of the wearable terminal device 12 in which the control device 18 and the optical splitter 20 are external to the eyewear terminal device 16, technology disclosed herein is not limited thereto. For example, an ophthalmic system 600 as illustrated in FIG. 20 may be employed instead of the ophthalmic system 10.

The ophthalmic system 600 differs from the ophthalmic system 10 in that it does not include the control device 18, the optical splitter 20, nor the cables 25, 34, 36. The ophthalmic system 600 also differs from the ophthalmic system 10 in that it includes an eyewear terminal device 610 instead of the eyewear terminal device 16.

The eyewear terminal device 610 includes a controller 352 that is a device with functionality equivalent to that of the control device 18 and a device with functionality equivalent to that of the optical splitter 20 integrated together and housed in the left temple piece 24L. In such a configuration cables equivalent to the cables 34, 36 are also housed in the frame of the eyewear terminal device 350. The frame of the eyewear terminal device 350 indicates, for example, the rim piece 22 and the temple piece 24.

An example of a method to detect an answer-response with the eyewear terminal device 610 is a method in which an answer-response is detected by a touch sensor (not illustrated in the drawings) provided in the temple piece 24 being touched by a patient. Another example of a method to detect an answer-response with the eyewear terminal device 610 is a method in which an answer-response is detected using a speech recognition device. In such cases, for example, the speech recognition device detects an answer-response by recognizing the "YES" (an expression of decision that a mark (light) has been sensed) or the "NO" (an expression of decision that a mark (light) has not been sensed) of a patient. Moreover, a configuration may be adopted in which the patient is required to grip a separately configured response button 19, such that a response result of the response button 19 is transmitted to the eyewear terminal device 610.

The controller 352 may be provided in the right temple piece 24R. Moreover, a configuration may be adopted in which a device with functionality equivalent to that of the control device 18 and a device with functionality equivalent to that of the optical splitter 20 are separately housed in the frame of the eyewear terminal device 350. In such cases, a cable equivalent to that of the cable 25, namely, the cable connecting together the device with functionality equivalent to that of the control device 18 and the device with functionality equivalent to that of the optical splitter 20, is also housed in the frame of the eyewear terminal device 350.

The eyewear terminal device 610 thereby renders the cables 25, 34, 36 and the optical splitter 20 redundant, enabling a contribution to be made to greater compactness of the device overall.

Note that the wearable terminal device 500 according to the second exemplary embodiment is also configurable as a wireless wearable terminal device as in the wearable terminal device 610 illustrated in FIG. 20. Namely, a configuration may be adopted in which the wearable terminal device incorporates an eyewear terminal device including at least the optical system 507 from out of the devices equivalent to the right-eye light management section 510R, the left-eye light management section 510L, the optical system 507, and the control device 503. Such a configuration also enables a contribution to be made to greater compactness of the device overall.

Moreover, although the shutters 121, 127 has been given as an example in the first exemplary embodiment, the technology disclosed herein is not limited thereto, and, instead of the shutters 121, 127, a device may be employed that is capable of being controlled so as to let light pass through, such as a liquid crystal shutter.

Moreover, although in each of the exemplary embodiment described above cases are described in which the light source 114 includes the laser light source units 113 and the IR laser light source 114D, the technology disclosed herein is not limited thereto. For example, as long as the SLO imaging and the visual field test are executable on their own, the IR laser light source 114D is not required.

Moreover, although laser beams have been given as examples in each of the exemplary embodiments described above, technology disclosed herein is not limited thereto, and, for example, light from super luminescent diodes may be employed instead of laser beams.

Moreover, although the response button 19 has been given as an example in each of the exemplary embodiments described above, the technology disclosed herein is not limited thereto. For example, instead of the response button 19, a touch panel display, keyboard, or a mouse or the like may be employed.

Moreover, although examples have been given in the exemplary embodiments described above in which the field-of-view defect map is generated by the wearable terminal device 12 (502), the technology disclosed herein is not limited thereto. For example, as illustrated in FIG. 15, the field-of-view defect map may be generated by the management device 14. In such cases, for example, a configuration may be adopted in which the processing section 171 generates correspondence information corresponding sensory information with mark projection position information related to the sensory information, transmits the generated correspondence information to the management device 14 through the wireless communication section 112, and the management device 14 generates an field-of-view defect map based on the correspondence information. Note that the mark projection position information related to the sensory information indicates mark projection position information corresponding to the position where the mark was being projected at the timing the response button 19 was pressed. Alternatively, a configuration may be adopted in which the processing section 171 transmits the mark projection position information corresponding to the position where the mark was being projected at the timing the response button 19 was pressed to the management device 14 through the wireless communication section 112, and the management device 14 generates the field-of-view defect map based on the mark projection position information.

Moreover, although each of the exemplary embodiment described above includes, as light sources of different modalities (a light source for SLO imaging and a light source for OCT imaging), the laser light source units 113 as examples of the first light source unit according to technology disclosed herein, and the IR laser light source 114D as an example of the second light source unit according to technology disclosed herein, the technology disclosed herein is not limited thereto. For example, two light sources of different wavelengths may be employed instead of the laser light source units 113 and the IR laser light source 114D. Examples of such wavelengths include, for example, a wavelength in the R band, a wavelength in the B band, a wavelength in the G band, and a wavelength in an IR band. In such cases, for example, two light sources may both be light sources for SLO in a configuration in which SLO imaging is performed by shining a laser beam with a wavelength in the R band onto the retina 46L from one of the light sources, and SLO imaging is performed by shining a laser beam with a wavelength in the G band onto the retina 46R from the other of the light sources. Note that similar also applies to OCT imaging of both eyes.

Moreover, although examples have been given in which the MEMS mirrors 54, 56, 60, 62 were employed in the exemplary embodiment described above, the technology disclosed herein is not limited thereto. For example, instead of the MEMS mirrors 54, 56, 60, 62, or together with one or more of the MEMS mirrors 54, 56, 60, 62, a minor such as a galvanometer mirror and/or a polygon mirror or the like that enables electrical control of the position on the reflection face may be employed.

Figure 21:
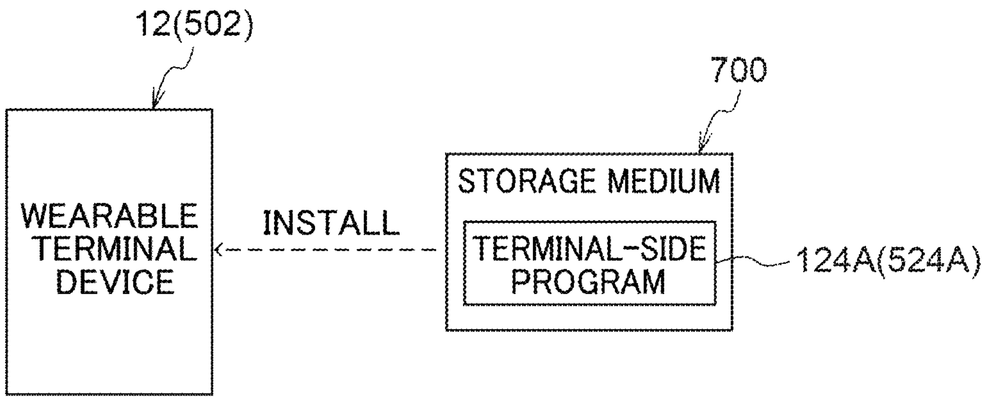
FIG. 21 is a schematic diagram illustrating an example of a manner in which a terminal-side program according to the first and second exemplary embodiments is installed in a wearable terminal device.

Moreover, although examples have been given in the exemplary embodiments described above in which the terminal-side program 124A (524A) is read from the secondary storage section 124, the terminal-side program 124A (524A) does not necessarily have to be initially stored on the secondary storage section 124. For example, as illustrated in FIG. 21, a configuration may be adopted in which the terminal-side program 124A (524A) is first stored on a freely selected portable storage medium 700 such as an SSD, USB memory, or DVD-ROM or the like. In such a configuration the terminal-side program 124A (524A) on the storage medium 700 is then installed on the wearable terminal device 12 (502), and the installed terminal-side program 124A (524A) then executed by the CPU 120.

Moreover, a configuration may be adopted in which the terminal-side program 124A (524A) is stored on a storage section of another computer or server device or the like connected to the wearable terminal device 12 (502) over a communication network (not illustrated in the drawings), such that the terminal-side program 124A (524A) is then installed in response to a request from the wearable terminal device 12 (502). In such a configuration, the installed terminal-side program 124A (524A) is then executed by the CPU 120.

Figure 22:
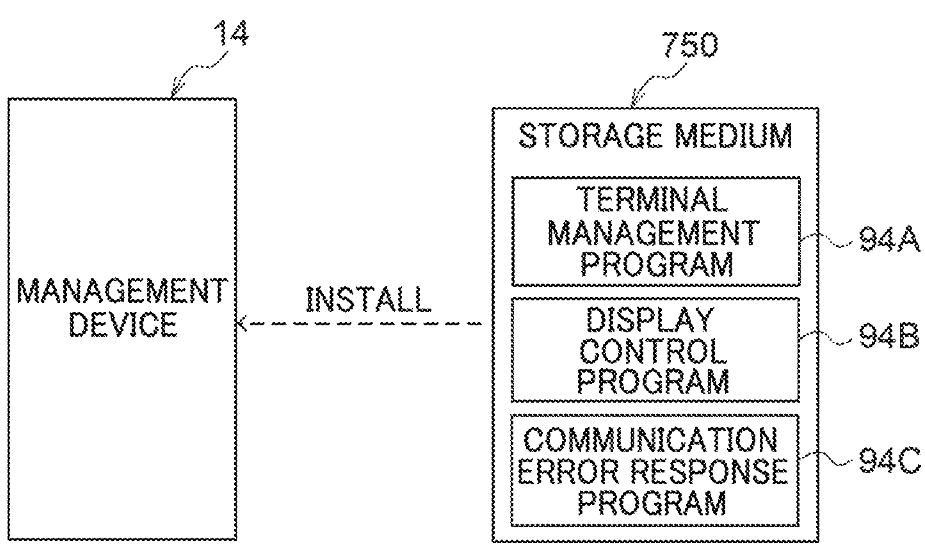
FIG. 22 is a schematic diagram illustrating an example of a manner in which a management device-side program according to the first and second exemplary embodiments is installed in a management device.

Moreover, although explanation has been given in the exemplary embodiment described above in which the management device-side program is read from the secondary storage section 94, the management device-side program does not necessarily have to be initially stored on the secondary storage section 94. For example, a configuration may be adopted in which, as illustrated in FIG. 22, the management device-side program is first stored on a freely selected portable storage medium 750 such as an SSD, USB memory, or DVD-ROM or the like. In such a configuration the management device-side program on the storage medium 750 is then installed on the management device 14, and the installed management device-side program is then executed by the CPU 90.

Moreover, a configuration may be adopted in which the management device-side program is stored on a storage section of another computer or server device or the like connected to the management device 14 over a communication network (not illustrated in the drawings), such that the management device-side program is then installed in response to a request from the management device 14. In such a configuration, the installed management device-side program is then executed by the CPU 90.

Moreover, the terminal management processing, the terminal-side processing, the server-side processing, the display control processing, and the communication error response processing in the exemplary embodiment described above are merely given as examples thereof. Thus obviously steps that are not required may be removed, new steps may be added, and the sequence of processing may be switched around within a range not departing from the spirit thereof.

Moreover, although examples are given in the exemplary embodiments described above of cases in which the terminal management processing, the terminal-side processing, the server-side processing, the display control processing, and the communication error response processing are implemented by a software configuration utilizing a computer, the technology disclosed herein is not limited thereto. For example, instead of a software configuration utilizing a computer, one or more processing from out of the terminal management processing, the terminal-side processing, the server-side processing, the display control processing, and the communication error response processing may be executed by a purely hardware configuration, i.e. a FPGA or ASIC configuration or the like. One or more type of processing from out of the terminal management processing, the terminal-side processing, the server-side processing, the display control processing, and the communication error response processing may also be executed by configuration combining a software configuration and a hardware configuration.

Namely, examples of hardware resources to execute the various types of processing such as the terminal management processing, the terminal-side processing, the server-side processing, the display control processing, and the communication error response processing include CPUs that are general purpose processors that function as hardware resources to execute various types of processing by executing programs. Moreover, other examples of hardware resources include dedicated electronic circuits that are processors including circuit configurations such as FPGA, PLD, and ASIC configurations of dedicated design. Moreover, electronic circuits that combine circuit elements such as semiconductor elements and the like may also be employed as hardware structures of such processors. The hardware resources to execute the various types of processing may be one type from out of the plural types of processor described above, or a combination may be adopted of two or more processors that are of the same type or of a different type.

Moreover, for the processing section 180, the acquisition section 182, and the display control section 184 of the management device 14 in the example illustrated in FIG. 14, application may be made to a management device that, instead of being connected to wearable ophthalmic instruments, is connected in a communicable manner to a device including visual field test/SLO/OCT functionality capable of observing both eyes in a static device (for example, a static ophthalmic instrument). Namely, the processing executed by the management device 14 is also executable on a static device including visual field test/SLO/OCT functionality capable of observing both eyes.

In the present specification, “A and/or B” has the same meaning as “at least one out of A or B”. Namely, “A and/or B” may mean only A, may mean only B, or may mean a combination of A and B. Moreover, in the present specification, an expression in which three or more terms are linked together with “and/or” should be interpreted in a similar manner to “A and/or B”.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. An ophthalmic instrument comprising:

a light emitter that emits light from a light source for examining a subject eye;

an optical system to guide the light onto the subject eye;

an eyewear terminal configured to house the light emitter and the optical system, the eyewear terminal being worn by a patient;

a wearing detector configured to detect whether the eyewear terminal is being worn by the patient; and a control section configured to transmit a detection result by the wearing detector to an external management device, to receive, from the external management device, examination type identification information identifying respective types of a plurality of ophthalmic examinations to be performed on the subject eye and examination sequence information indicating an order in which the plurality of ophthalmic examinations are to be performed, and to control the light emitter, and the optical system based on the examination type identification information and the examination sequence information.

2. The ophthalmic instrument of claim 1, wherein the light source includes a first light source for SLO imaging emitting visible light and a second light source for OCT imaging emitting infrared light.

3. The ophthalmic instrument of claim 2, wherein the control section controls the light emitter to emit the visible light so as to irradiate a specific position at a retina of the subject eye for a visual field test.

4. The ophthalmic instrument of claim 1, further comprising:

an anterior segment camera configured to image an anterior segment of the subject eye, wherein the control section detects an inter-pupil distance based on the anterior segment image obtained by the anterior segment camera and controls the light emitter to change an irradiating position of the light based on the inter-pupil distance.

5. The ophthalmic instrument of claim 4, wherein the control section changes the irradiation position of the light based on identification information identifying the ophthalmic instrument and the inter-pupil distance.

* * * * *